United States Patent
Kikuchi et al.

(10) Patent No.: US 12,042,560 B2
(45) Date of Patent: Jul. 23, 2024

(54) LIPOSOME COMPOSITION

(71) Applicant: Eisai R&D Management Co., Ltd., Tokyo (JP)

(72) Inventors: Hiroshi Kikuchi, Tsukuba (JP); Kenji Hyodo, Tsukuba (JP); Hiroshi Ishihara, Tsukuba (JP)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 0 days.

(21) Appl. No.: 14/061,426

(22) Filed: Oct. 23, 2013

(65) Prior Publication Data

US 2014/0044777 A1    Feb. 13, 2014

Related U.S. Application Data

(63) Continuation of application No. 13/260,872, filed as application No. PCT/JP2010/055770 on Mar. 30, 2010, now abandoned.

(60) Provisional application No. 61/164,653, filed on Mar. 30, 2009.

(30) Foreign Application Priority Data

Mar. 30, 2009    (JP) ................... 2009-082521

(51) Int. Cl.
*A61K 9/127*    (2006.01)
*A61K 31/357*    (2006.01)

(52) U.S. Cl.
CPC ............ *A61K 9/127* (2013.01); *A61K 9/1271* (2013.01); *A61K 9/1277* (2013.01); *A61K 9/1278* (2013.01); *A61K 31/357* (2013.01)

(58) Field of Classification Search
None
See application file for complete search history.

(56) References Cited

U.S. PATENT DOCUMENTS

| | | | |
|---|---|---|---|
| 5,192,549 A | 3/1993 | Barenolz et al. |
| 5,316,771 A | 5/1994 | Barenholz et al. |
| 5,571,534 A | 11/1996 | Jalonen et al. |
| 5,736,155 A | 4/1998 | Bally et al. |
| 5,759,573 A | 6/1998 | Kim |
| 5,821,349 A | 10/1998 | Djedaini-Pilard et al. |
| 6,051,251 A | 4/2000 | Zalipsky et al. |
| 6,214,865 B1 | 4/2001 | Littlefield et al. |
| 6,469,182 B1 | 10/2002 | Littlefield et al. |
| 6,653,341 B1 | 11/2003 | Littlefield et al. |
| 6,747,011 B1 | 6/2004 | Zhang |
| 7,488,802 B2 | 2/2009 | Collins et al. |
| 7,521,051 B2 | 4/2009 | Collins et al. |
| 7,982,060 B2 | 7/2011 | Austad et al. |
| 8,008,449 B2 | 8/2011 | Korman et al. |
| 8,093,410 B2 | 1/2012 | Chase et al. |
| 8,168,757 B2 | 5/2012 | Finnefrock et al. |
| 8,350,067 B2 | 1/2013 | Endo et al. |
| 8,354,509 B2 | 1/2013 | Carven et al. |
| 8,383,796 B2 | 2/2013 | Korman et al. |
| 9,968,583 B2 | 5/2018 | Kikuchi et al. |
| 10,945,990 B2 | 3/2021 | Matsui et al. |
| 11,071,713 B2 | 7/2021 | Kikuchi et al. |
| 11,083,705 B2 | 8/2021 | Semba et al. |
| 2002/0131995 A1 | 9/2002 | Szoka, Jr. |
| 2004/0156889 A1* | 8/2004 | Hu .......... A61K 31/137 424/450 |
| 2005/0118249 A1 | 6/2005 | Webb et al. |
| 2005/0118250 A1 | 6/2005 | Tardi et al. |
| 2006/0008909 A1 | 1/2006 | Cullis et al. |
| 2006/0104984 A1 | 5/2006 | Littlefield et al. |
| 2006/0147511 A1 | 7/2006 | Panzner et al. |
| 2007/0112176 A1 | 5/2007 | Seiki et al. |
| 2007/0116753 A1 | 5/2007 | Hong et al. |
| 2007/0155696 A1 | 7/2007 | Ishihara et al. |
| 2007/0244187 A1 | 10/2007 | Austad et al. |
| 2009/0196913 A1 | 8/2009 | Huang et al. |
| 2009/0196918 A1 | 8/2009 | Joguparthi et al. |
| 2010/0247629 A1 | 9/2010 | Gabizon et al. |
| 2011/0018419 A1 | 1/2011 | Suzuki et al. |
| 2011/0184190 A1 | 7/2011 | Endo et al. |
| 2011/0262524 A1 | 10/2011 | Bally et al. |
| 2011/0271358 A1 | 11/2011 | Freeman et al. |
| 2012/0058178 A1 | 3/2012 | Kikuchi et al. |
| 2012/0128757 A1 | 5/2012 | Kikuchi et al. |
| 2014/0212479 A1 | 7/2014 | Zeinelden |
| 2014/0248263 A1 | 9/2014 | Andersen et al. |
| 2015/0005343 A1 | 1/2015 | Nomoto et al. |
| 2015/0210769 A1 | 7/2015 | Freeman et al. |

(Continued)

FOREIGN PATENT DOCUMENTS

| | | |
|---|---|---|
| BR | PI 1014527-3 | 4/2016 |
| CA | 2673924 | 7/2008 |

(Continued)

OTHER PUBLICATIONS

"Residues" downloaded from www.freedictionary.com on Jul. 15, 2014.*
Cullis et al. pH Gradients and Membrane Transport in Liposomal Systems. Trends In Biotechnology, 1991. 9(8)268-272.*
Material Safety Data Sheet for Eribulin mesylate, 2009, 6 pages.*
Onium Compounds Entry. IUPAC Gold Book. 2 pages. From http://goldbook.iupac.org/O04291.html, Downloaded on Mar. 9, 2016.*
Ammonium Cations. The Illustrated Glossary of Organic Chemistry, 1 page, http://www.chem.ucla.edu/harding/IGOC/A/ammonium_cation.html, downloaded on Mar. 9, 2016.*

(Continued)

*Primary Examiner* — Allison M Fox
*Assistant Examiner* — Kimberly A Aron
(74) *Attorney, Agent, or Firm* — Sterne, Kessler, Goldstein & Fox P.L.L.C.

(57) ABSTRACT

The present invention provides a novel liposome composition containing eribulin or its pharmacologically permissible salt, and its method of manufacture.

5 Claims, 3 Drawing Sheets

(56) References Cited

U.S. PATENT DOCUMENTS

| | | |
|---|---|---|
| 2015/0246033 A1 | 9/2015 | Flynn et al. |
| 2016/0235671 A1 | 8/2016 | Li et al. |
| 2016/0296633 A1 | 10/2016 | Goldenberg et al. |
| 2016/0338954 A1 | 11/2016 | Brinker et al. |
| 2017/0020817 A1 | 1/2017 | Singh |
| 2017/0071903 A1 | 3/2017 | Funahashi et al. |
| 2018/0071247 A1 | 3/2018 | Matsui et al. |
| 2019/0010232 A1 | 1/2019 | Kalos et al. |
| 2019/0111022 A1 | 4/2019 | Asano et al. |
| 2019/0263927 A1 | 8/2019 | Olivo |
| 2021/0023004 A1 | 1/2021 | Kikuchi et al. |
| 2021/0023047 A1 | 1/2021 | Semba et al. |
| 2021/0177802 A1 | 6/2021 | Semba et al. |
| 2022/0117933 A1 | 4/2022 | Semba et al. |
| 2022/0389110 A1 | 12/2022 | Jure-Kunkel et al. |

FOREIGN PATENT DOCUMENTS

| | | |
|---|---|---|
| CN | 101209243 A | 7/2008 |
| CN | 103562406 A | 2/2014 |
| CN | 105640935 A | 6/2016 |
| CN | 107207580 A | 9/2017 |
| CN | 107810013 A | 3/2018 |
| EP | 1332755 A1 | 8/2003 |
| EP | 1921086 A1 | 5/2008 |
| EP | 2123260 A1 | 11/2009 |
| EP | 2415464 A1 | 2/2012 |
| JP | 7-501813 A | 2/1995 |
| JP | 8-509230 A | 10/1996 |
| JP | 2002-518384 A | 6/2002 |
| JP | 2004-516247 A | 6/2004 |
| JP | 2005-509000 A | 4/2005 |
| JP | 2006-513189 A | 4/2006 |
| JP | 2006-340714 A2 | 12/2006 |
| JP | 2010-514708 A | 5/2010 |
| JP | 5551683 B2 | 5/2014 |
| JP | 2018-508516 A | 3/2018 |
| RU | 2405601 | 12/2010 |
| RU | 2476216 C1 | 2/2013 |
| WO | WO 93/11757 A1 | 6/1993 |
| WO | WO 94/23697 A1 | 10/1994 |
| WO | WO 99/65894 A1 | 12/1999 |
| WO | WO 02/032399 | 4/2002 |
| WO | WO 2002/032399 A1 | 4/2002 |
| WO | WO 03/041681 A2 | 5/2003 |
| WO | WO 2004/004771 A1 | 1/2004 |
| WO | WO 2004/056875 A1 | 7/2004 |
| WO | WO 2004/058140 A2 | 7/2004 |
| WO | WO 2004/072286 A1 | 8/2004 |
| WO | WO 2005/046643 A2 | 5/2005 |
| WO | WO 2005/118565 A1 | 12/2005 |
| WO | WO 2006/037230 A1 | 4/2006 |
| WO | WO 2007/026869 A1 | 3/2007 |
| WO | WO 2007/061874 A2 | 5/2007 |
| WO | WO 2008/080367 A1 | 7/2008 |
| WO | WO-2008156712 A1 | 12/2008 |
| WO | WO 2010/027827 A2 | 3/2010 |
| WO | WO 2010/077634 A1 | 7/2010 |
| WO | WO 2010/113983 A1 | 10/2010 |
| WO | WO 2010/113984 A1 | 10/2010 |
| WO | WO 2011/066342 A2 | 6/2011 |
| WO | WO 2011/094339 A1 | 8/2011 |
| WO | WO-2012119077 A1 | 9/2012 |
| WO | WO 2012/135408 A1 | 10/2012 |
| WO | WO 2013/019906 A9 | 2/2013 |
| WO | WO-2014087230 A1 | 6/2014 |
| WO | WO-2014159562 A1 | 10/2014 |
| WO | WO 2014/193898 A1 | 12/2014 |
| WO | WO 2014/208774 A1 | 12/2014 |
| WO | WO-2014199294 A1 | 12/2014 |
| WO | WO-2015112900 A1 | 7/2015 |
| WO | WO 2015/134399 A1 | 9/2015 |
| WO | WO-2015134605 A1 | 9/2015 |
| WO | WO 2015/184145 A1 | 12/2015 |
| WO | WO-2015183961 A1 | 12/2015 |
| WO | WO-2016130839 A1 | 8/2016 |
| WO | WO 2016/141209 A1 | 9/2016 |
| WO | WO 2017/188350 A1 | 11/2017 |
| WO | WO 2018/071792 A | 4/2018 |

OTHER PUBLICATIONS

Maurer-Spurej et al. Factors Influencing Uptake and Retention of Amino-Containing Drugs in Large Unilamellar Vesicles Exhibiting Transmembrane pH gradients. Biochmica et Biophysica Acta, 1999. 1416:1-10.*

Ishida et al. Targeted Delivery And Triggered Release of Liposomal Doxorubicin Enhances Cytotoxicity Against Human B Lymphoma Cells. Biochimica et Biophysics Acta, 2001. 1515:144-158.*

Haran et al. Transmembrane Ammonium Sulfate Gradients in Liposomes Produce Efficient and Stable Entrapment of Amphipathic Weak Bases. Biochemica et Biophysics Acta, 1993. 1151:201-215.*

Notice of Final Rejection for Korean Patent Application No. 10-2011-7022860, Korean Intellectual Property Office, Daejeon, Republic of Korea, dated Sep. 23, 2014.

Office Action dated Sep. 29, 2014 for Peruvian application No. 001735-2011/DIN, INDECOPI, Lima, Peru.

Applicant Eisai R&D Management Co., Ltd. "Memorandum in Response to Official Action dated Aug. 4, 2014," filed with the Israel Patent Office on Dec. 2, 2014, for Israel Patent Application No. 215059.

Eisai R&D Management Co., Ltd. Response filed Dec. 24, 2014, in reply to the Notice of Final Rejection dated Sep. 23, 2014, for KR Patent Appl. No. 10-2011-7022860.

Notice of Allowance dated Jan. 9, 2015 for KR Patent Appl. No. 10-2011-7022860, Korean Intellectual Property Office, Daejeon, Republic of Korea.

Notice of the Result of Substantive Examination Pursuant to Article 52 (1) of Patent Law No. 14/2001, dated Nov. 29, 2013 for Indonesian application No. W-00 2011 03470, Ministry of Law and Human Rights of the Republic of Indonesia, Tangerang, Indonesia.

Eisai R&D Management Co., Ltd. Response filed with the Mexican Institute of Industrial Property on Sep. 18, 2013 for Mexican application No. MX/a/2011/009632.

Eisai R&D Management Co., Ltd. Response filed with the Canadian Intellectual Property Office on Jan. 16, 2014 for Canadian application No. 2,756,811.

Opposition issued by the National Institute of Industrial Property dated Jan. 16, 2014 for Chilean application No. 2444-2011, Santiago, Chili.

Eisai R&D Management Co., Ltd. Response filed with the National Office of Intellectual Property, on Dec. 13, 2013 for Vietnamese application No. 1-2011-02950.

Office Action dated Jan. 9, 2014 for Peruvian application No. 001735-2011/DIN, INDECOPI, Lima, Peru.

Eisai R&D Management Co., Ltd. Response filed with the Superintendencia de Industria y Comercio on Dec. 2, 2013 for Colombian application No. 11-130828-00010-000.

Eisai R&D Management Co., Ltd. Response filed with INDECOPI, on Jan. 20, 2014 for Peruvian application No. 001735-2011/DIN.

Eisai R&D Management Co., Ltd. Response, "Observations (OA2)" filed with the State Intellectual Property Office of the Peoples' Republic of China (SIPO) on Dec. 23, 2013 for Chinese application No. 201080014698.2.

Communication pursuant to Article 94(3) EPC, dated Jan. 24, 2014 for European application No. 10 758 754.5, European Patent Office, Munich Germany.

Notice of Allowance issued by the Superintendencia de Industria y Comercio dated Jan. 21, 2014 for Colombian application No. 11-130828.

Notice of Reasons for Rejection, dated Feb. 6, 2014 for Japanese application No. 2011-507240, Japan Patent Office, Tokyo, Japan.

Eisai R&D Management Co., Ltd. Response filed with the Intellectual Property Office of New Zealand on Feb. 7, 2014 for New Zealand application No. 595212.

(56) References Cited

OTHER PUBLICATIONS

Eisai R&D Management Co., Ltd. Response filed with the Korean Intellectual Property Office on Jan. 22, 2014 for Korean application No. 10-2011-7022860.
Non-final Office action for U.S. Appl. No. 13/260,864, dated Mar. 10, 2014, United States Patent and Trademark Office, Alexandria, VA.
Petition of Eisai R&D Management Co., Ltd., for Japanese Patent Application No. 2014-092382, filed with the Japanese Patent Office, Tokyo, Japan, on Dec. 26, 2014.
Notice of Reasons for Rejection, for Japanese Patent Application No. 2014-092382, dated Jan. 28, 2015, by the Japanese Patent Office, Tokyo, Japan.
Examiner's Report Issued on Patent of Invention Application for Chilean Patent Application No. 2444-2011, by the National Institute of Industrial Property, Santiago, Chili, dated Jan. 21, 2015.
Kim, S. et al., "Multivesicular liposomes containing cytarabine entrapped in the presence of hydrochloric acid for intracavitary chemotherapy," Cancer Treatment Reports 71:705-711, Jul./Aug. 1987, National Cancer Institute, Silver Spring, MD.
Kim, S. et al., "Preparation of Multivesicular liposomes," Biochim. Biophys. Acta 728:339-348 (1983), Elsevier Biomedical Press, Amsterdam, Netherlands.
Amendment and Reply under 37 C.F.R. § 1.114 to Accompany the Filing of a Request for Continued Examination, filed Mar. 23, 2015, for U.S. Appl. No. 13/260,864, filed with the United States Patent and Trademark Office, Alexandria, VA.
Communication pursuant to Article 94(3) EPC, dated Jan. 24, 2014 for European application No. 10 758 755.2, European Patent Office, Munich, Germany.
Notice of Allowance regarding Canadian Patent Application No. 2,756,811, dated Feb. 10, 2014, Canadian Intellectual Property Office, Toronto, Ontario, Canada.
Further Examination Report Acceptance for New Zealand patent application No. 595212, dated Feb. 25, 2014, New Zealand Intellectual Property Office, Wellington, New Zealand.
Communication regarding novelty examination for Mexican patent application No. MX/a/2011/009632, dated Jan. 17, 2014, Mexican Institute of Industrial Property, Cuauhtémoc, Distrito Federal, Mexico.
Notice of Reasons for Rejection, dated Feb. 27, 2014 for Japanese application No. 2011-507239, Japan Patent Office, Tokyo, Japan.
Response filed with the Industrial Property Institute on Mar. 11, 2014 for Chilean application No. 2444-2011.
Response to the Result of Substantive Examination Stage I on Indonesian Patent Application No. W-00 2011 03470 on Mar. 25, 2014.
Decision to Grant a Patent, for Japanese Patent Application No. JP2011-507240, Japanese Patent Office, dated May 7, 2014.
Notice of Preliminary Rejection, for Korean Patent Application No. 10-2011-7022860, Korean Intellectual Property Office, Daejeon, Republic of Korea, dated May 20, 2014.
"Notification of Third Office Action," for Chinese Patent Appl. No. 201080014698.2, dated Mar. 28, 2014, The State Intellectual Property Office of the People's Republic of China, Beijing, China.
Applicants' response filed Apr. 7, 2014, to the Feb. 6, 2014 office action from the Japanese Patent Office issued for Japanese Patent Appl. No. 2011-507240.
Eisai R&D Management Co., Ltd. Response and Amendment filed Jul. 18, 2014, in reply to the Korean office action dated May 20, 2014 for KR Patent Appl. No. 10-2011-7022860.
Eisai R&D Management Co., Ltd. Response filed Jun. 17, 2014, in reply to the Mexican office action (Official Communication No. 4069) for MX Patent Appl. No. MX/a/2011/009632.
Notice of Allowance dated Aug. 6, 2014 for Chinese Patent Application No. 201080014698.2, The People's Republic of China State Intellectual Property Office, Beijing, China.
Office action dated Aug. 4, 104 for Israel Patent Appl. No. 215059, Israel Patent Office, Jerusalem, Israel.

Eisai R&D Management Co., Ltd. amendment (filed May 20, 2015) and argument (filed May 21, 2015) with INDECOPI, for Peruvian application No. 001735-2011/DIN.
Notification: Resolution No. 000089-2015/CIN-INDECOPI issued Jul. 16, 2015, for Peruvian patent appl. No. 001735-2011 DIN, by the National Institute for the Defense of Competition and Protection of Intellectual Property (INDECOPI), Lima, Peru.
Applicant Eisai R&D Management Co., Ltd.'s Response filed Jul. 24, 2015 for Philippines patent application No. 1/2011/501838, Intellectual Property Office of the Philippines, Taguig City, Philippines.
Non-final Office action for U.S. Appl. No. 13/260,864, dated Jul. 13, 2015, United States Patent and Trademark Office, Alexandria, VA.
Opposition filed against Peru Patent Appl. No. 001735-2011/DIN by Farmindustria S.A. de Perú.
Preliminary amendment for Japanese Patent Application No. 2014-092382, filed with the Japanese Patent Office, Tokyo, Japan, dated May 28, 2014 by the applicant, Eisai R&D Management Co., Ltd.
Amendment and argument in reply to the office action dated Jan. 28, 2015, for Japanese Patent Application No. 2014-092382, filed with the Japanese Patent Office, Tokyo, Japan, on Mar. 27, 2015 by the applicant, Eisai R&D Management Co., Ltd.
Supplemental Amendment and Statement of Substance of Interview, filed May 27, 2015, for U.S. Appl. No. 13/260,864, filed with the United States Patent and Trademark Office, Alexandria, VA, and Applicant-Initiated Interview Summary Form PTOL-413 dated Apr. 27, 2015, by the United States Patent and Trademark Office, Alexandria, VA.
Decision to Grant a Patent, for Japanese Patent Application No. JP2014-092382, Japanese Patent Office, dated Jun. 2, 2015.
Subsequent Substantive Examination Report, for Philippines Patent Appl. No. 1/2011/501838, dated Jun. 4, 2015, The Intellectual Property Office of the Philippines, Taguig City, Philippines.
Eisai &D Management Co., Ltd. Response filed Apr. 16, 2015 to the Jan. 21, 2015 office action, for Chilean application No. 2444-2011, filed at the National Institute of Industrial Property, Santiago, Chili.
Eisai R&D Management Co., Ltd. Response filed with INDECOPI, on May 20, 2015 for Peruvian application No. 001735-2011/DIN.
Eisai R&D Management Co., Ltd. Supplemental Response filed on Jun. 5, 2015 Chilean application No. 2444-2011, filed at the National Institute of Industrial Property, Santiago, Chili.
Eisai R&D Management Co., Ltd., Argument and Amendment filed Apr. 28, 2014, in reply to the Feb. 25, 2014 (dated Feb. 27, 2014) office action from the Japanese Patent Office issued for Japanese Patent Appl. No. 2011-507239.
Final Office action for U.S. Appl. No. 13/260,864, dated Sep. 26, 2014, United States Patent and Trademark Office, Alexandria, VA.
Eisai R&D Management Co., Ltd. Response filed with INDECOPI on Oct. 27, 2014, in reply to the Sep. 29, 2014 office action for Peruvian Patent Appl. No. 001735-2011/DIN.
International Search Report (ISR) for PCT/JP2010/055770, I.A. fd: Mar. 30, 2010, dated Jun. 1, 2010 from the Japanese Patent Office, Tokyo, Japan.
International Preliminary Report on Patentability (IPRP), Chapter I of the Patent Cooperation Treaty, including the Written Opinion for PCT/JP2010/055770, I.A. fd: Mar. 30, 2010, dated Nov. 15, 2011, from the International Bureau of WIPO, Geneva, Switzerland.
Arima, H et al., "Enhancement of antitumor effect of doxorubicin by its complexation with gamma-cyclodextrin in pegylated liposomes," J Drug Target 14(4): 225-232 (May 2006), Informa Healthcare, London, England.
DesJardins, C et al., "A high-performance liquid chromatography-tandem mass spectrometry method for the clinical combination study of carboplatin and anti-tumor agent eribulin mesylate (E7389) in human plasma," J Chromatogr B Analyt Technol Biomed Life Sci; 875(2):373-382 (Nov. 2008), Elsevier, New York.
Dos Santos, N et al., "pH gradient loading of anthracyclines into cholesterol-free liposomes: enhancing drug loading rates through use of ethanol," Biochim Biophys Acta 1661(1): 47-60 (Feb. 2004), Elsevier, Amsterdam, Netherlands.
Fatouros, DG et al., "Liposomes encapsulating prednisolone and prednisolone-cyclodextrin complexes: comparison of membrane

(56) References Cited

OTHER PUBLICATIONS integrity and drug release," Eur J Pharm Sci 13(3): 287-296 (Jun. 2001), Elsevier, Amsterdam, Netherlands.
Hagiwara, Y et al., "Preparation and pharmaceutical evaluation of liposomes entrapping salicylic acid/gamma-cyclodextrin conjugate," Chem Pharm Bull (Tokyo) 54(1): 26-32 (Jan. 2006), Pharmaceutical Society of Japan, Tokyo, Japan.
Jordan, MA et al., "The primary antimitotic mechanism of action of the synthetic halichondrin E7389 is suppression of microtubule growth," Mol Cancer Ther 4: 1086-1095 (Jul. 2005), Am. Assoc Cancer Research, Philadelphia, PA.
Maestrelli, F et al., "Effect of preparation technique on the properties of liposomes encapsulating ketoprofen-cyclodextrin complexes aimed for transdermal delivery," Int J Pharm 312(1-2): 53-60 (Apr. 2006), Elsevier, Amsterdam, Netherlands.
Mayer, LD et al., "Uptake of adriamycin into large unilamellar vesicles in response to a pH gradient," Biochim Biophys Acta, 857(1): 123-126 (May 1986), Elsevier, Amsterdam, Netherlands.
Matsumura, Y et al., "A New Concept for Macromolecular Therapeutics in Cancer Chemotherapy: Mechanism of Tumoritropic Accumulation of Proteins and the Antitumor Agent Smancs," Cancer Res 46: 6387-6392 (Dec. 1986), Am. Assoc. Cancer Research, Baltimore, MD.
Okouneva, T et al., "Inhibition of centromere dynamics by eribulin (E7389) during mitotic metaphase," Mol Cancer Ther 7: 2003-2011 (Jul. 2008), Am. Assoc Cancer Research, Philadelphia, PA.
Piel, G et al., "Betamethasone-in-cyclodextrin-in-liposome: the effect of cyclodextrins on encapsulation efficiency and release kinetics," Int J Pharm 312(1-2): 75-82 (Apr. 2006), Elsevier, Amsterdam, Netherlands.
Wang, Y, "Eribulin mesilate—Antimitotic drug tubulin polymerization inhibitor oncolytic," Drugs of the Future 32(8): 681-698 (Aug. 2007), Thomson Reuters, New York.
International Search Report (ISR) for PCT/JP2010/055769, I.A. fd: Mar. 30, 2010, dated Jun. 8, 2010 from the Japanese Patent Office, Tokyo, Japan.
International Preliminary Report on Patentability (IPRP), Chapter I of the Patent Cooperation Treaty, including the Written Opinion for PCT/JP2010/055769, I.A. fd: Mar. 30, 2010, dated Nov. 15, 2011, from the International Bureau of WIPO, Geneva, Switzerland.
Russian Office action for RU Application No. 2011139715/20(059371), dated Nov. 28, 2011, its partial English translation and Applicant's response filed Jan. 30, 2012.
Examiner's first report for AU patent application No. 2010232347, dated May 11, 2012, IP Australia, Woden, Australia.
Office action for Taiwanese patent application No. 099109838, dated Jun. 22, 2012, Taiwan Intellectual Property Office, Taipei, Taiwan.
Satsuka, Y. Section 2 in "Recent Evolution of Liposome Application—Toward Development of Artificial Cells." pp. 33-37 (2005), N. Oku et al., eds., NTS Inc, Publisher, Tokyo, Japan.
Kikuchi, H. et al., "Liposome I—Method of Preparing and Testing," Cell Engineering, 2(9):1136-1149 (1983), Japan.
Examiner's report for New Zealand patent application No. 595212, dated Aug. 14, 2012, New Zealand Intellectual Property Office, Wellington, New Zealand.
Communication regarding novelty examination for Mexican patent application No. MX/a/2011/009632, dated Aug. 7, 2012, Mexican Institute of Intellectual Property, Cuauhtémoc, Distrito Federal, Mexico.
Extended European Search Report for European patent application No. 10758754.5, dated Oct. 8, 2012, European Patent Office, Munich, Germany.
Loftsson et al., "Solubilization and Stabilization of Drugs Through Cyclodextrin Complexation."Acta Pharmaceutica Nordica, 3(4): 215-217 (1991), American Pharmaceutical Association, Easton, PA.
Haran et al., "Transmembrane ammonium sulfate gradients in liposomes produce efficient and stable entrapment of amphipathic weak bases." Biochim Biophys Acta., 1151(2):201-215 (1993), Elsevier Pub. Co., Amsterdam, Netherlands.

Extended European Search Report for European patent application No. 10758755.2, dated Oct. 31, 2012, European Patent Office, Munich, Germany.
FormuMax Scientific, Inc., "Doxoves-Liposome Doxorubicin Compared to Doxil®," (1995), downloaded from the internet: www.liposomeexpert.com/categories/Drug-Loaded-Liposomes (accessed Nov. 8, 2012).
Bolotin et al., "Ammonium sulfite gradients for efficient and stable remote loading of amphipathic weak bases into liposomes and ligandoliposomes." J. Liposome Res. 4(1):455-479 (1994), Marcel Dekker, Inc., New York, NY.
Decision on Grant of Russian patent application No. 2011139715, dated Sep. 25, 2012, Russian Agency for Patent and Trademarks, Moscow, Russia.
Opposition to Colombian patent application No. 11-130828, by Laboratorios Synthesis S.A.S., published Apr. 30, 2012 in the Colombia Industrial Property Gazette No. 643, Superintendence of Industry and Trade, Bogota, Colombia.
Notification of the First Office Action, Chinese patent application No. 201080014698.2, dated Oct. 24, 2012, The State Intellectual Property Office of the People's Republic of China, Beijing, China.
Fude, ed., in "Liposomes," CUI, $5^{th}$ edition, People's Press of Hygiene, Mar. 2004, pp. 386-394, China.
Opposition to Peruvian patent application No. 001735-2011/DIN, by Farmindustria S.A., dated Nov. 23, 2012, National Institute for the Defense of Competition and Protection of Intellectual Property (INDECOPI), Lima, Peru.
Canadian Office Action regarding Canadian Patent Application No. 2,756,811, dated Dec. 19, 2012, Canadian Intellectual Property Office, Toronto, Ontario, Canada.
Notice of Preliminary Rejection for Korean patent application No. 10-2011-7022860, dated Dec. 28, 2012, Korean Intellectual Property Office, Daejeon, Republic of Korea.
Corrected written opinion for Extended European Search Report, dated Dec. 19, 2012, for European patent application No. 10758755.2, European Patent Office, Munich, Germany.
Eisai R&D Management Co., Ltd. Response, filed Jan. 14, 2013, to the Columbian Opposition dated Jul. 25, 2012, for Columbian Application No. 11-130828.
Mexican Response filed on Jan. 7, 2013, to the Mexican Office Action dated Aug. 7, 2012, for Mexican Application No. MX/a/2011/0009632.
Yu, Y et al., "Characterization of the pharmacokinetics of a liposomal formulation of eribulin mesylate (E7389) in mice," Int. J. Pharmaceutics 443:9-16 (Feb. 2013), Elsevier, Amsterdam, Netherlands.
Response filed Jan. 21, 2013, to the Peruvian Opposition issued Nov. 23, 2012, for Peruvian Patent Application No. 001735-2011/DIN.
Response filed Dec. 27, 2012, to the Taiwan office action dated Jun. 22, 2012 for TW Patent Appl. No. 099109838.
Package Insert for "Halaven®, 1 mg," Jul. 2011, Eisai Co., Ltd., Tokyo, Japan.
Package Insert for "Novantron® Injection 10mg, 20mg," Nov. 2011, ASKA Pharmaceutical Co., Ltd., Tokyo, Japan.
"Approval Decision Letter from the Intellectual Property Office" dated Jan. 23, 2013, for TW Patent Appl. No. 099109838, Intellectual Property Office, Ministry of Economic Affairs, R.O.C., Taipei, Taiwan.
Kuznetsov, G. et al., "Antiproliferative effects of halichondrin B analog eribulin mesylate (E7389) against paclitaxel-resistant human cancer cells in vitro," Abstract C58, AACR-NCI-EORTC International Conference: Molecular Targets and Cancer Therapeutics, Oct. 22-26, 2007, San Francisco, CA.
NORMOSOL®-R packaging insert; downloaded from http://whatsthedose.com/spl/0409-7670.html on Jul. 20, 2012, revised Oct. 2006, Hospira, Inc.
Non-final Office action for U.S. Appl. No. 13/260,872, dated Aug. 1, 2012, United States Patent and Trademark Office, Alexandria, VA.
"Amendment and Reply under 37 C.F.R. § 1.111," including two exhibits, filed Feb. 1, 2013, for U.S. Appl. No. 13/260,872.

(56) References Cited

OTHER PUBLICATIONS

Final Office Action for U.S. Appl. No. 13/260,872, dated Apr. 24, 2013, The United States Patent and Trademark Office, Alexandria, VA.
Response filed Feb. 28, 2013, to the Korean office action dated Dec. 28, 2012 for KR Patent Appl. No. 10-2011-7022860.
Package insert, including a translation of the header and sections entitled: "Storage," "Expiration date," "Structural formula" and "Physiochemical properties," for Halaven® Intravenous Injection 1 mg, (Eribulin mesylate preparation), Jul. 2011, $2^{nd}$ edition, Eisai Co., Ltd., Tokyo, Japan.
Header and sections III.1.(2) "Solubility"; (5) "Acid/Base Dissociation Constant" and (6) "Partition Coefficient" of the Pharmaceutical Interview Form (IF) for Halaven® Intravenous Injection 1 mg, (Eribulin mesylate preparation), Jul. 2011 ($2^{nd}$ Edition) Eisai Co., Ltd., Tokyo, Japan.
Pharmaceutical Interview Form (IF) for Halaven® Intravenous injection, 1 mg, (Eribulin mesylate preparation), Jul. 2011, ($2^{nd}$ Edition) Eisai Co., Ltd., Tokyo, Japan.
Package insert, including a translation of the header and sections entitled: "Storage," "Expiration date," Precautions, "Structural formula," and "Properties," for Novantron® Injection 10mg, "Novantron® Injection 20mg," (Mitoxantrone hydrochloride injection), Nov. 2011, ASKA Pharmaceutical Co., Ltd., Tokyo, Japan.
Sections III.1.(2), (5) and (6) of the Pharmaceutical Interview Form (IF) for Pharmaceutical Interview Form (IF) for Adriacin® Injection 10 and for Adriacin® Injection 50, (Doxorubicin hydrochloride for injection), Aug. 2011, ($16^{nd}$ Edition), Kyowa Hakko Kirin Co., Ltd., Japan.
Pharmaceutical Interview Form (IF) for Adriacin® Injection 10 and for Adriacin® Injection 50, (Doxorubicin hydrochloride for injection), Aug. 2011, ($16^{nd}$ Edition), Kyowa Hakko Kirin Co., Ltd., Japan.
Applicant's "Observations" filed Apr. 2, 2013, in response to the first Chinese office action for CN Patent Appl. No. 201080014698.2.
"Oncovin® for injection 1 mg—Vincristine Sulfate Preparation," Package Insert, including a translation of the header and sections entitled: "Structural formula" and "Properties," Nippon Kayaku Co., Ltd., revision of Aug. 2009.
"Rozeus® Intravenous Solution 10 mg—Rozeus® Intravenous Solution 40 mg—Vinorelbine Ditartrate Intravenous Solution," Package Insert, including a translation of the header and sections entitled: "Structural formula" and "Properties," Nippon Kayaku Co., Ltd., revision of Nov. 2009.
"Exal® for Injection 10 mg—Japanese Pharmacopeia (JP) Vinblastine Sulfate for Injection," including a translation of the header and sections entitled: "Structural formula" and "Properties," Nippon Kayaku Co., Ltd., Package Insert, revision of Jul. 2011.
"Adriacin® Injection 10—Adriacin® Injection 50," Package Insert, including a translation of the header and sections entitled: "Structural formula" and "Solubility," revision of Aug. 2011.
"Preliminary Conclusion (On non-Patentability)" for UA Patent Application No. a201111426, State Service of Intellectual Property of Ukraine, Apr. 8, 2013.
"Substantive Examination Adverse Report (Section 30(1)/30(2))," for Malaysian Patent Application No. PI 201 1004382, dated Apr. 15, 2013, Intellectual Property Corporation of Malaysia, Kuala Lumpar, Malaysia.
Applicant's response filed May 3, 2013 to the Communication Pursuant to Rules 70(2) and 70a(2) EPC dated Oct. 25, 2012 for EP Application No. 10 758 754.5.
Applicant's response filed May 29, 2013, to the Communication Pursuant to Rules 70(2) and 70a(2) EPC dated Nov. 19, 2012 for EP Application No. 10 758 755.2.
Response filed Jun. 19, 2013, to the Office Action dated Dec. 19, 2012, for Canadian patent application No. 2,756,811, by Applicant Eisai R&D Management Co., Ltd., in the Canadian Intellectual Property Office, Gatineau, Québec, Canada.

Requisition by the Examiner in Accordance with Subsection 30(2) of the Patent Rules, dated Jul. 17, 2013, for Canadian patent application No. 2,756,811, the Canadian Intellectual Property Office, Gatineau, Québec, Canada.
Response filed Jun. 14, 2013, to the Substantive Examination Adverse Report dated Apr. 15, 2013, for Malaysian patent application No. PI 2011004382, by Applicant Eisai R&D Management Co., Ltd., in the Intellectual Property Corporation of Malaysia, Kuala Lumpur, Malaysia.
$2^{nd}$ Office action—Subject Matter: Communication Regarding Novelty Examination, dated Apr. 22, 2013, for Mexican patent application No. MX/a/2011/009632, Mexican Institute of Industrial Property, Mexico.
Response on Preliminary Conclusion on Non-patentability, filed Jun. 11, 2013, for Ukrainian patent application No. a201111426, in the Ukrainian Institute of Industrial Property, Kyiv, Ukraine.
Notice of Allowance, dated Jul. 23, 2013, for Ukrainian patent application No. a201111426, the Ukrainian Institute of Industrial Property, Kyiv, Ukraine.
Notice of Preliminary Rejection, dated Jul. 22, 2013, for Korean patent application No. 10-2011-7022860, the Korean Intellectual Property Office, Daejeon, Republic of Korea.
Examiner's Report Issued on Patent of Invention Application, dated Jul. 11, 2013, for Chilian patent application No. 2444-2011, National Institute of Industrial Property, Santiago, Chili.
Substantive Examination Report, dated Aug. 8, 2013, for Philippines patent application No. 1/2011/501838, Intellectual Property Office of the Philippines, Taguig City, Philippines.
Office action dated Aug. 8, 2013, for Colombian patent application No. 11-130828, Superintendent of Industry and Trade, Bogotá, Columbia.
Notification on the Result of Substantive Examination, for Vietnamese patent application No. 1-2011-02950, dated Aug. 16, 2013, National Office of Intellectual Property, Hanoi, Vietnam.
Notification of the Second Office Action, dated Aug. 8, 2013, for Chinese patent application No. 201080014698.2, The State Intellectual Property Office of the People's Republic of China, Beijing, China.
Peleg-Shulman, T et al., "Characterization of sterically stabilized cisplatin liposomes by nuclear magnetic resonance," Biochim Biophys Acta, Feb. 2001; 1510(1-2): 278-291, Elsevier, Amsterdam, Netherlands.
Drummond, D.C. et al., "Optimizing Liposomes for Delivery of Chemotherapy Agents to Solid Tumors," Pharmacological Reviews 51(4):691-743 (1999), The American Society for Pharmacology and Experimental Therapeutics, United States.
Response filed Sep. 30, 2013, to Paper No. 7 mailed Aug. 8, 2013, for Philippine patent application No. 1-2011-501838, by Applicant Eisai R&D Management Co., Ltd., in the Intellectual Property Office of the Philippines, Taguig City, Philippines.
Applicant Eisai R&D Management Co., Ltd.'s Response filed Nov. 11, 2014, submitting English translation of JP 5551683 B2, in reply to Paper No. 9 mailed Sep. 17, 2014, for Philippine patent application No. 1-2011-501838, filed with the Intellectual Property Office of the Philippines, Taguig City, Philippines.
Subsequent Substantive Examination Report, dated Sep. 17, 2014, for Philippines patent application No. 1/2011/501838, Intellectual Property Office of the Philippines, Taguig City, Philippines.
"Decision to Grant a Patent," dated Aug. 27, 2014, for Japanese Patent Appl. No. 2011-507239, the Japanese Patent Office, Tokyo, Japan.
"Amendment and Reply under 37 C.F.R. § 1.111," filed Sep. 9, 2014, for U.S. Appl. No. 13/260,864, submitted to the United States Patent and Trademark Office, Alexandria, VA.
Corrected Translation: Notice of Allowance dated Jan. 9, 2015 for KR Patent Appl. No. 10-2011-7022860, Korean Intellectual Property Office, Daejeon, Republic of Korea.
Eisai R&D Management Co., Ltd. response filed Dec. 22, 2015, with IP Australia, for Australian patent application No. 2014200717.
Notice before Allowance of Israel Patent Application No. 215059, dated Nov. 25, 2015, The Israel Patent Office.

(56) References Cited

OTHER PUBLICATIONS

Supreme Resolution for Peruvian Patent Application No. 001735-2011DIN, dated Nov. 30, 2015, Instituto Nacional de Defensa de la Competencia y de la Protección de la Propiedad Intelectual, Lima, Peru.
Examiner's Report Issued on Patent of Invention Patent Application, dated Dec. 18, 2015 for Chilian patent application No. 2444-2011, National Institute of Industrial Property, Santiago, Chili.
"Filed Notice of Opposition" for Peruvian Patent Application No. 001798-2015, dated Jan. 25, 2016, National Institute for the Defense of Competition and Protection of Intellectual Property (INDECOPI), Lima, Peru.
Amendment and Reply Under 37 C.F.R. § 1.114 to the Nov. 20, 2015 final Office action, filed Mar. 9, 2016, for U.S. Appl. No. 13/260,864.
Communication under Rule 71(3) EPC: Intention to grant, for EP patent application No. EP 10 758 755.2, dated Feb. 25, 2016, The European Patent Office, Munich, Germany.
Final rejection for Algerian Patent Appl. No. 110640, dated Aug. 18, 2013, by the Institut National Algérien de la Propriété Industrielle, partial translation.
Eisai R&D Management Co., Ltd., response filed Aug. 29, 2016, in reply to the office action for Algerian Patent Appl. No. 110640, partial translation.
Substantive Examination Clear Report—Section 30(1)/30(2) for Malaysian Patent Appl. No. PI 2011004382, dated Sep. 30, 2016, by the Intellectual Property Corporation of Malaysia.
Amendment and Reply Under 37 C.F.R. § 1.111 to the Jun. 27, 2016 Office action, filed Dec. 22, 2016, for U.S. Appl. No. 13/260,864.
Voluntary amendment filed Jul. 7, 2016 for Cambodian Patent Application No. KH/P/10/00097.
Transmittal letter and office action entitled "Technical Report on the Application No. PCT 1637/2011," issued by The Egyptian Patent Office, Jan. 3, 2017, for Egyptian Patent Appl. No. PCT 1637/2011, Cairo, Egypt.
Examination report under sections 12 & 13 of the Patents Act, 1970 and the Patents Rules, 2003, for Indian Patent Application No. 6850/DELNP/2011, dated Nov. 10, 2016, The Patent Office, Intellectual Property India.
Communication under Rule 71(3) EPC: Intent to grant, for European Patent Application No. 10 758 754.5, dated Jan. 19, 2017, European Patent Office, Munich Germany.
Final Office action for U.S. Appl. No. 13/260,864, dated Feb. 3, 2017, United States Patent and Trademark Office, Alexandria, VA.
Official notice: Intention to grant patent and invitation to pay fees for grant for Vietnamese patent application No. 1-2011-02950, dated Jan. 24, 2017, National Office of Intellectual Property, Hanoi, Vietnam.
Eisai R&D Management Co., Ltd. Response filed Mar. 30, 2017 at the Egyptian Patent Office, Cairo, Egypt, against the Office Decision dated Jan. 3, 2017, for Egyptian Patent Application No. PCT 1637/2011.
Patent Examination Report No. 1, for AU patent application No. 2014200717, dated Aug. 14, 2015, by IP Australia, Woden ACT, Australia.
Completion of Final Requirements, dated Aug. 27, 2015 by the Intellectual Property Office of the Philippines, for Philippines patent application No. 1/2011/501838, Taguig City, Philippines.
Final Office action for U.S. Appl. No. 13/260,864, dated Nov. 20, 2015 by the United States Patent and Trademark Office, Alexandria, VA, and Applicant's Amendment and Reply to the Jul. 13, 2015 non-final Office action, filed Oct. 14, 2015, for U.S. Appl. No. 13/260,864, filed with the United States Patent and Trademark Office, Alexandria, VA.
Eisai R&D Management Co., Ltd. Appeal filed Aug. 12, 2015, with INDECOPI, for Peruvian application No. 001735-2011/DIN.
Eisai R&D Management Co., Ltd.'s Response filed Sep. 18, 2015, to the Aug. 27, 2015 office action for Philippines patent application No. 1-2011-501838.
Transmittal letter and office action entitled "Technical Report on the Application No. PCT 1637/2011," from The Egyptian Patent Office, dated Jan. 14, 2016, for Egyptian Patent Appl. No. PCT 1637/2011, Cairo, Egypt.
Notice of Acceptance for AU Patent Appl. No. 2014200717 dated Feb. 13, 2016, IP Australia.
Office action for Vietnamese Patent Appl. No. 1-2011-02950, dated Mar. 31, 2016, Ministry of Science & Technology, Vietnam.
Eisai R&D Management Co., Ltd. response filed Mar. 14, 2016 to the office action dated Dec. 11, 2015, for Chilean Patent Appl. No. 2444-2011.
Eisai R&D Management Co., Ltd. response filed Apr. 18, 2016, to "Technical Report on the Application No. PCT 1637/2011," filed at the Egyptian Patent Office, Cairo, Egypt, for Egyptian Patent Appl. No. PCT 1637/2011.
Eisai R&D Management Co., Ltd Response filed on May 30, 3016 to the Mar. 31, 2016 Vietnamese office action for Vietnamese Patent Appl. No. 1-2011-02950.
Eisai R&D Management Ltd. Response to Opposition, response filed Apr. 28, 2016 for Peruvian Patent Appl. No. 1798-2015.
Non-final Office action for U.S. Appl. No. 13/260,864, dated Jun. 27, 2016, United States Patent and Trademark Office, Alexandria, VA.
Notice of Allowance dated Apr. 20, 2017, for Indonesian Patent Appl. No. W00201103470, Department of Justice and Human Right of the Republic of Indonesia, Jakarta, Indonesia.
Request for Continued Examination, Declaration under 37 C.F.R. § 1.132, and Reply Under 37 C.F.R. § 1.114 to the Feb. 3, 2017 Office action, filed Aug. 1, 2017, for U.S. Appl. No. 13/260,864.
Hearing Notice in Reference of Indian Application No. 6850/DELNP/2011, dispatched Aug. 17, 2017, from The Patent Office, Intellectual Property India.
Response and Amendment to Result for Hearing Notice, filed Oct. 3, 2017, for Indian Patent Application No. 6850/DELNP/2011, with Intellectual Property India listing dated Mar. 10, 2017 showing entry number for Form 30 for Indian Patent Application No. 6850/DELNP/2011.
Excerpted file history of U.S. Appl. No. 13/260,864: Issue fee payment (Apr. 9, 2018); Supplemental Notice of Allowability (dated Jan. 24, 2018); Corrected Filing Receipt (Jan. 17, 2018); Notice of Allowance and Issue Fee Due (dated Jan. 8, 2018), the United States Patent and Trademark Office, Alexandria, VA.
Beijnen, JH et al., "Aspects of the degradation kinetics of doxorubicin in aqueous solution," Int. J. Pharmaceutics 32:123-131 (1986), Elsevier Science Publishers B.V., Amsterdam, Netherlands.
Eisai Inc., "An Open-Label Multicenter Multiple Dose Phase 1 Study to Establish the Maximum Tolerated Dose of E7839 Liposomal Formulation in Patients with Solid Tumors," ClinicalTrials.gov [online] Apr. 19, 2016, National Library of Medicine, Bethesda MD, USA [retrieved on May 19, 2017], Retrieved from the Internet: <URL: https://clinicaltrials.gov/archive/NCT01945710/2016_04_19>, ClinicalTrials Indentifier NCT01945710.
Eisai Co., Ltd., 2011 Nendo (Heisei 24 Nen 3 Gatsuki) Kessan Setsumeikai Shiryo, Eisai Co., Ltd., IR information [online] Eisai Co., Ltd., Tokyo-To Chiyoda-Ku, May 15, 2012, Retrieved from the Internet: <URL:http://www.eisai.co.jp/pdf/ir/mat/4523_120515.pdf.
Maeda, H., "EPR Koka," Kobunshi, 2000, vol. 49, No. 3, p. 129.
Yin, H et al., Enhanced Permeability and Retention (EPR) Effect Based Tumor Targeting: The Concept, Application and Prospect. 2014: JSM Clin Oncol Res 2(1): 1010; Published: Jan. 30, 2014; 5 pages, JSciMed Central, Lewes, Delaware.
Danhier, F et al., "Strategies to improve the EPR effect for the delivery of anti-cancer nanomedicines," Cancer Cell & Microenvironment 2015; 2: e808. doi: 10.14800/ccm.808; 7 pages, Smart Science & Technology LLC, Houston, TX.
Rajora, AK et al., "Impact of the Enhanced Permeability and Retention (EPR) Effect and Cathepsins Levels on the Activity of Polymer-Drug Conjugates," Polymers 2014, 6(8), 2186-2220; Published: Aug. 20, 2014, MDPI, Basel, Switzerland.
Notice of Allowance for Chilean Application No. 2444-2011, dated Jun. 4, 2018, with Resolution Confirming the Allowance, dated Jul. 3, 2018.

(56) References Cited

OTHER PUBLICATIONS

International Search Report for PCT/JP2017/016633, I.A. filed Apr. 26, 2017, dated Jun. 6, 2017, by the Japan Patent Office, Tokyo, Japan.
Maeda, H., "EPR Koka," Kobunshi, 2000, vol. 49, No. 3, p. 129 (English translation).
"Intimation of the grant and recordal of patent under section 43 of the Act in respect of patent application No. 6850/DELNP/2011," for Indian Patent No. 300213, Eisai R&D Management Co. Ltd., applicant, dated Aug. 23, 2018, Intellectual Property India, New Delhi, India.
International Preliminary Report on Patentability (Chapter I of the Patent Cooperation Treaty), PCT Rule 44bis, for International application No. PCT/JP2017/016633, I.A. fd: dated Apr. 26, 2017, Applicant: Eisai F&D Management Co., Ltd., issued Oct. 30, 2018 by The International Bureau of WIPO, Geneva, Switzerland.
Eisai R&D Management Ltd.'s Response (Correction of the Observations) filed Jan. 4, 2020 to the Observation for Peruvian Patent Application No. 001798-2015.
Reply to Oct. 21, 2019 Office action filed Jan. 10, 2020 at the United States Patent and Trademark Office, for U.S. Appl. No. 16/090,360.
Observations by INDECOPI Commission of Inventions and New Technologies, issued Mar. 10, 2020, for Peruvian Patent Appl. No. 001798-2015, INDECOPI, Lima, Peru.
EP Patent Appl. No. 10758755.2: Applicant's Response filed Jun. 3, 2014 to the EP office action dated Jan. 24, 2014.
CN Appl. No. 201080014698.2: Applicant's response filed May 29, 2014 to the CN office action dated Mar. 28, 2014.
EP Patent Appl. No. 10758754.5: Applicant's response filed Aug. 1, 2014 to Communication pursuant to Art. 94(3) EPC dated Jan. 24, 2014.
Notice of Allowance dated Oct. 14, 2014 for Mexican Patent Appl. No. MX/A/2011/009632.
Final Office action for U.S. Appl. No. 16/090,360, dated Mar. 11, 2020, United States Patent and Trademark Office, Alexandria, VA.
International Search Report for International application No. PCT/JP2018/020456, I.A. fd: dated May 29, 2018, Applicant: Eisai F&D Management Co., Ltd., issued Aug. 28, 2018 by the Japan Patent Office, Tokyo, Japan.
"Antineoplastic agent Halaven® intravenous injection 1 mg Halaven® <Eribulin mesilate formulation>," Revised: Feb. 2016 (6th version), 10 pages (pp. 1-6 of the original Japanese version), Eisai Co., Ltd., Japan.
Poujol, S. et al., "Stability of the ready-to-use solutions of eribulin for intravenous infusion," Ann Pharm Fr. Sep. 2012;70(5):249-55. doi: 10.1016/j.pharma.2012.06.004. Epub Jul. 17, 2012.
Hart, J.B. et al., "Acid-Catalyzed Reactions of Homohalichondrin B, a Marine Sponge-Derived Antitumor Polyether Macrolide," J Org Chem. Apr. 19, 1996;61(8):2888-2890.
Notification of the Brazilian Patent and Trademark Office and Documents forwarded by ANVISA (Brazilian Health Surveillance Agency) for Brazilian Patent Application No. PI 1014527-3, including transmittal letter (Jul. 31, 2019); Technical Written Opinion of Consent of a Patent Application of Pharmaceutical Products and Processes (Jul. 18, 2019), supporting documents (Jul. 24, 2019), and "Documents Forwarded by ANVIA" (Sep. 5, 2019), Eisai R&D Management Co., Ltd., applicant.
Zucker, D et al., "Liposome drugs' loading efficiency: a working model based on loading conditions and drug's physicochemical properties," J Control Release. Oct. 1, 2009;139(1):73-80. doi: 10.1016/j.jconrel.2009.05.036. Epub Jun. 7, 2009.
Lasic, DD el al., "Transmembrane gradient driven phase transitions within vesicles: lessons for drug delivery," Biochim Biophys Acta. Nov. 1, 1995; 1239(2):145-56.
Lasic, DD et al., "Gelation of liposome interior. A novel method for drug encapsulation," FEBS Lett. Nov. 9, 1992;312(2-3):255-8.
Fenske, DB et al., "Entrapment of small molecules and nucleic acid-based drugs in liposomes," Methods Enzymol. 2005;391:7-40.
International Preliminary Report on Patentability (Chapter I of the Patent Cooperation Treaty) including the Written Opinion, for International application No. PCT/JP2018/020456, I.A. fd: dated May 29, 2018, Applicant: Eisai F&D Management Co., Ltd., issued Dec. 3, 2019 by The International Bureau of WIPO, Geneva, Switzerland.
Non-final office action for U.S. Appl. No. 16/090,360, dated Oct. 21, 2019, United States Patent and Trademark Office, Alexandria, VA.
Schöffski, P. et al., "Activity of eribulin mesylate in patients with soft-tissue sarcoma: a phase 2 study in four independent histological subtypes," Lancet Oncol. Oct. 2011;12(11):1045-52. doi: 10.1016/S1470-2045(11)70230-3. Epub Sep. 19, 2011.
Narayan, S. et al., "Novel second generation analogs of eribulin. Part III: Blood-brain barrier permeability and in vivo activity in a brain tumor model," Bioorg Med Chem Lett, Mar. 15, 2011;21(6):1639-43. doi: 10.1016/j.bmcl.2011.01.096. Epub Jan. 26, 2011.
Peruvian Patent Application No. 001798-2015, "Observations," Oct. 11, 2019, Indecopi (The National Institute for the Defense of Competition and the Protection of Intellectual Property), Lima, Peru.
The extended European search report, including the supplementary European search report and the European search opinion, dated Nov. 27, 2019, for EP application No. 17789632.1, European Patent Office, Munich, Germany.
News Release No 19-72, dated Sep. 24, 2019: "Eisai to Present Abstracts on Oncology Products and Pipeline at ESMO 2019 Congress," Eisai Co., Ltd.
Takahashi, S. et al., "One-year follow-up results of eribulin for soft-tissue sarcoma including rare subtypes in a real-world observational study in Japan," Poster Display, Abstract No. 1683P displayed Sep. 28, 2019, European Society for Medical Oncology (ESMO) 2019 Congress, Barcelona, Spain.
Yamamoto, N. el al., "Phase 1 study of the liposomal formulation of eribulin (E7389-LF) in Patients with Advanced Solid Tumors: Primary Results of the Dose-Escalation Part," Poster Display, Abstract No. 348P, displayed Sep. 29, 2019, European Society for Medical Oncology (ESMO) 2019 Congress, Barcelona, Spain.
Kazmi, S. et al.,, "Real-world 1-year survival analysis of patients with metastatic breast cancer with liver or lung visceral metastasis treated with eribulin, gemcitabine, or capecitabine," Poster Display, Abstract No. 366P, displayed Sep. 29, 2019, European Society for Medical Oncology (ESMO) 2019 Congress, Barcelona, Spain.
Technical Examination report for Brazilian Patent Application No. PI 1014527-3, dated Mar. 30, 2020, by the Brazilian Patent and Trademark Office.
Response and amendment filed Jun. 24, 2020, to the communication pursuant to Rules 70(2)/70a(2) EPC, dated Dec. 17, 2018, for European Patent Application No. 17 789 632.1.
Response filed Jul. 23, 2020 to an office action in Peruvian Patent Application No. 001798-2015.
Office action for Brazilian Patent Application No. PI10145273, dated Jul. 14, 2020.
Letters Patent for Algeria Patent No. 10271, granted Sep. 13, 2020 for Algeria Patent Application No. 110640.
News Release No. 20-56, dated Sep. 18, 2020, "Eisai presents latest data of phase I clinical trial on liposomal formulation of anti-cancer agent Halaven® (Eribulin) at ESMO Virtual Congress 2020," Author unknown, Eisai Co., Ltd., Tokyo, Japan.
News Release No. 20-54, dated Sep. 11, 2020, "Eisai to present abstracts on oncology products and pipeline at ESMO Virtual Congress 2020," Author unknown, Eisai Co., Ltd., Tokyo, Japan.
Tamura, K et al., Phase 1 study of the liposomal formulation of eribulin (E7389-LF): Results from the HER2-negative breast cancer expansion, Abstract 346P, Sep. 17, 2020, the European Society for Medical Oncology (ESMO) Virtual Congress, Sep. 19-21, 2020, Annals of Oncology (2020) 31 (suppl_4):S348-S395, 10.1016/annonc/annonc268.
Tamura, K et al., Phase 1 study of the liposomal formulation of eribulin (E7389-LF): Results from the HER2-negative breast cancer expansion, E-poster for Abstract 346P, presented at the European Society for Medical Oncology (ESMO) Virtual Congress, Sep. 19-21, 2020, Annals of Oncology (2020) 31 (suppl_4):S348-S395, 10.1016/annonc/annonc268.
Iwasa, S. et al., Effect of infusion rate, premedication, and prophylactic peg-filgrastim treatment on the safety of the liposomal for-

(56) References Cited

OTHER PUBLICATIONS mulation of eribulin (E7389-LF): Results from the expansion part of a phase 1 study, Abstract 583P, Sep. 17, 2020, the European Society for Medical Oncology (ESMO) Virtual Congress, Sep. 19-21, 2020, Annals of Oncology (2020) 31 (suppl_4): S462-S504, 10.1016/annonc/annonc271.
Iwasa, S. et al., Effect of infusion rate, premedication, and prophylactic peg-filgrastim treatment on the safety of the liposomal formulation of eribulin (E7389-LF): Results from the expansion part of a phase 1 study, E-poster for Abstract 583P, presented at the European Society for Medical Oncology (ESMO) Virtual Congress, Sep. 19-21, 2020, Annals of Oncology (2020) 31 (suppl_4):S462-S504, 10.1016/annonc/annonc271.
Response filed Oct. 6, 2020 to the Jul. 14, 2020 office action for Brazilian Patent Application No. PI10145273.
Response filed on Jul. 2, 2020 to the Office Action dated Mar. 30, 2020, for the Brazilian Patent Application No. PI 1014527-3 with an English translation of the Response and of the amended Claims.
Request for Examination for TW Patent Application No. 147388, filed on Mar. 30, 2013, with English Translation thereof.
Patent Certificate for TW Patent No. 1392519, granted Apr. 11, 2013, with English Translation thereof.
Patent Certificate for BN Patent No. RE/R/2017/0029, granted Jul. 4, 2017.
Request for Examination for Brazilian Patent Application No. PI 1014527-3, filed on Dec. 27, 2011, with English Translation thereof.
Patent Certificate for CA Patent No. 2,756,811, granted Sep. 23, 2014.
Patent Certificate for CL Patent No. 56.288, granted Jul. 3, 2018, with English Translation thereof.
Request for Examination for CN Patent Application No. 201080014698.2, filed on Sep. 29, 2011, with English Translation thereof.
Patent Certificate for CN Patent No. ZL201080014698.2, granted Oct. 29, 2014, with English translation thereof.
Request for Examination for CO Patent Application No. 11 130.828, filed on Jul. 17, 2012, with English Translation Thereof.
Patent Certificate for CO Patent No. 4584, granted Jan. 17, 2014, with English Translation thereof.
Request for Examination for EG Patent Application No. PCT1637-2011, filed on Oct. 3, 2011, with English Translation thereof.
Patent Certificate for EP Patent No. 2415470, granted Jul. 6, 2016.
Patent Certificate for HK Patent No. HK1165707, granted Jul. 7, 2017.
Request for Examination for ID Patent Application No. W-00201103470, filed on Sep. 29, 2011, with English Translation thereof.
Patent Certificate for ID Patent No. IDP000045351, granted Apr. 20, 2017, with English Translation thereof.
Patent Certificate for IL Patent No. 215059, granted Jul. 1, 2016.
Request for Examination for IN Patent Application No. 6850-DELNP-2011, filed on Sep. 7, 2011.
Request for Examination for JP Patent Application No. 2011-507240, filed on Jan. 10, 2013, with English Translation thereof.
Patent Certificate for JP Patent No. 5551683, granted May 30, 2014, with English Translation thereof.
Patent Certificate for KR Patent No. 10-1495951, granted Feb. 16, 2015, with English Translation thereof.
Patent Certificate for LK Patent No. 16427, granted Aug. 6, 2014.
Patent Certificate for MA Patent No. 33127, granted Mar. 1, 2012, with English Translation thereof.
Patent Certificate for MX Patent No. 326330, granted Dec. 15, 2014, with English Translation thereof.
Request for Examination for MY Patent Application No. PI2011004382, filed on Sep. 15, 2011.
Patent Certificate for MY Patent No. MY-160203-A granted Feb. 28, 2017.
Patent Certificate for NZ Patent No. 595212, granted Jun. 4, 2014.
Patent Certificate for PH Patent No. 1-2011-501838, granted Nov. 25, 2015.
Request for examination for RU Patent Application No. 2011139715, filed on Sep. 29, 2011, with English Translation thereof.

Patent Certificate for RU Patent No. 2476216, granted Feb. 27, 2013, with English Translation thereof.
Furnishing of Prescribed information and voluntary amendment and payment of Fee for Grant for SG Patent Application No. 2011063880, filed on Mar. 26, 2014.
Patent Certificate for SG Patent No. 174255, granted Apr. 15, 2014.
Request for Examination for UA Patent Application No. a201111426, filed on Feb. 1, 2013, with English translation thereof.
Patent Certificate for UA Patent No. 103794, granted Nov. 25, 2013, with English translation thereof.
Request for Examination for VN Patent Application No. 1-2011-02950, filed on Oct. 31, 2011, with English translation thereof.
Patent Certificate for VN Patent No. 17167, granted Jul. 4, 2017, with English Translation thereof.
Patent Certificate for ZA Patent No. 2011/06535, granted May 30, 2012.
Patent Certificate for EP Patent No. 2415464, granted May 10, 2017.
Request for Examination for JP Patent Application No. 2011-507239, filed on Jan. 10, 2013, with English Translation thereof.
Patent Certificate for JP Patent No. 5622719, granted on Oct. 3, 2014, with English Translation thereof.
Patent Certificate for U.S. Pat. No. 9,968,583, granted May 15, 2018.
Patent Certificate for AU Patent No. 2014200717, granted on Jun. 9, 2016.
Request for Examination for JP Patent Application No. 2014-92382, filed on May 28, 2014, with English Translation thereof.
Patent Certificate for JP Patent No. 5770336, granted on Jul. 3, 2015, with English Translation thereof.
Request for Examination for JP Patent Application No. 2018-514683, filed on Apr. 17, 2020, with English Translation thereof.
Request for Examination for CN Patent Application No. 201880024121.6, filed on Oct. 9, 2019, with English Translation thereof.
Response filed on Jul. 13, 2020 to Final Office Action dated Mar. 11, 2020 in U.S. Appl. No. 16/090,360.
Office action dated Oct. 2, 2020 in U.S. Appl. No. 16/090,360.
Excerpted file history, U.S. Appl. No. 16/090,360, Reply to the Oct. 2, 2020 Office action: Reply filed Feb. 26, 2021, USPTO, Alexandria, VA.
Office action dated Aug. 4, 2014 for (Israel Patent Appl. No. 215059, Israel Patent Office, Jerusalem, Israel (corrected year).
Excerpted file history, U.S. Appl. No. 13/260,872, Notice of abandonment (dated Dec. 3, 2013), USPTO, Alexandria, VA.
Patent Certificate for IN Patent No. 300213, granted Aug. 23, 2018.
Notice of Allowance dated Oct. 20, 2020 for Brazilian Patent Application No. PI 1014527-3 A2; as listed in Patents—The Official Gazette No. 2598, Oct. 20, 2020, p. 1572/1911.
Excerpted file history U.S. Appl. No. 17/067,302, filed Oct. 9, 2020: non-final Office action (dated Dec. 30, 2020); Decision Granting Request for Prioritized Examination (Track I) (Nov. 12, 2020); filing receipt mailed Oct. 21, 2020 and Certification and Request for Prioritized Examination under 37 CFR 1.102(e) (Oct. 9, 2020).
Office Decision for Egyptian Patent Application No. 2011091637 (PCT1637/2011), dated Dec. 20, 2020.
Response filed Aug. 5, 2021 to the Apr. 7, 2021 "Notice of Reasons for Rejection," for JP Patent Application No. 2018-514683.
"Technical report indicating fulfillment or non-fulfillment of the requirements and conditions for patentability based on the search report," issued by the Egyptian Patent Office, dated Aug. 10, 2021, for Egyptian Patent Application No. PCT 1637/2011.
Petition filed by owner Eiasi R&D Management Co., Ltd., Sep. 28, 2021, in the Egyptian Patent Office, for Egyptian Patent Application No. PCT 1637/2011.
USPTO Office action for U.S. Appl. No. 16/090,360, dated Oct. 13, 2021.
Applicant's "Reply to the Office action dated Oct. 13, 2021," for U.S. Appl. No. 16/090,360, Reply filed Dec. 29, 2021 at the United States Patent and Trademark Office, Alexandria, VA.
"Request for Appeal," filed at the Japan Patent Office on Dec. 7, 2021, in JP Patent Appl. No. JP 2018-514683.
"Amendment" filed at the Japan Patent Office dated Dec. 7, 2021, in JP Patent Appl. No. JP 2018-514683.

(56) References Cited

OTHER PUBLICATIONS

"Notice of registration and payment of the fee for issuance of the patent," for Thai Patent Application No. 1101002341, dated Nov. 15, 2021, from the Thailand Patent Office.
Excerpted file history, U.S. Appl. No. 17/067,302, Issue Notification (Jul. 7, 2021); Notice of Allowance and Issue Fee Due (dated May 28, 2021); Request for Continued Examination (dated Apr. 12, 2021); Notice of Allowance and Issue Fee Due (dated Mar. 31, 2021), USPTO, Alexandria, VA.
Response filed on Mar. 25, 2021 in reply to Egyptian Patent Office Official Decision No. 20 (issued on Dec. 29, 2020) for Egyptian patent application No. PCT 1637/2011.
Masuda, M. et al., "Phase 1 Expansion Study of Liposome Formulation of Eribulin (E7389-LF) for Solid Tumors: Focus on Breast Cancer," Poster presented at JSMO2021 Virtual Congress: The Japanese Society of Medical Oncology Annual Meeting, Feb. 18-21, 2021, Feb. 21, 2021.
Masuda, M. et al., "Phase 1 Expansion Study of Liposome Formulation of Eribulin (E7389-LF) for Solid Tumors: Focus on Breast Cancer," Abstract, presented at JSMO2021 Virtual Congress: The Japanese Society of Medical Oncology Annual Meeting, Feb. 18-21, 2021, available online Feb. 10, 2021, Abstract No. O15-4[Encore], p. 670.
Excerpted file history, U.S. Appl. No. 16/090,360, final Office action, dated Apr. 2, 2021, from the US Patent and Trademark Office, Alexandria, VA.
"Notice of Reasons for Rejection," for JP Patent Application No. 2018-514683, Japan Patent Office, Tokyo Japan.
Excerpted file history, U.S. Appl. No. 17/067,302, Reply to the Dec. 30, 2020 Office action: Reply filed Mar. 19, 2021, USPTO, Alexandria, VA.
Response filed Nov. 11, 2021 to Communication pursuant to Article 94(3) EPC dated Sep. 20, 2021 in European Patent Application No. 17789632.1.
Communication pursuant to Article 94(3) EPC for EP Appl. No. 17 789 632.1, dated Sep. 20, 2021, from the European Patent Office, Munich, Germany.
Decision of Rejection, for JP Patent Appl. No. 2018-514683, dated Sep. 17, 2021, from the Japan Patent Office, Tokyo, Japan.
Reply to the Apr. 2, 2021 Office action in U.S. Appl. No. 16/090,360, reply filed Sep. 21, 2021, at the United States Patent and Trademark Office, Alexandria, VA, including petition for extension of time, Request for Continued Examination, electronic acknowledgement receipt and electronic patent application fee transmittal.
News Release No. 21-27, "Eisai to present data on oncology pipeline and products at ASCO Annual Meeting," dated May 20, 2021, Eisai Co., Ltd.
Yamaguchi, K. et al., "Phase 1 study of the liposomal formulation of eribulin (E7389-LF): Results from the advanced gastric cancer expansion cohort," (Study 114), Abstract No. 4025, Annual Meeting of the American Society of Clinical Oncology (ASCO), Jun. 4-8, 2021, (virtual), Abstract published May 19, 2021, at https://meetinglibrary.asco.org/record/199302/abstract.
Yamaguchi, K. et al., "Phase 1 study of the liposomal formulation of eribulin (E7389-LF): Results from the advanced gastric cancer expansion cohort," (Study 114), Poster for Abstract No. 4025, Annual Meeting of the American Society of Clinical Oncology (ASCO), Jun. 4-8, 2021, (virtual).
Haginaka, J et al., "Welcome message," 31st International Symposium on Pharmaceutical and Biomedical Analysis (PBA2021), Aug. 29-Sep. 1, 2021, Kyoto University at Katsura, Kyoto, Japan, http://soyaku.phar.kyushu-u.ac.jp/PBA2021/index.html.
Mano, Y., "A separate determination of released and liposomal encapsulated eribulin in dog plasma by LC-MS/MS for its application to a pharmacokinetic study," Abstract for poster presented at the 31st International Symposium on Pharmaceutical and Biomedical Analysis (PBA2021), Meeting date: Aug. 29-Sep. 1, 2021, Kyoto University at Katsura, Kyoto, Japan; poster date: Aug. 30-31, 2021.
Mano, Y., "A separate determination of released and liposomal encapsulated eribulin in dog plasma by LC-MS/MS for its application to a pharmacokinetic study," Poster presented at the 31st International Symposium on Pharmaceutical and Biomedical Analysis (PBA2021), meeting date: Aug. 29-Sep. 1, 2021, Kyoto University at Katsura, Kyoto, Japan; poster date: Aug. 30-31, 2021.
News Release No. 21-73, "Eisai to present abstracts on oncology products and pipeline at ESMO virtual congress 2021," dated Sep. 14, 2021, Eisai Co., Ltd.
Yamamoto, N. et al., "Phase 1b study of a liposomal formulation of eribulin (E7389-LF) + nivolumab (Nivo) in patients (pts) with advanced solid tumors," Abstract for ePoster 980P, presented at the European Society for Medical Oncology (ESMO) Virtual Congress 2021, Meeting date: Sep. 16-21, 2021; Paris (virtual); Annals of Oncology (2021) 32 (suppl_5): S829-S866. 10.1016/annonc/annonc705.
Yamamoto, N. et al., "Phase 1b study of a liposomal formulation of eribulin (E7389-LF) + nivolumab (Nivo) in patients (pts) with advanced solid tumors," ePoster 980P, the European Society for Medical Oncology (ESMO) Virtual Congress 2021, Paris (Virtual), Sep. 16-21, 2021.
Final Office action dated Jan. 25, 2022 for U.S. Appl. No. 16/090,360, from the United States Patent and Trademark Office, Alexandria, VA.
"Decision to Grant a Patent," for JP Patent Appl. No. 2018-514683, dated Jan. 14, 2022, from the Japan Patent Office, Tokyo, Japan.
Patent Certificate for JP Patent No. 7015237, issued Jan. 25, 2022, by the Japan Patent Office, Tokyo, Japan.
Patent Certificate for Peruvian Patent No. 10407, issued Sep. 1, 2020.
Letters Patent for Thai Patent No. 85826, granted Dec. 13, 2021.
Sato, J et al.," Dose Escalation Data from the Phase 1 Study of the Liposomal Formulation of Eribulin (E7389-LF) in Japanese Patients with Advanced Solid Tumors," Clin Cancer Res (2022) 28 (9): 1783-1791, https://aacrjournals.org/clincancerres/article/doi/10.1158/1078-0432.CCR-21-3518/681620/Phase-1-Dose-Escalation-Study-of-the-Liposome.
Mano, Y., "A separate assay of released and liposomal encapsulated eribulin in dog plasma by liquid chromatography with tandem mass spectrometry for its application to a pharmacokinetic study" J of Separation Science, Mar. 2, 2022.
Niwa, Y. et al., Antitumor activity of liposomal formulation of eribulin combined with anti-PD-1, Amer. Assoc. for Cancer Research (AARC), 2022 Annual Meeting, April 8-13, New Orleans, Louisiana, Poster No. 5584.
Masuda, N. et al., Phase 1 study of the liposomal formulation of eribulin (E7389-LF): Results from the breast cancer expansion cohort. Eur J Cancer. Jun. 2022; 168: 108-118. doi: 10.1016/j.ejca.2022.03.004. Epub Apr. 2, 20229. PMID: 35500404.
GCC Patent Application No. 2010/16760 Amendment and response to Office action, filed Aug. 24, 2014, and filing receipt (1st examination report).
Patent Certificate for Iraq Patent No. 3805 (Iraq Patent Appl. No. 2010/281), granted Mar. 4, 2014.
Registration Certificate No. 83009 granted Jun. 3, 2014 for Iran Patent Application No. 389060963.
Office action for Jordon patent application No. 318/2020, dated Apr. 23, 2018.
Jordon patent application No. 318/2010, preliminary acceptance dated May 30, 2018.
Jordan Letters Patent 3282 dated Dec. 19, 2018 for Appl. No. 318/2010.
Lebanon Letters Patent No. 9155 dated Oct. 7, 2010.
Notice of Examination dated Sep. 29, 2011 for Pakistan Patent Application No. 803/2010.
Letters Patent No. 196 granted Nov. 25, 2017 for Yemen Patent Application No. 567/2010.
Argentina Patent Appl. No. P 10 01 03420: "Substantive Examination" report dated Nov. 6, 2019, Instituto Nacional de la Propiedad Industrial, Argentina.
Argentina Patent Appl. No. P 10 01 03420: Applicant's (Eisai R&D Management Co, Ltd.) response to the Nov. 6, 2019 Substantive Examination report, filed Aug. 4, 2020.

(56) References Cited

OTHER PUBLICATIONS

Argentina Patent Appl. No. P 10 01 03420: "Report Prior to Final Decision," dated Oct. 7, 2020, Instituto Nacional de la Propiedad Industrial, Argentina.
Argentina Patent Appl. No. P 10 01 03420: Applicant's (Eisai R&D Management Co, Ltd.) response to Oct. 7, 2020 Report, dated May 13, 2021.
Argentina Patent Appl. No. P 10 01 03420: "Rejection Report (N)" dated Jun. 9, 2021, Instituto Nacional de la Propiedad Industrial, Argentina.
Argentina Patent Appl. No. P 10 01 03420: Applicant's (Eisai R&D Management Co, Ltd.) Administrative Appeal for Reconsideration against the Rejection Decision, filed Jan. 24, 2022.
Egyptian Patent Appl. No. 1637/2011 (EG/P/2011/1637): Eisai R&D Management Co., Ltd. Response filed on Jun. 27, 2022 to the official rejection decision mailed Sep. 28, 2021.
GCC (Gulf Cooperation Council) Patent Application No. 2010/016760: Examination Fees Notification Request, dated Oct. 22, 2013, Patent Office of the Cooperation Council for the Arab States of the Gulf.
GCC (Gulf Cooperation Council) Patent Application No. 2010/016760: Notice of payment of fees for the 1st Substantive Examination, dated Jan. 13, 2014 for the 1st Substantive Examination, Patent Office of the Cooperation Council for the Arab States of the Gulf.
GCC (Gulf Cooperation Council) Patent Application No. 2010/016760: Examination Report dated Jan. 26, 2014, Patent Office of the Cooperation Council for the Arab States of the Gulf.
GCC (Gulf Cooperation Council) Patent Application No. 2010/016760: Examination Report dated Sep. 16, 2014, Patent Office of the Cooperation Council for the Arab States of the Gulf.
GCC (Gulf Cooperation Council) Patent Application No. 2010/016760: Response to the $2^{nd}$Examination Report of Sep. 16, 2014, response filed Jan. 21, 2015.
Jordanian Appl. No. 318/2010: Response to the Office Action filed on May 21, 2018.
Argentina Patent Appl. No. P 10 01 03420: Provision: Rejection decision by the National Patent Administration., Jun. 24, 2021.
Communication under Rule 71(3) EPC for European Patent Application. No. 17 789 632.1, dated Jul. 12, 2022 by the European Patent Office, Munich, Germany.
Notice of Appeal filed at the United States Patent and Trademark Office dated Jul. 22, 2022, for U.S. Appl. No. 16/090,360.
Appeal Brief filed at the United States Patent and Trademark Office dated Sep. 21, 2022, for U.S. Appl. No. 16/090,360.
Notice of Allowance and Issue Fee Due, for U.S. Appl. No. 16/090,360, dated Nov. 7, 2022, from the United States Patent and Trademark Office, Alexandria, VA.
Applicant's Response to Rule 71(3) EPC communication of Jul. 12, 20- 22, filed at the European Patent Office, Munich, Germany, dated Nov. 9, 2022 in European Application No. 17789632.1.
Communication under Rule 71(3) EPC dated Dec. 21, 2022 for European Patent Application No. 17789632.1, The European Patent Office, Munich, Germany.
Consolidated List—EP 16710891.9; European Patent Office (4 pages).
Niwa, Y., et al., "Antitumor activity of liposomal formulation of eribulin combined with anti-PD-1" Cancer Res. (AACR Annual Meeting 2022) 82 (12 Supplement): Abstract 5584, American Association for Cancer Research, United States (Jun. 2022).
Tanioka, M., et al., "Anti-tumor activity of a liposomal formulation of Eribulin compared with the same dose of Eribulin in patient-derived breast cancer xenografts" San Antonio Breast Cancer Symposium 45th Annual Meeting Abstract P3-07-03, Encore Medical Education, United States (Nov. 21, 2022).
Ooki, A., et al., "The esophageal cancer cohort of a phase 2 trial of E7389-LF (liposomal formulation of eribulin) + nivolumab," Journal of Clinical Oncology (ASCO Gastrointestinal Cancers Symposium 2023) 41( 4_Supplement): Abstract 337, American Society of Clinical Oncology, San Francisco, CA, (Jan. 2023).

Muro, K., et al., "Gastric cancer (GC) cohort of a phase 2 trial of E7389-LF (liposomal formulation oferibulin) in combination with nivolumab." Journal of Clinical Oncology (ASCO Gastrointestinal Cancers Symposium 2023) 41( 4_Supplement): Abstract 339, American Society of Clinical Oncology, San Francisco, California, United States (Jan. 2023).
Tanioka, M., et al., "Anti-tumor activity of a liposomal formulation of Eribulin compared with the same dose of Eribulin in patient-derived breast cancer xenografts" presented at San Antonio Breast Cancer Symposium 45th Annual Meeting, San Antonio, TX, Dec. 7, 2022, Poster P3-07-03, 1 page.
Niwa, Y., et al., "Liposome-encapsulated eribulin shows enhanced antitumour activity over eribulin for combination therapy with anti-PD-1 antibody" Mol. Cancer Ther. MCT-22-0475, American Association for Cancer Research, United States (Jan. 2023).
Shitara, K., et al., "Phase I Study of the Liposomal Formulation of Eribulin (E7389-LF): Results from the Advanced Gastric Cancer Expansion Cohort" Clinical Cancer Research OF1- OF8:CCR-22-3027, American Association for Cancer Research, United States (Feb. 2023).
Muro, K., et al. "Gastric cancer (GC) cohort of a phase 2 trial of E7389-LF (liposomal formulation oferibulin) in combination with nivolumab," presented at ASCO Gastrointestinal Cancers Symposium 2023, San Francisco, CA, Jan. 17, 2023, Poster 339, 1 page.
Ooki, A., et al., "The esophageal cancer cohort of a phase 2 trial of E7389-LF (liposomal formulation of eribulin) + nivolumab," presented at ASCO Gastrointestinal Cancers Symposium, Jan. 17, 2023, San Francisco, CA, Poster 337, 1 page.
Response to first office action for Chinese Patent Application No. 202080042486.9 dated Mar. 10, 2023, China National Intellectual Property Administration, China, 47 pages (English Language Translation Appended).
Amendment filed in Singapore Patent Application No. 11201706872S dated Feb. 22, 2018, 12 pages.
Response filed in Singapore Patent Application No. 11201706872S dated Mar. 2, 2018, 19 pages.
Response filed in Singapore Patent Application No. 11201706872S dated Nov. 30, 2018, 17 pages.
Response filed in Singapore Patent Application No. 11201706872S dated Apr. 1, 2020, 18 pages.
Office Action for Singapore Patent Application No. 11201706872S dated Jan. 21, 2021, Intellectual Property Office of Singapore, Singapore, 1 page.
Office Action for Singapore Patent Application No. 11201706872S dated Jul. 21, 2021, Intellectual Property Office of Singapore, Singapore, 1 page.
Amendment dated Aug. 30, 2017 in U.S. Appl. No. 15/554,540, Matsui, J., et al., (371 dated Aug. 30, 2017), 9 pages.
Office Action dated Mar. 22, 2019 in U.S. Appl. No. 15/554,540, Matsui, J., et al., (371 dated Aug. 30, 2017), 12 pages.
Response dated Sep. 23, 2019 in U.S. Appl. No. 15/554,540, Matsui, J., et al., (371 dated Aug. 30, 2017), 33 pages.
Office Action dated Jan. 2, 2020 in U.S. Appl. No. 15/554,540, Matsui, J., et al., (371 dated Aug. 30, 2017), 10 pages.
Response dated May 4, 2020 in U.S. Appl. No. 15/554,540 dated, Matsui, J., et al., (371 dated Aug. 30, 2017),, 17 pages.
Office Action dated Aug. 11, 2020 in U.S. Appl. No. 15/554,540, Matsui, J., et al., (371 dated Aug. 30, 2017), 7 pages.
Response dated Oct. 13, 2020 in U.S. Appl. No. 15/554,540, Matsui, J., et al., (371 dated Aug. 30, 2017), 5 pages.
Notice of Allowance dated Nov. 4, 2020 in U.S. Appl. No. 15/554,540, Matsui, J., et al., (371 dated Aug. 30, 2017), 7 pages.
Response dated Jan. 12, 2021 in U.S. Appl. No. 15/554,540, Matsui, J., et al., (371 dated Aug. 30, 2017), 3 pages.
Response dated Feb. 2, 2021 in U.S. Appl. No. 15/554,540, Matsui, J., et al., (371 dated Aug. 30, 2017), 1 page.
Amendment filed in European Patent Application No. 16710891.9, dated May 3, 2018, 11 pages.
Response filed in European Patent Application No. 16710891.9, dated Dec. 23, 2019, 14 pages.
Amendment filed in European Patent Application No. 16710891.9, dated Feb. 18, 2020, 7 pages.

(56) References Cited

OTHER PUBLICATIONS

Amendment filed in European Patent Application No. 16710891.9, dated Aug. 10, 2020, 25 pages.
Response filed in European Patent Application No. 16710891.9, dated Jan. 26, 2021, 114 pages.
Notice of Intent to Grant for European Patent Application No. 16710891.9, dated Oct. 20, 2021, European Patent Office, Netherlands, 149 pages.
Decision to Grant for European Patent Application No. 16710891.9, dated Apr. 7, 2022, European Patent Office, Germany, 3 pages.
Opposition filed in European Patent Application No. 16710891.9, dated Jan. 23, 2023, European Patent Office, Germany, 33 pages.
Opposition filed in European Patent Application No. 16710891.9, dated Jan. 27, 2023, European Patent Office, Germany, 7 pages.
Opposition filed in European Patent Application No. 16710891.9, dated Feb. 8, 2023, European Patent Office, Germany, 111 pages.
Opposition filed in European Patent Application No. 16710891.9, dated Feb. 9, 2023, European Patent Office, Germany, 20 pages.
Office Action for European Patent Application No. 16710891.9, dated Feb. 17, 2023, European Patent Office, Germany, 2 pages.
Clinicaltrials.gov, "Clinical Trial NCT01848834, History of Changes for Study: NCT01848834: Study of Pembrolizumab (MK-3475) in Participants with Advanced Solid Tumors (MK-3475-012/KEYNOTE-012)" as published on Jan. 21, 2015, accessed at https://clinicaltrials.gov/ct2/show/NCT01848834, 10 pages.
Eisai Press Release on Mar. 4, 2015, "Eisai and Merck Enter Collaboration to Explore Novel Combination Regimens of Anti-PD-1 Therapy with Multi-targeting RTK Inhibitor and Microtubule Dynamics Inhibitor in Multiple Types of Cancer," accessed at http://www.eisai.com/news/enews201518p, 8 pages.
Highlights of Prescribing Information of HALAVEN (eribulin mesylate), published Nov. 2010, 15 pages.
Highlights of Prescribing Information of KEYTRUDA (pembrolizumab), published Sep. 2014, 16 pages.
World Health Organization, "WHO Drug Information," 27(2), 2013 (excerpt on lambrolizumab (synonym for pembrolizumab), 115 pages.
Clinicaltrials.gov, "History of Changes for Study: NCT02513472: Study to Evaluation the Efficacy and Safety of Eribulin Mesylate in Combination with Pembrolizumab in Subjects with Metastatic Triple-Negative Breast Cancer (mTNBC)," updated Nov. 12, 2015, accessed at https://clinicaltrials.gov/ct2/show/NCT02513472, 7 pages.
Mancini, P., et al., "Review: Standard of care and promising new agents for triple negative metastatic breast cancer," Cancers 6(4):2187-2223, MDPI, Switzerland (2014).
Morikawa, A., et al., "Review: Treating Triple-Negative Breast Cancer: Where Are We?" Journal of the National Comprehensive Cancer Network 13(2):e8-e18, Harborside Press, United States (Feb. 2015).
Brewster, A.M., et al. "Epidemiology, biology, and treatment of triple-negative breast cancer in women of African ancestry" The Lancet Oncology 15(13):e625-e634, Elsevier, Netherlands (2014).
Doherty, M.K., et al., "Review: Eribulin for the treatment of metastatic breast cancer: an update on its safety and efficacy" International Journal of Women's Health 7:47-58, DovePress, United Kingdom (Jan. 2015).
Publication date of Doherty, M.K., et al., "Eribulin for the treatment of metastatic breast cancer: an update on its safety and efficacy" International Journal of Women's Health 7 (Abstract), DovePress, United Kingdom (Jan. 2015).
Marm, F., et al., "Targeted therapies in triple-negative breast cancer" Breast Care 10(3):159- 166, Karger Publishers, Switzerland (Jun. 2015).
Kalimutho, M., et al. "Review: Targeted therapies for triple-negative breast cancer: Combating a stubborn disease," Trends in Pharmacological Sciences 36(12):822- 846 (Published online Nov. 1, 2015).
McDermott, F., et al., "Review: PD-1 as a potential target in cancer therapy," Cancer Medicine 2(5):662-673, Wiley, United States (2013).
Robert, C., et al., "Drug of the year: programmed death-1 receptor/programmed death-1 ligand-1 receptor monoclonal antibodies," European Journal of Cancer 49(14):2968-2971, Elsevier, Netherlands (2013).
Poole, R.M., "Pembrolizumab: first global approval" Drugs 74(16):1973-1981, Springer, United Kingdom (2014).
Dolan, D.E., et al., "Review: PD-1 pathway inhibitors: changing the landscape of cancer immunotherapy," Cancer Control 21(3):231-237, SAGE Publishers, United States (2014).
Nanda, R., et al., "A phase lb study of pembrolizumab (MK-3475) in patients with advanced triple-negative breast cancer," San Antonio Breast Cancer Symposium 45th Annual Meeting Abstract S1-09, Encore Medical Education, United States (Dec. 2014).
Azvolinsky, A., "Immunotherapy Yields Response in Triple-Negative Breast Cancer," CancerNetwork.com, published Dec. 11, 2014, accessed at https://www.cancernetwork.com/view/immunotherapy-yields-response-triple-negative-breast- cancer, 3 pages.
Azvolinsky, A., "Top 8 Highlights From SABCS 2014" CancerNetwork.com, published Dec. 19, 2014, accessed at https://www.cancernetwork.com/view/top-8-highlights-sabcs- 2014, 2 pages.
"Pembrolizumab Shows Potential in Breast Cancer" Cancer Discovery News in Brief pp. 100-101, American Association for Cancer Research, United States (Feb. 2015).
Ahmed, M., et al., "Report from the 37th San Antonio Breast Cancer Symposium, Dec. 9-13, 2014, Texas, USA," Ecancermedicalscience 4(9):508, Cancer Intelligence, United States (Feb. 2015).
Twelves, C., et al., "Efficacy of eribulin in women with metastatic breast cancer: a pooled analysis of two phase 3 studies," Breast Cancer Research and Treatment 148:553-561, Springer Science+Business Media, Germany (2014).
Mullard, A., "Learning from the 2012-2013 class of breakthrough therapies," Nature Reviews 12:891-893, Nature Publishing Group, United Kingdom (Dec. 2013).
Anonymous, "PD-1 inhibitor becomes 'Breakthrough Therapy,'" Cancer Discovery, American Association for the Cancer Research, United States, 4 pages (Jul. 2013).
Merck Press Release on Apr. 24, 2013, "Merck announces breakthrough therapy designation for lambrolizumab an investigational antibody therapy for advanced melanoma," accessed at https://www.merck.com/news/merck-announces-breakthrough-therapy-designation-for-lambrolizumab-an-investigational-antibody-therapy-for-advanced-melanoma/, 6 pages.
Dolgin, E., "Cancer's True Breakthroughs" Nature Medicine 19(6):660-663, Nature Publishing Group, United Kingdom (Jun. 2013).
Mittendorf, E.A., et al., "PD-L1 Expression in Triple-Negative Breast Cancer," Cancer Immunology Research 2(4):361-370, American Association for Cancer Research, United States (2014).
Clinicaltrials.gov, "History of Changes for Study: NCT02039674: A study of pembrolizumab (MK-3475) in combination with chemotherapy or immunotherapy in participants with non-small cell lung cancer (MK-3475-021/KEYNOTE-021)," accessed at https://clinicaltrials.gov/ct2/history/NCT02039674, 6 pages (Jan. 14, 2015).
Clinicaltrials.gov, "History of Changes for Study: NCT02036502 Study of Pembrolizumab (MK-3475) in Combination With Lenalidomide and Dexamethasone in Participants With Multiple Myeloma (MK-3475-023/KEYNOTE023)," accessed at https://clinicaltrials.gov/ct2/history/NCT02036502, 5 pages (Apr. 2018).
Clinicaltrials.gov, "History of Changes for Study: NCT02331368 Phase 2 Multi-center Study of Anti-PD-1 During Lymphopenic State After HDT/ASCT for Multiple Myeloma," accessed at https://clinicaltrials.gov/ct2/history/NCT02331368, 4 pages (Apr. 2018).
Robert, C., et al., "LBA- Pembrolizumab (pembro; MK-3475) for advanced melanoma: Randomized comparison of two dosing schedules" Annals of Oncology 25(Supplement 5):v1-v41, Elsevier, Netherlands (Sep. 29, 2014).
Bai, S., et al., "A guide to rational dosing of monoclonal antibodies," Clinical Pharmacokinetics 51(2):119-35, Springer Nature, United Kingdom (Feb. 2012).
Kaufman, P., et al., "Efficacy or eribulin in patients (ots) with metastatic breast cancer (MBC): A pooled analysis by HER2 and ER status," Journal of Clinical Oncology 32(26):137-137, American Society of Clinical Oncology, United Kingdom (2014).

(56) References Cited

OTHER PUBLICATIONS

Feature listings of claims 1, 6, 7, and 13 of the opposed patent—filed in opposition against EP3265122 dated Feb. 3, 2023, 2 pages.
Bibliographic data for U.S. Appl. No. 62/128,373 filed in opposition against EP3265122 dated Feb. 3, 2023, accessed at https://patentcenter.uspto.gov/applications/62128373/, 1 page.
Record of assignments for U.S. Appl. No. 62/128,373 filed in opposition against EP3265122 dated Feb. 3, 2023, accessed at https://patentcenter.uspto.gov/applications/62128373/assignments/abstract, 1 page.
Merck Press Release on May 30, 2014, "Merck Announces Generic Name for MK-3475, Merck's Investigational anti-PD-1 Antibody: Pembrolizumab," accessed at https://www.merck.com/news/merck-announces-generic-name-for-mk-3475-mercks-investigational-anti-pd-1-antibody-pembrolizumab/, 2 pages.
Mittendorf, E.A., et al., "PD-L1 Expression in Triple Negative Breast Cancer," Cancer Immunology Research 2(4):361-370, American Association for Cancer Research, United States (Apr. 2014).
Clinicaltrials.gov, "History of Changes for Study: NCT02447003 Study of Pembrolizumab (MK-3475) Monotherapy for Metastatic Triple-Negative Breast Cancer (MK-3475-086/KEYNOTE-086)," accessed at https://www.clinicaltrials.gov/ct2/history/NCT02447003, 10 pages (May 14, 2015).
Funahashi, Y., et al. "Eribulin mesylate reduces tumor microenvironment abnormality by vascular remodeling in preclinical human breast cancer models," Cancer Science 105:1334-1342, Japanese Cancer Association, Japan (2014).
Park, Y., et al., "Clinical Benefits of and Recent Progress in Eribulin Mesylate Therapy for Breast Cancer Patients," Journal of Tumor 2(4): 113-121, ACT Publishing Group, Hong Kong (Apr. 18, 2014).
Lehmann, B.D., et al., "Identification and use of biomarkers in treatment strategies for triple-negative breast cancer subtypes," Journal of Pathology 232:142-150, Wiley, United States (2014).
Vahdat, L., et al., "Eribulin mesylate + trastuzumab as first-line therapy for locally recurrent or metastatic HER2-positive breast cancer: results from a phase 2, multicenter, single-arm study," Cancer Research 72(24):Supp. 3, Abstract No. PS-20-04, American Association for Cancer Research, United States (Dec. 15, 2012).
Clinicaltrials.gov, "History of Changes for Study: NCT02142738 Study of Pembrolizumab (MK-3475) Compared to Platinum-Based Chemotherapies in Participants With Metastatic Non-Small Cell Lung Cancer (MK-3475-024/KEYNOTE-024)," accessed at https://www.clinicaltrials.gov/ct2/history/NCT02142738, 19 pages (published Feb. 17, 2015).
Clinicaltrials.gov, History of Changes for Study: NCT02039674 A Study of Pembrolizumab (MK-3475) in Combination With Chemotherapy or Immunotherapy in Participants With Non-small Cell Lung Cancer (MK-3475-021/KEYNOTE-021), accessed at https://clinicaltrials.gov/ct2/history/NCT02039674, 6 pages (Oct. 2022), published Feb. 25, 2015.
Clinicaltrials.gov, "History of Changes for Study: NCT02305186 Safety and Immunological Effect of Pembrolizumab in Resectable or Borderline Resectable Pancreatic Cancer (UVA-PC-PD101)," accessed at https://clinicaltrials.gov/ct2/history/NCT02305186 (published on Nov. 27, 2014).
Tolaney, S., et al., "Phase 1b/2 study to evaluate eribulin mesylate in combination with pembrolizumab in patients with metastatic triple-negative breast cancer," European Journal of Cancer 72:S16, Abstract No. 177 (2017).
Tolaney, S., et al., "Abstract PD6-13: Phase 1b/2 study to evaluate eribulin mesylate in combination with pembrolizumab in patients with metastatic triple-negative breast cancer," Cancer Research 78(4 Suppl.): Abstract PD6-13, American Association for Cancer Research, United States (2018).
Schmidt, E.V., et al., "Assessment of Clinical Activity of PD-1 Checkpoint Inhibitor Combination Therapies Reported in Clinical Trials," JAMA Network Open 3(2):e1920833, American Medical Association, United States (2020).

Eisai Press Release on Nov. 16, 2010, "U.S. FDA Approves Eisai's Halaven™ (Eribulin Mesylate) Injection for Treatment of Metastatic Breast Cancer," accessed at https://www.eisai.com/news/news201064.html, 2 pages.
Merck Press Release on Sep. 4, 2014, "Merck Receives Accelerated Approval of Keytruda® (pembrolizumab), the first FDA-Approved Anti-PD-1 Therapy," accessed at https://www.merck.com/news/merck-receives-accelerated-approval-of-keytruda-pembrolizumab-the-first-fda-approved-anti-pd-1-therapy/, 3 pages.
Meeting Reporter at 37th Annual San Antonio Breast Cancer Symposium, Oncology Times, Feb. 10, 2015 issue.
Office Action for Australian Patent Application No. 2017342462, dated Jul. 20, 2021, IP Australia, Australia, 1 page.
Office Action for Australian Patent Application No. 2017342462 dated Oct. 1, 2021, IP Australia, Australia, 1 page.
Office Action for Chinese Patent Application No. 201780077525.7 dated Nov. 14, 2022, The State Intellectual Property Office of People's Republic of China, China, 2 pages.
Office Action for Chinese Patent Application No. 201780077525.7 dated Nov. 21, 2022, The State Intellectual Property Office of People's Republic of China, China, 17 pages (English Language Translation Appended).
Office Action for European Patent Application No. 17800964.3 dated May 24, 2019, European Patent Office, Germany, 3 pages.
Office Action for Israeli Patent Application No. 719562 dated Mar. 15, 2020, Israel Patent Office, Israel, 4 pages (English Language Translation Appended).
Response filed in Israeli Patent Application No. 719562 dated Jul. 14, 2020, 10 pages (English Language Translation Appended).
List of Citations filed in Israeli Patent Application No. 719562 dated Jul. 15, 2020, 3 pages.
Office Action for Israeli Patent Application No. 719562 dated Nov. 11, 2021, Israel Patent Office, Israel, 6 pages (English Language Translation Appended).
Office Action for Israeli Patent Application No. 719562 dated Sep. 21, 2022, Israel Patent Office, Israel, 2 pages (English Language Translation Appended).
Office Action for Israeli Patent Application No. 719562 dated Oct. 26, 2022, Israel Patent Office, Israel, 2 pages (English Language Translation Appended).
Response filed in Japanese Patent Application No. 2019-518975 dated Sep. 28, 2020, 4 pages (English Language Translation Appended).
Withdrawal for Japanese Patent Application No. 2019-518975 dated May 10, 2021, Japan Patent Office, 2 pages (English Language Translation Appended).
Amendment filed in Korean Patent Application No. 10-2019-7013370 dated Aug. 3, 2020, Korean Intellectual Property Office, Korea, 23 pages (English Language Translation Appended).
Office Action for Mexican Patent Application No. MX/a/2019/003994 dated Jul. 21, 2022, Mexican Patent Office, 12 pages (English Translation Appended).
Office Action for Singapore Patent Application No. 11201902974P dated Apr. 29, 2021, Intellectual Property Office of Singapore, Singapore, 1 page.
Office Action dated Mar. 4, 2021 in U.S. Appl. No. 16/341,579 (371 dated Apr. 12, 2019), 9 pages.
Notice of Abandonment dated Oct. 7, 2022 in U.S. Appl. No. 16/341,579 (371 dated Apr. 12, 2019), 2 pages.
Amendment filed in Australian Patent Application No. 2016226157 dated Aug. 11, 2020, 10 pages.
Office Action for Australian Patent Application No. 2016226157 dated Jan. 29, 2021, IP Australia, Australia, 5 pages.
Response filed in Australian Patent Application No. 2016226157 dated Nov. 30, 2021, 15 pages.
Office Action for Australian Patent Application No. 2016226157 dated Dec. 15, 2021, IP Australia, Australia, 2 pages.
Response filed in Australian Patent Application No. 2016226157 dated Jan. 5, 2022, 115 pages.
Notice of Allowance for Australian Patent Application No. 2016226157 dated Jan. 18, 2022, IP Australia, Australia, 58 pages.
Office Action for Brazilian Patent Application No. 112017018872-4 dated Sep. 13, 2021, The National Institute of Industrial Property, Brazil, 8 pages (English Language Translation Appended).

(56) References Cited

OTHER PUBLICATIONS

Response filed in Brazilian Patent Application No. 112017018872-4 dated Dec. 16, 2021, The National Institute of Industrial Property, Brazil, 158 pages (English Translation Appended).
Amendment filed in Canadian Patent Application No. 2978311 dated Mar. 2, 2021, 11 pages.
Amendment filed in Canadian Patent Application No. 2978311 dated Apr. 21, 2022, 2 pages.
Office Action for Canadian Patent Application No. 2978311 dated Jun. 3, 2022, Canadian Intellectual Property Office, Canada, 6 pages.
Response filed in Chinese Patent Application No. 201680025588.3 dated Sep. 22, 2020, 26 pages (English Language Translation Appended).
Response filed in Chinese Patent Application No. 201680025588.3 dated Dec. 15, 2020, 8 pages (English Language Translation Appended).
Notice of Allowance for Chinese Patent Application No. 201680025588.3 dated Dec. 31, 2020, 3 pages (English Language Translation Appended).
Office Action for Israeli Patent Application No. 254133 dated Jan. 20, 2019, Israel Patent Office, Israel, 4 pages (English Language Translation Appended).
Response filed in Israeli Patent Application No. 254133 dated May 20, 2019, 12 pages (English Translation Appended).
List of Citations filed in Israeli Patent Application No. 254133 dated Nov. 17, 2019, 8 pages.
List of Citations filed in Israeli Patent Application No. 254133 dated Feb. 2, 2020, 9 pages.
Response filed in Israeli Patent Application No. 254133 dated Mar. 11, 2021, 81 pages (English Language Translation Appended).
Notice of Allowance for Israeli Patent Application No. 254133 dated Jun. 3, 2021, 6 pages (English Language Translation Appended).
List of Citations filed in Israeli Patent Application No. 254133 dated Aug. 11, 2021, 11 pages.
List of Citations filed in Israeli Patent Application No. 254133 dated Aug. 18, 2021, 11 pages.
Notice of Allowance for Israeli Patent Application No. 254133 dated Sep. 19, 2021, Israel Patent Office, Israel, 2 pages (English Language Translation Appended).
Response filed in Indian Patent Application No. 201747034283 dated Nov. 24, 2020, 176 pages.
Response filed in Indian Patent Application No. 201747034283 dated Nov. 27, 2020, 71 pages.
Response filed in Indian Patent Application No. 201747034283 dated Mar. 2, 2021, 2 pages.
Office Action for Indian Patent Application No. 201747034283 dated Mar. 30, 2021, Indian Patent Office, India, 3 pages.
Office Action for Indian Patent Application No. 201747034283 dated Apr. 27, 2021, Indian Patent Office, India, 3 pages.
Response filed in Indian Patent Application No. 201747034283 dated Apr. 27, 2021, 1 page.
Amendment filed in Japanese Patent Application No. 2017-546075 dated Mar. 4, 2019, 6 pages (English Language Translation Appended).
Response filed in Japanese Patent Application No. 2017-546075 dated Apr. 1, 2020, 29 pages (English Language Translation Appended).
Response filed in Japanese Patent Application No. 2017-546075 dated Oct. 15, 2020, 6 pages (English Language Translation Appended).
Office Action for Japanese Patent Application No. 2017-546075 dated Mar. 23, 2021, Japan Patent Office, Japan, 7 pages (English Language Translation Appended).
Response filed in Japanese Patent Application No. 2017-546075 dated May 21, 2021, 6 pages (English Language Translation Appended).
Notice of Allowance for Japanese Patent Application No. 2017-546075 dated Aug. 31, 2021, Japan Patent Office, Japan, 6 pages (English Language Translation Appended).
Amendment filed in Korean Patent Application No. 10-2017-7027617 dated Feb. 23, 2021, Korean Intellectual Property Office, Korea, 17 pages (English Language Translation Appended).
Office Action for Korean Patent Application No. 10-2017-7027617 dated Jan. 9, 2023, Korean Intellectual Property Office, Korea, 11 pages (English Language Translation Appended).
Response filed in Mexican Patent Application No. MX/a/2017/011206 dated Jan. 22, 2021, 79 pages (English Language Translation Appended).
Office Action for Mexican Patent Application No. MX/a/2017/011206 dated Mar. 12, 2021, Mexican Patent Office, Mexico, 12 pages (English Language Translation Appended).
Response filed in Mexican Patent Application No. MX/a/2017/011206 dated21, 22 pages (English Language Translation Appended).
Office Action for Mexican Patent Application No. MX/a/2017/011206 dated Jul. 23, 2021, Mexican Patent Office, Mexico, 4 pages (English Language Translation Appended).
Response filed in Mexican Patent Application No. MX/a/2017/011206 dated Jul. 27, 2021, 8 pages (English Language Translation Appended).
Office Action for Mexican Patent Application No. MX/a/2017/011206 dated Jul. 30, 2021, Mexican Patent Office, Mexico, 4 pages (English Language Translation Appended).
Response filed in Mexican Patent Application No. MX/a/2017/011206 dated Sep. 28, 2021, 10 pages (English Language Translation Appended).
Notice of Allowance for Mexican Patent Application No. MX/a/2017/011206 dated Sep. 28, 2021, Mexican Patent Office, Mexico, 2 pages (English Language Translation Appended).
Response filed in Russian Patent Application No. 2017132877/04 dated Nov. 28, 2019, 16 pages (English Language Translation Appended).
Office Action for Russian Patent Application No. 2017132877/04 dated Jan. 27, 2020, The Federal Service for Intellectual Property, Russia, 8 pages (English Language Translation Appended).
Response filed in Russian Patent Application No. 2017132877/04 dated Jul. 27, 2020, 8 pages (English Language Translation Appended).
International Search Report for PCT/JP2020/028663, Japan Patent Office, dated Sep. 24, 2020 (7 pages).
International Preliminary Report on Patentability for PCT/JP2020/028663, dated Feb. 1, 2022, The International Bureau of WIPO, Geneva, Switzerland (9 pages).
U.S. Appl. No. 17/563,162: Election of species requirement from the U.S. Patent and Trademark Office dated Apr. 14, 2022 and Applicant's Reply dated May 31, 2022 (9 pages).
U.S. Appl. No. 17/563,162: Corrected Notice of Allowability from the U.S. Patent and Trademark Office dated Oct. 26, 2022 (6 pages).
Request for Continued Examination filed Dec. 15, 2022 in U.S. Appl. No. 17/563,162: (3 pages).
Electronic Acknowledgement Receipt or Request for Continued Examination filed Dec. 15, 2022 in U.S. Appl. No. 17/563, 162: (3 pages).
U.S. Appl. No. 17/563,162: Notice of Allowance and Fee(s) Due from the U.S. Patent and Trademark Office dated Sep. 15, 2022 (15 pages).
First office action for Chinese Patent Application No. 202080042486.9 dated Mar. 10, 2023, China National Intellectual Property Administration, China, 47 pages (English Language Translation Appended).
Israeli Patent Application No. 289213 List of corresponding applications and list of citations, dated Oct. 13, 2022, 6 pages (English Language Translation Appended).
U.S. Appl. No. 17/563,162: Notice of Withdrawal from Issue from the U.S. Patent and Trademark Office, dated Mar. 7, 2023 (2 pages).
U.S. Appl. No. 17/563,162: Notice of Allowance and Fee(s) Due from the U.S. Patent and Trademark Office dated Jan. 20, 2023 (11 pages).
Response to Rules 161(2) and 162 EPC, submitted to the European Patent Office dated Jul. 25, 2022 for EP Appl. No. 20 847 524.4.
Notice of Allowance and Issue Fee Due, for U.S. Appl. No. 16/061,426, dated Mar. 22, 2023, from the United States Patent and Trademark Office, Alexandria, VA.
First office action for Chinese Patent Application No. 202080042486.9 dated Sep. 26, 2022, China National Intellectual Property Administration, China, 13 pages (English Language Translation Appended).

(56) References Cited

OTHER PUBLICATIONS

Notice of Allowance and Issue Fee Due, for U.S. Appl. No. 16/090,360, dated Mar. 22, 2023, from the United States Patent and Trademark Office, Alexandria, VA.
Request for Continued Examination (RCE) Transmittal U.S. Appl. No. 16/090,360, filed Mar. 31, 2023, at the United States Patent and Trademark Office, Alexandria, VA.
Notice of Allowance and Issue Fee Due, for U.S. Appl. No. 16/090,360, dated Apr. 19, 2023, from the United States Patent and Trademark Office, Alexandria, VA.
Niwa et al., "Antitumor activity of liposomal formulation of eribulin combined with anti-human PD-1 antibody using hPBMC-humanized mouse models," American Assoc for Cancer Research (AARC) Annual Meeting, Apr. 14-19, 2023, Orlando, Florida, Session PO.IM01.15, abstract 5075 / 9, Mar. 31, 2023, presented Apr. 18, 2023.
Notification of the Second Office Action, for CN Appl. No. 202080042486.9, dated Mar. 22, 2023 from CNIPA.
Response to Rule 71(3) filed on Apr. 14, 2023 in EP Patent Application No. 17789632.1 EP 3 449 921).
Notice of Allowance and Issue Fee Due, for U.S. Application No. 17/563, 162, dated Apr. 19, 2023, from the United States Patent and Trademark Office, Alexandria, VA.
Notice of Withdrawal from Issue, dated May 5, 2023, for U.S. Appl. No. 17/563,162 from the United States Patent and Trademark Office, Alexandria, VA.
Non-final office action for U.S. Appl. No. 17/563,162 from the United States Patent and Trademark Office, Alexandria, VA.
Response filed Nov. 22, 2022 to Notice of Examination dated Sep. 29, 2011 in Pakistan Patent Application No. 803/2010.
Request for Continued Examination (RCE) transmittal for U.S. Appl. No. 16/090,360, filed Jun. 8, 2023 at the United States Patent and Trademark Office.
Transmission of the certificate for a European Patent pursuant to Rule 74 EPC for European Patent No. 3449921, issued by the European Patent Office dated May 31, 2023.
Notice of Allowance for U.S. Appl. No. 16/090,360, mailed by the United States Patent and Trademark Office dated Jun. 22, 2023.
Terminal Disclaimer filed at the United States Patent and Trademark Office dated Jun. 27, 2023 in U.S. Appl. No. 17/563,162.
Response to Jun. 13, 2023 Non-final Office Action for U.S. Appl. No. 17/563,162, response filed Jun. 29, 2023, 3 pages.
The extended European search report including the supplementary European search report and the European search opinion, for EP Appl. No. 20847524.4, dated Jun. 19, 2023, 10 pages, The European Patent Office, Munich Germany.
Amendment filed in Brazilian Patent Appl. No. BR 112021026170-2 dated Jun. 27, 2023.
Response filed in Chinese Patent Appl. No. CN 202080042486.9 dated Jul. 4, 2023.
Corrected Notice of Allowability in United States U.S. Appl. No. 16/090,360, dated Dec. 9, 2022, 2 pages.
Office action in Japanese Patent Application No. 2017-546075, dated Jul. 21, 2020, 6 pages (with English translation).
Notice of Allowance in U.S. Appl. No. 16/835,719, dated Jun. 14, 2021, 8 pages.
Notice of Allowance in U.S. Appl. No. 17/067,302, dated May 28, 2021, 8 pages.
Notice of Allowance in South African Patent Appl. No. 2021/10686, dated Jul. 8, 2022.
Applicant-Initiated Interview Summary for U.S. Appl. No. 17/563,162, dated Aug. 18, 2022, 2 pages.
Response (arguments and amendment) filed Aug. 26, 2022 in U.S. Appl. No. 17/563,162, 6 pages.
Arguments and amendment filed Sep. 28, 2022 in U.S. Appl. No. 17/563,162, 6 pages.
Amendment after Notice of Allowance filed Sep. 29, 2022 in U.S. Appl. No. 17/563,162, 6 pages.
Applicant-initiated Interview Summary for U.S. Appl. No. 17/563,162, for interview of Sep. 29, 2022, 1 page.
USPTO response to amendment under rule 312, dated Oct. 7, 2022 in U.S. Appl. No. 17/563,162.
Office action in Israeli Appl. No. 254133 dated Oct. 14, 2020.
Azuma, K., et al., "The small cell lung cancer cohort of a Phase 2 Trial of E7389-LF (liposome formulation of eribulin) + Nivolumab," Poster Presentation at the Am. Soc for Clinical Oncology Symposium, Jun. 2-6, 2023, Chicago, IL, Abstract No. 8593, https://ascopubs.org/doi/abs/10.1200/JCO.2023.41.16_suppl.8593.
Azuma, K., et al., "Phase 2 small cell lung cancer (SCLC) cohort of a phase 1b/2 trial of a liposome formulation of eribulin in combination with nivolumab," Abstract 8593, Meeting Abstract I, 2023, ASCO Annual Meeting I, Journal of Clinical Oncology 41, No. 16_suppl (Jun. 1, 2023) 8593-8593. published online May 31, 2023, https://ascopubs.org/doi/abs/10.1200/JCO.2023.41.16_suppl.8593.
Final Office action, for U.S. Appl. No. 17/563,162, dated Aug. 24, 2023, from the United States Patent and Trademark Office, Alexandria, VA, 7 pages.
Non-Final Office action, for U.S. Appl. No. 17/563,162, dated Jun. 10, 2022, from the United States Patent and Trademark Office, Alexandria, VA.
Topalian, S. et al., "Safety, activity, and immune correlates of anti-PD-1 antibody in cancer," New English Journal of Medicine, Jun. 2012, 366(26): 2443-2454.
[No Author] WHO Drug Information, 2013, vol. 27, No. 1, pp. 68-69.
[No Author] WHO Drug Information, 2013, vol. 27, No. 2, pp. 161-162.
Adams, S. et al., "Phase 2 study of pembrolizumab (pembro) monotherapy for previously treated metastatic triple-negative breast cancer (mTNBC): KEYNOTE-086 cohort A," J Clin Oncol 35, No. 15 suppl (May 20, 2017), abstract 1008 (4 pages), doi:10.1200/JCO.2017.35.15_suppl.1008.
Adams, S. et al., "Phase 2 study of pembrolizumab as first-line therapy for PD-L1-positive metastatic triple-negative breast cancer (mTNBC): Preliminary data from KEYNOTE-086 cohort B," Journal of Clinical Oncology 35, No. 15_suppl (May 20, 2017) abstract 1088, DOI: 10.1200/JCO.2017.35.15_suppl.1088 (Meeting abstract: 2017 ASCO Annual Meeting.
Ahmadzadeh M, et al., "Tumor antigen-specific CD8 T cells infiltrating the tumor express high levels of PD-1 and are functionally impaired." Blood. Aug. 2, 20090;114(8): 1537-44. doi: 10.1182/blood-2008-12-195792. Epub May 7, 2009.
Asano M, et al., "Broad-spectrum Preclinical Antitumor Activity of Eribulin (Halaven®): Combination with Anticancer Agents of Differing Mechanisms." Anticancer Res. Jun. 2018;38(6):3375-3385. doi: 10.21873/anticanres. 12604.
Cardoso F, et al.,. "ESO-ESMO 2nd international consensus guidelines for advanced breast cancer (ABC2)." Breast. Oct. 2014;23(5):489-502.doi: 10.1016/j.breast.2014.08.009. Epub Sep. 20, 2014.
ClinicalTrials.gov [online] "Study NCT01848834—Study of MK-3475 in participants with advanced solid tumors (MK-3475-012/KEYNOTE-012," Apr. 2014, retrieved from: URL https://clinicaltrials.gov/ct2/history/NCT01848834?V_24=View>, 7 pages.
Coates AS, et al. "Tailoring therapies—improving the management of early breast cancer: St Gallen International Expert Consensus on the Primary Therapy of Early Breast Cancer 2015." Ann Oncol. Aug. 2015;26(8): 1533-46. doi: 10.1093/annonc/mdv221. Epub May 4, 2015.
Cortes J, et al. "Eribulin monotherapy versus treatment of physician's choice in patients with metastatic breast cancer (EMBRACE): a phase 3 open-label randomised study." Lancet. Mar. 1, 20112;377(9769): 914-23. doi: 10.1016/S0140-6736(11)60070-6. Epub Mar. 2, 2011.
[No. author] CTEP Rapid Communication, "Solicitation for Letters of Intent: Clinical trials—Preclinical experiments, E7389, Halichondrin B analog (NSC 707389)," 2005, 11 pages.
Devriese LA, et al., "Eribulin mesylate pharmacokinetics in patients with solid tumors receiving repeated oral ketoconazole." Invest New Drugs. Apr. 2013;31(2):381-9. doi: 10.1007/s10637-012-9829-3. Epub May 5, 2012.
Dong H, et al., "Tumor-associated B7-H1 promotes T-cell apoptosis: a potential mechanism of immune evasion." Nat Med. Aug. 2002;8(8):793-800. doi: 10.1038/nm730. Epub Jun. 24, 2002.

(56) References Cited

OTHER PUBLICATIONS

Dybdal-Hargreaves NF, et al. "Eribulin mesylate: mechanism of action of a unique microtubule-targeting agent." Clin Cancer Res. Jun. 1, 2015;21(11):2445-52. doi: 10.1158/1078-0432.CCR-14-3252. Epub Apr. 2, 2015.
Eisai Co., Ltd., "FY2011 Financial Results Presentation," May 15, 2012, 68 pages (with English translation).
Eisai Co., Ltd., "Halaven®," Intravenous Injection 1 mg, CODE DI-T-HAL107, 6th edition, Feb. 2016, pp. 1-16 (with English Translation).
Eisai Co., Ltd., "Material Safety Data Sheet for Eribulin Mesylate," Oct. 2009, prepared by Greg Baker, 6 pages.
Gao Q, et al., "Overexpression of PD-L1 significantly associates with tumor aggressiveness and postoperative recurrence in human hepatocellular carcinoma." Clin Cancer Res. Feb. 1, 2009;15(3):971-9. doi: 10.1158/1078-0432.CCR-08-1608.
Ghebeh H, et al., "FOXP3+ Tregs and B7-H1+/PD-1+ T lymphocytes co-infiltrate the tumor tissues of high-risk breast cancer patients: Implication for immunotherapy." BMC Cancer. Feb. 23, 2008;8:57. doi: 10.1186/1471-2407-8-57.
Ghebeh H, et al., "The B7-H1 (PD-L1) T lymphocyte-inhibitory molecule is expressed in breast cancer patients with infiltrating ductal carcinoma: correlation with important high-risk prognostic factors." Neoplasia. Mar. 2006;8(3):190-8. doi: 10.1593/neo.05733.
Golub TR, et a. "Molecular classification of cancer: class discovery and class prediction by gene expression monitoring." Science. Oct. 15, 1999;286(5439):531-7. doi: 10.1126/science.286.5439.531.
Hamanishi J, et al., "Programmed cell death 1 ligand 1 and tumor-infiltrating CD8+ T lymphocytes are prognostic factors of human ovarian cancer." Proc Natl Acad Sci U S A. Feb. 27, 2007;104(9):3360-5. doi: 10.1073/pnas.0611533104. Epub Feb. 21, 2007.
Hino R, et al., "Tumor cell expression of programmed cell death-1 ligand 1 is a prognostic factor for malignant melanoma." Cancer. Apr. 1, 2010;116(7): 1757-66. doi: 10.1002/cncr.24899.
Inman BA, et al., "PD-L1 (B7-H1) expression by urothelial carcinoma of the bladder and BCG-induced granulomata: associations with localized stage progression." Cancer. Apr. 15, 2007;109(8): 1499-505. doi: 10.1002/cncr.22588.
International Preliminary Report on Patentability for International Application No. PCT/US2016/020734, dated Sep. 5, 2017, dated Sep. 14, 2017, 9 pages.
International Preliminary Report on Patentability for International Application No. PCT/US2017/056552, dated Apr. 16, 2019, dated Apr. 25, 2019, 8 pages.
International Search Report and Written Opinion for International Application No. PCT/US2017/056552, dated Jan. 2, 2018, 11 pages.
International Search Report and Written Opinion for International Application No. PCT/US2016/020734, dated Apr. 28, 2016, 7 pages.
Knollman H, et al., "Muscle-invasive urothelial bladder cancer: an update on systemic therapy." Ther Adv Urol. Dec. 2015;7(6):312-30. doi: 10.1177/1756287215607418.
Merck Sharp & Dohme Corp., "Highlights of Prescribing Information—KEYTRUDA® (pembrolizumab)," Label, Supp. 8, revised Oct. 2016, FDA Ref. ID: 4003165, retrieved from: URL<https://www.accessdata.fda.gov/drugsatfda_docs/label/2016/125514s008s0121b1.pdf>, 29 pages.
Merck Sharp & Dohme Corp., "Highlights of Prescribing Information—KEYTRUDA® (pembrolizumab)," Label, Supp. 9, revised Aug. 2016, FDA Ref. ID: 3968676, retrieved from: URL<https://www.accessdata.fda.gov/drugsatfda_docs/label/2016/125514s0091b1.pdf>, 26 pages.
Nakanishi J, et al., Overexpression of B7-H1 (PD-L1) significantly associates with tumor grade and postoperative prognosis in human urothelial cancers. Cancer Immunol Immunother. Aug. 2007;56(8): 1173-82. doi: 10.1007/s00262-006-0266-z. Epub Dec. 2, 20062.

Nanda R, et al., "Pembrolizumab in Patients With Advanced Triple-Negative Breast Cancer: Phase Ib KEYNOTE-012 Study." J Clin Oncol. Jul. 20, 2016;34(21):2460-7. doi: 10.1200/JCO.2015.64.8931. Epub May 2, 2016.
[No. author] "Pembrolizumab Shows Potential in Breast Cancer," Cancer Discovery, 2015, 5(2): 100-101, published online Dec. 15, 2014.
Nomi T, et al., "Clinical significance and therapeutic potential of the programmed death-1 ligand/programmed death-1 pathway in human pancreatic cancer." Clin Cancer Res. Apr. 1, 2007;13(7):2151-7. doi: 10.1158/1078-0432.CCR-06-2746.
Office action in Chinese Patent Application No. 201680025588.3, dated Jan. 6, 2020, 28 pages, with English translation.
Office Action in European Patent Application No. 16710891.9, dated Aug. 13, 2019, 6 pages.
Office Action in European Patent Application No. 16710891.9, dated Mar. 31, 2020, 6 pages.
Office Action in Indian Patent Application No. 201747034283, dated Feb. 28, 2020, 7 pages, with English translation.
Office Action in Japanese Patent Application No. 2017-546075, dated Jan. 7, 2020, 6 pages, with English translation.
Office Action in Russian Patent Application No. 2017132877, dated Aug. 29, 2019, 12 pages, with English translation.
Office Action in United States U.S. Appl. No. 16/835,719, dated Jun. 29, 2020, 15 pages.
Ohigashi Y, et al., "Clinical significance of programmed death-1 ligand- 1 and programmed death-1 ligand-2 expression in human esophageal cancer." Clin Cancer Res. Apr. 1, 20055;11(8):2947-53. doi: 10.1158/1078-0432.CCR-04-1469.
Opposition in Columbian Patent Application No. 11-130828, dated Jul. 25, 2012, 14 pages, with English translation.
Pardoll DM. "The blockade of immune checkpoints in cancer immunotherapy." Nat Rev Cancer. Mar. 22, 2012; 12(4):252-64. doi: 10.1038/nrc3239.
Sharpe AH, et al., "The function of programmed cell death 1 and its ligands in regulating autoimmunity and infection." Nat Immunol. Mar. 2007;8(3):239-45. doi: 10.1038/ni1443.
Shimauchi T, et al., "Augmented expression of programmed death-1 in both neoplastic and non-neoplastic CD4+ T-cells in adult T-cell leukemia/lymphoma." Int J Cancer. Dec. 15, 2007;121(12):2585-90. doi: 10.1002/ijc.23042.
Thompson RH, et al., "PD-1 is expressed by tumor-infiltrating immune cells and is associated with poor outcome for patients with renal cell carcinoma." Clin Cancer Res. Mar. 15, 2007;13(6):1757-61. doi: 0.1158/1078-0432.CCR-06-2599.
Thompson RH, et al., "Significance of B7-H1 overexpression in kidney cancer." Clin Genitourin Cancer. Dec. 2006;5(3):206-11. doi: 10.3816/CGC.2006.n.038.
Tolaney et al., "Phase 1b/2 study to evaluate eribulin mesylate in combination with pembrolizumab in patients with metastatic triple-negative breast cancer,": [Abstract No. 177], Jan. 28, 2017, Eur. J. Cancer, 2017, 72:S16.
Written Opinion in International Patent Application No. PCT/JP2016/020734, dated Aug. 28, 2018, 8 pages.
Written Opinion in Singaporean Patent Application No. 11201706872S, dated Jun. 27, 2018, 7 pages.
Written Opinion in Singaporean Patent Application No. 11201706872S, dated Nov. 5, 2019, 10 pages.
Yang W, et al., "PD-L1: PD-1 interaction contributes to the functional suppression of T-cell responses to human uveal melanoma cells in vitro." Invest Ophthalmol Vis Sci. Jun. 2008;49(6):2518-25. doi: 10.1167/iovs.07-1606. Epub Feb. 22, 2008.
Yi M, et al., "Biomarkers for predicting efficacy of PD-1/PD-L1 inhibitors." Mol Cancer. Aug. 23, 2018;17(1): 129. doi: 10.1186/s12943-018-0864-3.
Zibelman M, et al., "Checkpoint Inhibitors and Urothelial Carcinoma: The Translational Paradigm." Oncology (Williston Park). Feb. 2016;30(2):160-2, 176.
Tolaney, SM et al., Phase 1b/2 study to evaluate eribulin mesylate in combination with pembrolizumab in patients with metastatic triple-negative breast cancer [abstract]. In Proceedings of the 2017

(56) References Cited

OTHER PUBLICATIONS

San Antonio Breast Cancer Symposium; Dec. 5-9, 2017 San Antonio, TX. Philadelphia (PA): AACR; Cancer Res 2018; 78(4 Supp):Abstract No. PD6-13.
Rejection Decision for CN Application No. 202080042486.9, dated Aug. 22, 2023.
Nih.gov [Online], "Nivolumab," Year introduced: 2019 (2010), [Retrieved on Jun. 4, 2022], retrieved from: URL<https://www.ncbi.nlm.nih.gov/mesh/?term=BMS-936558>, 2 pages.
Submission document: Response to restriction requirement in U.S. Appl. No. 17/563,162, dated May 31, 2022, 4 pages.
Communication pursuant to Article 94(3) EPC in European Patent Application No. 16710891.9, dated Nov. 16, 2020, 24 pages.
Letters Patent for the Brazilian Patent No. PI 1014527-3, granted on Nov. 24, 2020, 70 pages (with English Translation).
Notice of intention to Refuse Patent Application in Singaporean Patent Application No. 11201706872S, dated Nov. 19, 2020, 11 pages.
Office action in Mexican Patent Application No. MX/a/2017/011206, dated Nov. 24, 2020, 8 pages (with partial translation).
Response filed in U.S. Appl. No. 16/835,719, dated Nov. 2, 2020, 7 pages.
ClinicalTrials.gov [online], "A Study of E7389 Liposomal Formulation (E7389-LF) Plus Nivolumab in Participants with Solid Tumor, History of Changes for Study: NCT04078295," Sep. 2019, retrieved from: URL<https://clinicaltrials.gov/ct2/history/NCT04078295?V_1=View#Study Page Top, Sep. 2, 2019, 4 pages.
Office action in Chinese Patent Application No. 201680025588.3, dated Jul. 7, 2020, 29 pages (with English translation).
Response filed in United States U.S. Appl. No. 16/835,719, dated Sep. 29, 2020, 10 pages.
Official Action for RU Patent Application No. 2021137703, from the Federal Service on Intellectual Property (Rospatent), dated Dec. 15, 2023.
Pokrovsky (Pokrovskii), V.I., Editor in Chief, "The Small Medical Encyclopedia, (Malaya Meditsinskaya Entsiklopediya)" vol. 4, pp. 81-83 (Renal Failure), and vol. 5, pp. 90-96, "Renal Stone Disease—Subscription," Moscow—"Medicine" 1996.
Kharkevitch D.A., "Textbook for medical students," 10th edition, Geotar-Media, 2010, (908 pages), pp. 1,2, 72-82.
Response to Official Communication dated Jul. 6, 2023 filed in counterpart European Patent Application No. 20847524.4 dated Dec. 6, 2023.
Response to Official Communication dated Sep. 18, 2023 filed in counterpart Indonesian Patent Application No. P00202111802 dated Dec. 8, 2023.
Request for Reexamination filed in counterpart Chinese Patent Application No. 2020800424869 dated Dec. 5, 2023.
Olson, B. et al., "Mouse Models for Cancer Immunotherapy Research," Cancer Discovery, 8 (11): 1358-1365 (Nov. 2018).
Office Action issued on Feb. 29, 2024, for Vietnamese Patent Application No. 1-2021-08263, by the Ministry for Science and Technology, Intellectual Property Office of Vietnam.
Action issued in Vitenamese Patent Application No. 1-2021-08263 dated Feb. 29, 2024.
Action issued in Taiwanese Patent Application No. 109125099 dated Mar. 25, 2024.
Kan Yonemori et al., "E7389-LF as a First-line Chemotherapy for Patients with Metastatic/Advanced HER2-Negative Breast Cancer: Results From a Phase 1 Study Dose-Expansion Part," Poster #: 405P, European Society for Medical Oncology (ESMO) annual meeting, Oct. 20-24, 2023, Madrid, Spain.
Akihito Kawazoe et al., "Phase II Study of the Liposomal Formulation of Eribulin (E7389-LF) in Combination with Nivolumab: Results from the Gastric Cancer Cohort," Clinical Cancer Research, Apr. 1, 2024, 30(7), p. 1264-p. 1272.
Makoto Nishio et al., "Phase 2 Study of the Liposomal Formulation of Eribulin (E7389-LF) in Combiation with Nivolumab: Results from the Small Cell Lung Cancer Cohort", Cancer Research Communications, Jan. 29, 2024;(1):226-235.
Hiroyuki Yasojima et al., "E7389-LF as 1L chemotherapy for advanced/metastatic HER2-negative breast cancer (HER2-BC): Phase 1 dose-expansion study, Abstract #: MO9-3", Japanese Society of Medical Oncology Annual Meeting, Feb. 22-24, 2024, Nagoya, Japan.
Hisato Kawakami et al., "Phase 2 small cell lung cancer cohort of liposomal eribulin given with nivolumab: Overall survival update, Abstract#: MO58-1", Japanese Society of Medical Oncology Annual Meeting, Feb. 22-24, 2024, Nagoya, Japan.
Akihito Kawazoe et al., "Results of a phase 2 trial of E7389-LF + nivolumab in patients with gastric or esophageal cancers, Abstract#: MO57-2", Japanese Society of Medical Oncology Annual Meeting, Feb. 22-24, 2024, Nagoya, Japan.
Moe Tamura et al., "Combination activity of eribulin liposomal formulation and anti-PD-1 antibody after tumor regrowth during anti-PD-1 antibody treatment in mice, Poster#L 2955", American Association for Cancer Research (AACR) Annuaml Meeting 2024, Apr. 5-10, 2024, San Diego, California.

\* cited by examiner

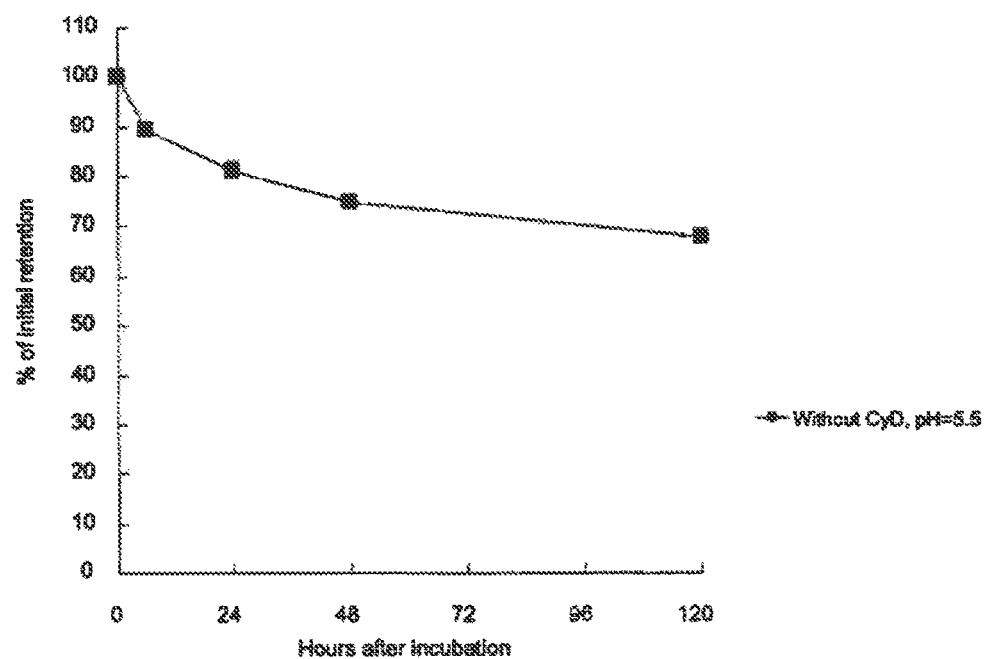
(Fig. 1)

(Fig. 2)
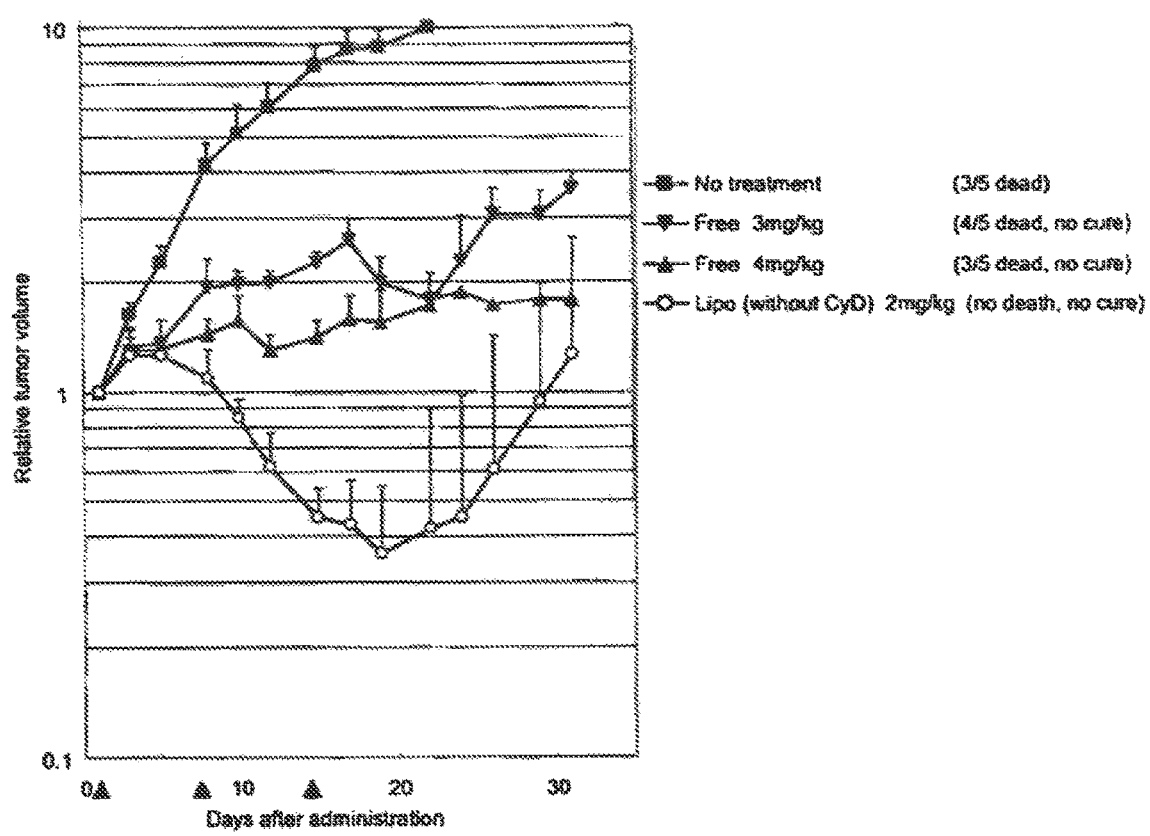

(Fig. 3)
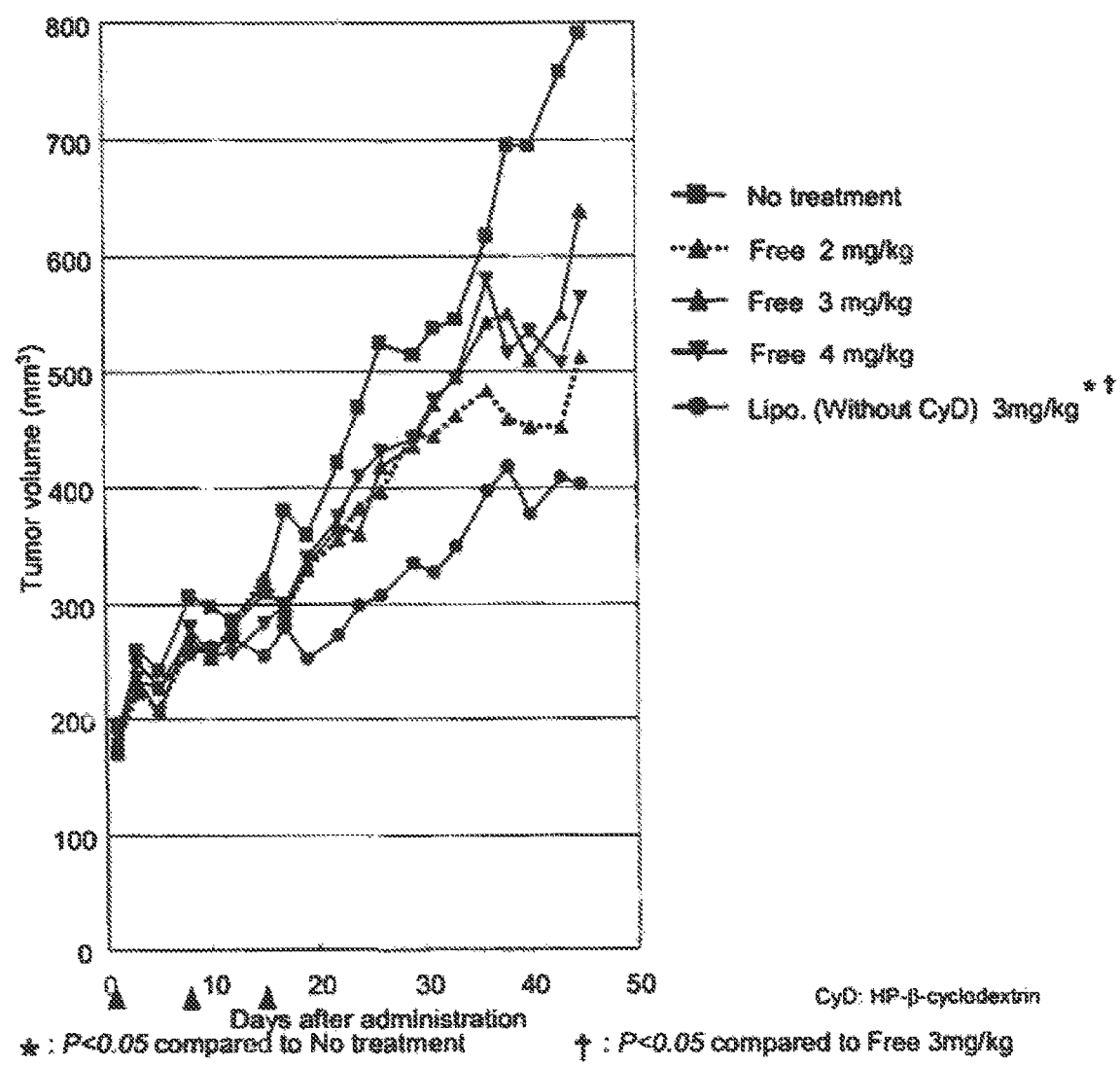

LIPOSOME COMPOSITION

RELATED APPLICATIONS

This application is a continuation of U.S. application. Ser. No. 13/260,872, 35 U.S.C. § 371 date Sep. 28, 2011 (abandoned), which is the U.S. national stage of International Application No. PCT/JP2010/055770, filed Mar. 30, 2010 (expired), which claims benefit to U.S. Provisional Application No. 61/164,653, filed Mar. 30, 2009 (expired), and priority to Japanese Application No. JP2009-082521, filed Mar. 30, 2009.

TECHNICAL FIELD

The present invention relates to a novel liposome composition containing eribulin or its pharmacologically permissible salt. The present invention also relates to a method of manufacture of the liposome composition.

BACKGROUND ART

Liposomes are microscopic closed vesicles having an internal phase enclosed by one or more lipid bilayers, and are capable of holding water-soluble material in the internal phase, and lipophilic material in the lipid bilayer. When entrapping an active compound in liposome, and delivering it to target tissue, how to entrap the active compound in the liposome with high efficiency, and how to secure stable retention of the active compound by the liposome constitute important issues.

When entrapping lipophilic compounds in liposome, a high entrapment ratio can be achieved relatively easily, but except in cases of compounds which have very high membrane affinity such as amphotericin B (the principal agent in the liposomal drug AmBisome), retention stability in blood plasma is ordinarily low, and it is difficult to obtain sufficient improvement in pharmacokinetics. With respect to methods for entrapping water-soluble compounds in liposome, there are various methods such as the lipid film method (Vortex method), reverse phase evaporation method, surfactant removal method, freeze-thaw method, and remote loading methods (pH gradient method, ion gradient method). However, it is only the remote loading methods that provide close to a 100% entrapment ratio; an entrapment ratio on the order of only 5 to 30% is obtained from the other methods.

As remote loading methods, those using a pH gradient and ammonium sulfate ion gradient are known. The pH gradient method, which is a remote loading method using a pH gradient, is a technique for incorporating compounds into liposome by using the movement of molecular/ionic dissociation equilibrium due to the pH of the target compound.

As one example of a compound entrapped in liposome by the pH gradient method, one may cite, for example, doxorubicin (DOX, pKa: 8.2). After preparing a liposome solution with a buffer solution of pH 4, the external phase of the liposome is replaced with a pH 7 buffer solution. In the case where DOX is added to this liposome solution, as the molecular DOX in the pH 7 solution is lipophilic, it migrates to the liposome membrane rather than to the aqueous phase. In the case where the DOX that has migrated to the liposome membrane further contacts the pH 4 internal phase of the liposome, it becomes ionic, and is incorporated into the internal phase of the liposome. In this way, DOX is transported from the external phase to the internal phase of liposome by a movement of dissociation equilibrium (see Non-patent Literature 1, Non-patent Literature 2, and Patent Literature 1).

A variety of techniques have been reported for improving this type of remote loading method. In Non-patent Literature 3, a technique is disclosed for improving the entrapment ratio of active compounds by adding ethanol together with the active compound to the external phase of the liposome, when the pH gradient method is conducted in liposome of special composition called cholesterol-free liposome.

In Patent Literature 2, in addition to the pH gradient, a technique is disclosed for improving the entrapment ratio of active compounds by having copper ions exist in the internal phase of the liposome.

Instead of a pH gradient in the pH gradient method, the ammonium sulfate method, which is a remote loading method using an ammonium sulfate ion gradient, is a technique for incorporating active compounds into the internal phase of liposome by using an ion gradient such as bivalent ammonium sulfate (see Non-patent Literature 1 and Patent Literature 3).

In addition to an ion gradient based on ammonium sulfate, Patent Literature 4 discloses a technique for incorporating active compounds into liposome by adding boronic acid together with the active compound to the external phase of the liposome Instead of an ion gradient based on ammonium sulfate, Patent Literature 5 discloses a technique wherein, compared to the case where ammonium sulfate is used, the release rate of the active compound is improved by incorporating the active compound into liposome using an ion gradient of glucuronic acid anion.

Thus, from the standpoint of entrapment ratio, remote loading methods are excellent entrapment methods. However, in the case where remote loading methods are used, except for special cases such as Doxil (a liposome preparation of DOX) where the active compound entrapped in the internal phase of the liposome is crystallized, there is the problem that the active compound tends to leak from the liposome in blood plasma, and that retention stability of the active compound is low.

As described above, with conventional technical methods, the current situation is that it is difficult to achieve coexistence of a high entrapment ratio of the active compound in liposome and retention stability of the active compound in liposome.

PRIOR ART LITERATURE

Patent Literatures

Patent Literature 1: U.S. Pat. No. 5,192,549, Specification
Patent Literature 2: PCT international Publication WO 2006/037230, Pamphlet
Patent Literature 3: U.S. Pat. No. 5,316,771, Specification
Patent Literature 4: U.S. Pat. No. 6,051,251, Specification
Patent Literature 5: PCT International Publication WO 2005/046643, Pamphlet

Non-Patent Literatures

Non-patent Literature 1: Yasuyuki Sazuka, "Liposome Preparation Method," "New Developments in Liposome Application: Toward the Development of Artificial Cells" (Kazunari Akiyoshi, Shigeru Tsujii, editorial supervision)" NTS, (2005), pp. 33-37.

Non-patent Literature 2: Mayer L D et al., Biochimica et Biophysica Acta, (1986), 857: pp. 123-426.
Non-patent Literature 3: N. Dos Santos et al Biochimica et Biophysica Acta (2004), 1661(1): pp. 47-60.

OUTLINE OF THE INVENTION

Problem to Be Solved by the Invention

The object of the present invention is to provide a liposome composition with a high entrapment ratio and retention stability of the active compound.

Means for Solving the Problem

As a result of diligent research aimed at solving the aforementioned problems, the present inventors discovered, with respect to a liposome composition whose active compound is eribulin or its pharmacologically permissible salt, that the entrapment ratio and retention stability of the active compound in the liposome composition are extremely high, thereby perfecting the present invention.

Namely, the present invention is as follows.

(1)
A liposome composition containing liposome, and containing an active compound in the liposome internal phase, wherein the active compound is eribulin or its pharmacologically permissible salt.

(2)
The liposome composition according to 1, wherein the liposome composition is in a solid or a liquid form.

(3)
The liposome composition according to 1 or 2, wherein the liposome internal phase further contains ammonium salt.

(4)
The liposome composition according to 3, wherein the concentration of the aforementioned ammonium salt is 10 mM or higher.

(5)
The liposome composition according to any one of 1 to 4, wherein the liposome internal phase further contains salt, acid, base and/or amino acid.

(6)
The liposome composition according to 5, wherein the concentration of the aforementioned salt is 1 to 300 mM.

(7)
The liposome composition according to 5 or 6, wherein the concentration of the aforementioned acid is 1 to 300 mM.

(8)
The liposome composition according to any one of 5 to 7, wherein the concentration of the aforementioned amino acid is 1 to 300 mM.

(9)
The liposome composition according to any one of 5 to 8, wherein the concentration of the aforementioned base is 1 to 300 mM.

(10)
The liposome composition according to any one of 1 to 9, wherein the concentration of the aforementioned active compound is 0.01 to 300 mg/mL.

(11)
The liposome composition according to any one of 1 to 10, wherein the aforementioned active compound is eribulin mesylate.

(12)
The liposome composition according to any one of 1 to 11, wherein the liposome internal phase further contains ammonium sulfate, citric acid, and an active compound.

(13)
The liposome composition according to any one of 1 to 12, wherein the liposome external phase contains sugar, electrolyte, and/or amino acid.

(14)
The liposome composition according to any one of 1 to 13, wherein the liposome external phase contains sugar or electrolyte, and amino acid.

(15)
The liposome composition according to 13 or 14, wherein the concentration of the aforementioned sugar is 2 to 20%.

(16)
The liposome composition according to any one of 13 to 15, wherein the concentration of the aforementioned amino acid is 1 to 300 mM.

(17)
The liposome composition according to any one of 1 to 16, wherein the liposome external phase contains sucrose or sodium chloride, and histidine.

(18)
The liposome composition according to any one of 1 to 17, wherein the aforementioned liposome internal phase does not substantially contain cyclodextrin.

(19)
The liposome composition according to any one of 1 to 18, wherein the liposome contains hydrogenated phosphatidylcholine.

(20)
The liposome composition according to any one of 1 to 19, wherein the liposome contains cholesterol.

(21)
The liposome composition according to any one of 1 to 20, wherein the liposome contains methoxypolyethylene glycol condensate.

(22)
The liposome composition according to 21, wherein the aforementioned methoxypolyethylene glycol condensate is distearoylphosphatidyl ethanolamino polyethylene glycol condensate.

(23)
The liposome composition according to any one of 1 to 22, wherein the liposome contains hydrogenated phosphatidylcholine, cholesterol, and distearoylphosphatidyl ethanolamino polyethylene glycol condensate.

(24)
The liposome composition according to 23, which contains 10 to 80% of the aforementioned hydrogenated phosphatidylcholine, 1 to 60% of the aforementioned cholesterol, and 0 to 50% of the aforementioned distearoylphosphatidyl ethanolamino polyethylene glycol condensate.

(25)
The liposome composition according to any one of 1 to 24, wherein the liposome contains hydrogenated soy phosphatidylcholine, cholesterol, and polyethylene glycol 2000-phosphatidylethanolamine.

(26)
A method of manufacture of the liposome composition according to any one of 1 to 25, including: a step in which a liposome dispersion liquid containing liposome is provided;
a step in which the aforementioned liposome dispersion liquid is mixed with the aforementioned active compound; and a step in which the aforementioned active compound is introduced into the liposome internal phase of the aforementioned liposome dispersion liquid.

(27)

The method according to 26, wherein the aforementioned liposome dispersion liquid does not substantially contain ammonium salt in the liposome external phase.

(28)

The method according to 26 or 27, wherein the pH of the liposome external phase of the aforementioned liposome dispersion liquid is 3 to 10.

(29)

The method according to any one of 26 to 28, wherein the pH of the liposome external phase of the aforementioned liposome dispersion liquid is 7 to 10.

(30)

The method according to 28 or 29, wherein the aforementioned pH is the pH of the liposome external phase of the aforementioned liposome dispersion liquid in the step in which the aforementioned liposome dispersion liquid and the aforementioned active compound are mixed.

(31)

The method according to any one of 26 to 30, wherein the step in which the aforementioned liposome dispersion liquid is provided includes: a step in which a liposome preparatory solution is provided that contains liposome and that contains ammonium salt in the liposome internal phase and liposome external phase; and a step in which the liposome external phase of the aforementioned liposome preparatory solution is substituted or diluted.

(32)

The method according to 31, wherein the step in which the aforementioned liposome external phase is substituted or diluted is a step in which the pH of the liposome external phase is made higher than the pH of the liposome internal phase.

(33)

The method according to 31 or 32, wherein the step in which the aforementioned liposome external phase is substituted or diluted is a step in which the difference between the pH of the liposome internal phase and the pH of the liposome external phase is 1 to 5.

(34)

The method according to any one of 26 to 33, wherein the pH of the aforementioned liposome internal phase is 3 to 9.

(35)

The method according to any one of 26 to 34, wherein the pH of the aforementioned liposome internal phase is 4 to 9.

(36)

The method according to any one of 26 to 35, wherein the pH of the aforementioned liposome internal phase is 5 to 8.

(37)

The method according to any one of 26 to 36, wherein the liposome external phase is a solution that contains electrolyte in the step in which the aforementioned active compound is introduced.

(38)

The method according to any one of 26 to 37, wherein the aforementioned liposome dispersion liquid does not substantially contain cyclodextrin in the liposome internal phase.

(39)

The method according to any one of 26 to 38, which further contains a step in which the pH of the liposome external phase is neutralized.

Effect of the Invention

According to the present invention, it is possible to offer a novel liposome composition. The liposome composition of the present invention entraps an active compound in the liposome internal phase with a high degree of efficiency, and has a high retention stability of the active compound.

BRIEF DESCRIPTION OF THE DRAWINGS (FIG. 1) shows in vitro changes in the concentration of eribulin mesylate in a liposome composition in rat blood plasma (37° C.).

(FIG. 2) shows the in vivo antitumor activity of eribulin mesylate due to liposome in FaDu cancer-bearing nude mice.

(FIG. 3) shows the in vivo antitumor activity of eribulin mesylate due to liposome in ACHN cancer-bearing nude mice.

BEST MODE FOR CARRYING OUT THE INVENTION

The present invention is specifically described by modes for carrying out the invention, but the present invention is not limited to the following modes for carrying out the invention, and may be carried out with a variety of modifications.

The contents disclosed in the literature referenced in the present invention are incorporated into the present invention as reference.

DEFINITIONS

"Liposome" means microscopic closed vesicles having an internal phase enclosed by lipid bilayer. In the present invention, liposome includes small single-membrane liposome (SUV: small unilamellar vesicle), large single-membrane liposome (LUV: large unilamellar vesicle), still larger single-membrane liposome (GUV: giant unilamellar vesicle), multilayer liposome having multiple concentric membranes (MLV: multilamellar vesicle), liposome having multiple membranes that are not concentric, but irregular (MVV: multivesicular vesicle), etc.

"Liposome internal phase" means an aqueous region enclosed in the lipid bilayer of the liposome, and is used with the same meaning as "internal water phase" and "liposome internal water phase." "Liposome external phase" means the region not enclosed by the lipid bilayer of the liposome (that is, the region apart from the internal phase and the lipid bilayer) in the case where the liposome is dispersed in liquid.

"Liposome composition" means a composition that contains liposome and that further contains eribulin mesylate in the liposome internal phase. In the present invention, liposome composition includes both solid and liquid forms.

"Liposome dispersion liquid" means a composition containing liposome, and is a composition preceding the introduction of the active compound into the liposome internal phase.

"Liposome preparatory solution" means a composition containing liposome, and is a composition preceding adjustment of the liposome external phase for purposes of entrapping eribulin mesylate in the liposome internal phase.

"Liposome reagent" means a liposome dispersion liquid, in the case where it is in a liquid form. In the case where it is in a solid form, it means a reagent from which liposome dispersion liquid can be obtained by dissolution or suspension in a prescribed solvent. The solvent is described below. As described below, a solid liposome reagent can be obtained, for example, by drying a liposome dispersion liquid.

In the present specification, "the mixing of solid and liquid" includes the dissolution and suspension of the solid in the liquid, and mixing, dissolution and suspension are used in a mutually interchangeable manner. Similarly, solvent and dispersion medium are also used in a mutually interchangeable manner.

Moreover, the liposome composition, liposome dispersion liquid, liposome preparatory solution, and liposome reagent of the present invention do not substantially contain cyclodextrin. "To not substantially contain cyclodextrin" means that there is no addition of cyclodextrin. It is sufficient if cyclodextrin is not contained in a quantity in which improvement of the solubility (nominal solubility) of the active compound due to cyclodextrin is significantly observable, and even in the case where it is added in a quantity in which improvement in the solubility of the active compound is not significantly observable, it is not to be excluded from implementation of the present invention.

Furthermore, as a preferred mode of the present invention, "the liposome dispersion liquid not substantially containing ammonium salt in the liposome external phase" means that ammonium salt is not added to the liposome external phase of the liposome dispersion liquid. Addition of ammonium salt in a quantity which is within a range that can achieve the objective of the present invention is not to be excluded from implementation of the present invention. In the case where ammonium salt is contained in the liposome external phase of a liposome preparatory solution, it is possible to prepare a liposome dispersion liquid that does not substantially contain ammonium salt by substituting or diluting the liposome external phase of the liposome preparatory solution using a solution that does not substantially contain ammonium salt.

(Active Compound)

The active compound of the present invention is eribulin or its pharmacologically permissible salt (hereinafter sometimes referred to as "eribulin, etc."). There are no particular limitations on the pharmacologically permissible salt so long as eribulin and salt are formed, whether inorganic acid salt or organic acid salt. For example, one may cite hydrochloric acid salt, sulfuric acid salt, citrate, hydrobromic acid salt, hydroiodine acid salt, nitric acid salt, bisulfate, phosphoric acid salt, super phosphoric acid salt, isonicotinic acid salt, ascetic acid salt, lactic acid salt, salicic acid salt, tartaric acid salt, pantotenic acid salt, ascorbic acid salt, succinic acid salt, maleic acid salt, fumaric acid salt, gluconic acid salt, saccharinic acid salt, formic acid salt, benzoic acid salt, glutaminic acid salt, methanesulfonic acid salt, ethanesulfonic acid salt, benzenesulfonic acid salt, p-toluenesulfonic acid salt, pamoic acid salt (pamoate), and so on. Preferable among these are hydrochloric acid salt, sulfuric acid salt, acetic acid salt, phosphoric acid salt, citrate, and mesylic acid salt, and most preferable of all is mesylic acid salt. That is, the preferable active compound of the present invention is eribulin mesylate. Moreover, as pharmacologically permissible salt of eribulin, it is acceptable to use eribulin and salt of aluminum, calcium, lithium, magnesium, calcium [sic], sodium, zinc, and diethanolamine. Eribulin or its pharmacologically permissible salt is the compound or its salt recorded in the pamphlet of PCT International Publication WO 99/65894 or U.S. Pat. No. 6,214,865 (the contents recorded in these patents are incorporated herein by reference), and have pharmacological action including antitumor action and antimitotic action. Eribulin or its pharmacologically permissible salt exhibits antitumor action with respect to melanoma, fibrosarcoma, monocytic leukemia, colon cancer, ovarian cancer, breast cancer, bone cancer, prostate cancer, lung cancer, and ras-transformed, fibroblasts.

However, as active compounds that can be combined with eribulin, etc., one may choose from among compounds used in the fields of medicines (including diagnostic drugs), cosmetic products, food products, and so on. With respect to active compounds, it is acceptable to combine one or more compounds other than eribulin, etc.

As active compounds, one may cite low-molecular compounds, etc. Among these, compounds used as antitumor agents, antibacterial agents, anti-inflammatory agents, anti-myocardial infarction agents, and contrast agents are suitable.

With respect to the molecular weight of the active compound, a range of 100 to 2000 is preferable, a range of 200 to 1500 is more preferable, and a range of 300 to 1000 is even more preferable. Within these ranges, the liposome membrane permeability of the active compound is generally satisfactory, and the present invention may be suitably applied.

The active compounds include water-soluble compounds and lipophilic compounds, and so long as they are more or less soluble in water or aqueous solvents, the present invention may be applied.

There are no particular limitations on antitumor agents in the present invention, and one may cite, for example, camptothecin derivatives such as irinotecan hydrochloride, nogitecan hydrochloride, exatecan, RFS-2000, lurtotecan, BNP-1350, Bay-383441, PNU-166148, IDEC-132, BN-80915, DB-38, DB-81, DB-90, DB-91, CKD-620, T-0128, ST-1480, ST-1481, DRF-1042, DE-310; taxane derivatives such as docetaxel hydride, docetaxel, pacritaxel, IND-5109, BMS-184476, BMS-188797, T-3782, TAX-1011, SB-RA-31012, SBT-1514, and DJ-927; iphosphamide, nimstine hydrochloride, carvocon, cyclophosphamide, dacarbazine, thiotepa, busulfan, melfaran, ranimustine, estramustine phosphate sodium, 6-mercaptopurine riboside, enocitabine, gemcitabine hydrochloride, carmfar, cytarabine, cytarabine ocfosfate, tegafur, doxifluridine, hydroxycarbamide, fluorouracil, methotrexate, mercaptopurine, fludarabine phosphate, actinomycin D, aclarubicin hydrochloride, idarubicin hydrochloride, pirarubicin hydrochloride, epirubicin hydrochloride, daunorubicin hydrochloride, doxorubicin hydrochloride, epirubicin, pirarubicin, daunorubicin, doxorubicin, pirarubicin hydrochloride, bleomycin hydrochloride, zinostatin stimalamer, neocarzinostatin, mitomycin C, bleomycin sulfate, peplomycin sulfate, etoposide, vinorelbine tartrate, vincrestine sulfate, vindesine sulfate, vinblastine sulfate, amrubicin hydrochloride, gefinitib, exemestane, capecitabine, TNP-470, TAK-165, KW-2401, KW-2170, KW-2871, KT-5555, KT-8391, TZT-1027, S-3304, CS-682, YM-511, YM-598, TAT-59, TAS-101, TAS-102, TA-106, FK-228, FK-317, E7070, (8E, 12E,14E)-7-[(4-cycloheptypiperazine-1-yl)carbonyl]oxy-3, 6,16,21-tetrahydroxy-6,10,12,16,20-pentamethyl-18,19-epoxytricosa-8,12,14-trien-11-olide (E7107), KRN-700, KRN-5500, J-107088, HMN-214, SM-11355, ZD-0473, etc. With respect to the compounds recorded as salts among the aforementioned antitumor agents, any salt is acceptable, and free bodies are also acceptable. With respect to compounds recorded as free bodies, any salt is acceptable.

There are no particular limitations on antibacterial agents, and one may cite, for example, amfotericine B, cefotiam hexyl, cephalosporin, chloramphenicol, diclofenac, etc. With respect to compounds of the aforementioned antibacterial agents, any salt is acceptable.

There are no particular limitations on anti-inflammatory agents, and one may cite, for example, prostaglandins (PGE1, PGE2), dexamethasone, hydrocortisone, pyroxicam, indomethacin, prednisolone, etc. With respect to compounds of the aforementioned anti-inflammatory agents, any salt is acceptable.

There are no particular limitations on anti-myocardial infarction agents, and one may cite, for example, adenosine, atenolol, pilsicamide, etc., and as contrast agents, one may cite, for example, iopamidol, ioxaglic acid, iohexyl, iomeprol, etc. With respect to compounds of the aforementioned anti-myocardial infarction agents and contrast agents, any salt is acceptable.

(Lipids)

It is preferable that the membrane constituents of the liposome of the present invention include phospholipids and/or phospholipid derivatives. As phospholipids and phospholipid derivatives, one may cite, for example, phosphatidyl ethanolamine, phosphatidyl choline, phosphatidyl serine, phosphatidyl inositol, phosphatidyl glycerol, cardiolipin, sphingomyelin, ceramide phosphorylethanolamine, ceramide phosphoryl glycerol, ceramide phosphoryl glycerol phosphate, 1,2-dimyristoyl-1,2-deoxyphosphatidyl choline, plasmalogen, phosphatidic acid, etc. It is also acceptable to combine one or more of these phospholipids and phospholipid derivatives.

There are no particular limitations on fatty-acid residues in the phospholipids and phospholipid derivatives, and one may cite, for example, saturated or unsaturated fatty-acid residue with a carbon number of 12 to 20. Specifically, one may cite acyl groups derived from fatty-acid such as lauric acid, myristic acid, palmitic acid, stearic acid, oleic acid, and linoleic acid. One may also use phospholipids derived from natural substances such as egg-yolk lecithin and soy lecithin, partially hydrogenated egg-yolk lecithin, (completely) hydrogenated egg-yolk lecithin, partially hydrogenated soy lecithin, and (completely) hydrogenated soy lecithin whose unsaturated fatty-acid residues are partially or completely hydrogenated, etc.

There are no particular limitations on the mixing amount (mole fraction) of the phospholipids and/or phospholipid derivatives that are used when preparing the liposome, but 10 to 80% relative to the entire liposome membrane composition is preferable, and 30 to 60% is more preferable.

With respect to membrane constituents, apart from phospholipids and/or phospholipid derivatives, the liposome of the present invention may also include sterols such as cholesterol and cholestenol as membrane stabilizers, fatty acids having saturated or unsaturated acyl groups with a carbon number of 8 to 22, and antioxidants such as α-tocopherol.

There are no particular limitations on the mixing amount (mole fraction) of these sterols that are used when preparing the liposome, but 1 to 60% relative to the entire liposome membrane composition is preferable, 10 to 50% is more preferable, and 30 to 50% is even more preferable.

Moreover, there are no particular limitations on the mixing amount (mole fraction) of the fatty acids, but 0 to 30% relative to the entire liposome membrane composition is preferable, 0 to 20% is more preferable, and 0 to 10% is even more preferable. With respect to the mixing amount (mole fraction) of the antioxidants, it is sufficient if an amount is added that can obtain the antioxidant effect, but 0 to 15% of the entire liposome membrane composition is preferable, 0 to 10% is more preferable, and 0 to 5% is even more preferable.

The liposome of the present invention may also contain functional lipids and modified lipids as membrane constituents.

As functional lipids, one may cite lipid derivatives retained in blood, temperature-sensitive lipid derivatives, pH-sensitive lipid derivatives, etc. As modified lipids, one may cite PEG lipids, sugar lipids, antibody-modified lipids, peptide-modified lipids, etc.

As lipid derivatives retained in blood, one may cite, for example, glycophorin, ganglioside GM1, ganglioside GM3, glucuronic acid derivatives, glutaminic acid derivatives, polyglycerin phospholipid derivatives, polyethylene glycol derivatives (methoxypolyethylene glycol condensates, etc.) such as N-[carbonyl-methoxy polyethylene glycol-2000]-1, 2-dipalmitoyl-sn-glycero-3-phosphoethanolamine, N-[carbonyl-methoxy polyethylene glycol-5000]-1,2-dipalmitoyl-sn-glycero-3-phosphoethanolamine, N-[carbonyl-methoxy polyethylene glycol-750]-1,2-distearoyl-sn-glycero-3-phosphoethanolamine, N-[carbonyl methoxy polyethylene glycol-2000]-1,2-distearoyl-sn-glycero-3-phosphoethanolamine (MPEG 2000-distearoyl phosphatidyl ethanolamine), and N-[carbonyl-methoxy polyethylene glycol-5000]-1,2-distearoyl-sn-glycero-3-phosphoethanolamine, which are condensates of phosphoethanolamine and methoxy polyethylene glycol. By having the liposome contain lipid derivatives with blood retention properties, it is possible to improve the blood retention of the liposome, because the liposome becomes difficult to capture in the liver, etc. as a foreign impurity.

As temperature-sensitive lipid derivatives, one may cite, for example, dipalmitoyl phosphatidylcholine, etc. By having the liposome contain temperature-sensitive lipid derivatives, it is possible to cause destruction of liposome at specific temperatures, and cause changes in the surface properties of the liposome. Furthermore, by combining this with an increase in temperature at the target site of the tumor, etc., it is possible to destroy the liposome at the target site, and release the active compound at the target site.

As pH-sensitive lipid derivatives, one may cite, for example, dioleoyl phosphatidyl ethanolamine, etc. By having the liposome contain pH-sensitive lipid derivatives, it is possible to promote membrane fusion of liposome and endosome when the liposome is incorporated into cells due to the endocytosis, and improve transmission of the active compound to cytoplasm.

As sugar lipids, antibody-modified lipids, and peptide-modified lipids, one may cite lipids that are bonded with sugars, antibodies, or peptides that are compatible with the target cells or target tissue. By using modified lipids, the liposome can be actively transmitted to the target cells or target tissue.

There are no particular limitations on the mixing amount (mole fraction) of lipid derivatives with blood retention properties used when preparing the liposome, but 0 to 50% of the entirety of liposome membrane constituent lipids is preferable, 0 to 30% is more preferable, and 0 to 20% is even more preferable.

(Liposome)

As mentioned above, liposome is a microscopic closed vesicle having an internal phase enclosed by a lipid bilayer.

Ideally, with respect to the liposome, a) it is preferable that the liposome has a barrier function that prevents leakage of eribulin, etc to the liposome external phase after the eribulin, etc. is once entrapped in the internal phase of the liposome. In the case where it is used as a medicine, it is preferable that the liposome exhibits in vivo stability, and that the liposome has a barrier function that prevents leakage of eribulin, etc to the liposome external phase in blood when the liposome is administered in vivo.

The composition of membrane constituents for liposome having such membrane permeability at a level allowing practical application can be appropriately selected by those skilled in the art according to the active compound, target tissue and the like by referencing as necessary the embodiments described below (Hiroshi Kikuchi, et. al, "Liposome I—Preparation Method and Assay Method—," Cell Technology (1983), 2(9): pp. 1136-1149, and reference literature cited in said literature).

When used as a medicine, it is preferable that the eribulin, etc. be released from the liposome after the liposome reaches the target tissue, cells, or intracellular organelles. With respect to liposome, the membrane constituents themselves are ordinarily biodegradable, and ultimately decompose in target tissue or the like. It is thought that the entrapped eribulin, etc. is released in this manner. Moreover, it is also acceptable if the liposome itself is incorporated into cells.

Not only can the liposome composition be targeted to target tissue such as solid cancer, but it can also be used to transmit active compounds to hematological cancer and so on. It can also be used as a slow release formulation, controlled release formulation, etc. in blood.

The particle size of liposome can be set according to the objective. For example, when it is intended to transmit liposome to cancerous tissue or inflamed tissue by the EPR (Enhanced Permeability and Retention) effect as an injection product or the like, it is preferable that liposome particle size be 30 to 400 nm, and it is more preferable that the particle size be 50 to 200 nm. In the case where the intention is to transmit liposome to macrophage, it is preferable that liposome particle size be 30 to 1000 nm, and it is more preferable that the particle size be 100 to 400 nm. In the case where liposome composition is to be used as an oral preparation or trans-dermal preparation, the particle size of liposome can be set at several microns. It should be noted that (1) in normal tissue, vascular walls serve as barriers (because the vascular walls are densely constituted by vascular endothelial cells), and microparticles such as supermolecules and liposome of specified size cannot be distributed within the tissue. However, in diseased tissue, vascular walls are loose (because interstices exists between vascular endothelial cells), increasing vascular permeability, and supermolecules and microparticles can be distributed to extravascular tissue (enhanced permeability). Moreover, (2) the lymphatic system is well developed in normal tissue, but it is known that the lymphatic system is not developed in diseased tissue, and that supermolecules or microparticles, once incorporated, are not recycled through the general system, and are retained in the diseased tissue (enhanced retention)—this is called the EPR effect (Matsumura, Maeda, Cancer Research, (1986), 46: pp. 6387-6392). Consequently, it is possible to control pharmacokinetics by adjusting liposome particle size.

In the present invention, liposome particle size means the weight-average particle size according to the dynamic light scattering method (quasi-elastic light scattering method). Here, particle size is shown that is measured by dynamic light scattering instruments (e.g., Zetasizer Nano ZS model manufactured by Malvern Instruments Ltd. and ELS-8000 manufactured by Otsuka Electronics Co., Ltd.). The instruments measure Brownian motion of the particles, and particle size is determined based on established dynamic light scattering methodological theory.

There are no particular limitations on the solvent of the liposome internal phase, and one may cite, for example, buffer solutions such as phosphate buffer solution, citrate buffer solution, and phosphate-buffered physiological saline solution, physiological saline water, culture mediums for cell culturing, etc. As solvent, in the case where buffer solution is used, it is preferable that the concentration of buffer agent be 5 to 300 mM, and 10 to 100 mM is more preferable. There are no particular limitations on the pH of the liposome internal phase, but 3 to 11 is preferable, and 4 to 9 is more preferable.

(Liposome Composition)

A liposome composition is offered according to the present invention. The liposome composition contains liposome, and further contains eribulin, etc. in the liposome internal phase. As mentioned above, the liposome composition includes both a solid form and a liquid form. In the case where the liposome is in a solid form, it can be made into a liquid form by dissolving or suspending it in a prescribed solvent as described below. In the case where the liposome composition is frozen solid, it can be made into a liquid form by melting by leaving it standing at room temperature.

The concentration of liposome and the concentration of the active compound in the liposome composition can be appropriately set according to the liposome composition objective, formulation, etc. In the case where the liposome composition is a liquid formulation, the concentration of liposome as the concentration of all lipids constituting the liposome may be set at 0.2 to 100 mM, and preferably at 1 to 30 mM. The concentration (dosage) of active compound in the case where the liposome composition is used as a medicine is described below. With respect to the quantity of cyclodextrin in the liposome composition, it is preferable that it be less than a 0.1 mol equivalent relative to the eribulin, etc., and it is more preferable that it be less than the limit of detection.

In the liposome composition of the present invention, the eribulin, etc. may be apportioned to the lipid bilayer.

There are no particular limitations on the solvent (dispersion medium) of the liposome composition in the case where the liposome composition is a liquid formulation, and one may cite, for example, buffer solutions such as phosphate buffer solution, citrate buffer solution, and phosphate-buffered physiological saline solution, physiological saline water, and culture mediums for cell culturing. There are no particular limitations on the pH of the liposome external phase of the liposome composition, but 3 to 11 is preferable, and 4 to 9 is more preferable.

One may also add the following to the liposome composition: monosaccharides such as glucose, glactose, mannose, fructose, inositol, ribose, and xylose; disaccharides such as lactose, sucrose, cellobiose, trehalose, and maltose; trisaccharides such as raffinose and melizitose; polysaccharides such as cyclodextrin; and sugar alcohols such as erythritol, xylitol, sortibol, mannitol and maltitol; polyvalent alcohols such as glycerin, diglycerin, polyglycerin, propylene glycol, polypropylene glycol, ethylene glycol, diethylene glycol, triethylene glycol, polyethylene glycol, ethylene glycol monoalkylether, diethylene glycol monoalkylether, 1,3-butylene glycol. One may also use combinations of sugar and alcohol.

For purposes of stable long-term storage of the liposome that is dispersed in the solvent (dispersion medium), from the standpoint of physical stability including coagulation and so on, it is preferable to eliminate the electrolyte in the solvent (dispersion medium) as much as possible. Moreover, from the standpoint of chemical stability of the lipids, it is preferable to set the pH of the solvent (dispersion medium)

from acidic to the vicinity of neutral (pH 3.0 to 8.0), and to remove dissolved oxygen through nitrogen bubbling.

There are no particular limitations on the concentration of the sugar or polyvalent alcohol contained in the liposome composition, but in a state where the liposome is dispersed in a solvent, for example, it is preferable that the concentration of sugar be 2 to 20% (W/V), and 5 to 10% (W/V) is more preferable. With respect to the concentration of polyvalent alcohol, 1 to 5% (W/V) is preferable, and 2 to 2.5% (W/V) is more preferable. These solvents can also be used as the liposome external phase in the liposome dispersion liquid, and by substituting or diluting the liposome external phase of the liposome preparatory solution with these solvents, it is possible to change the solutions of the liposome external phase into these solutions.

It is preferable that solid formulations of the liposome composition include, for example, monosaccharides such as glucose, glactose, mannose, fructose, inositole, ribose, and xylose; disaccharides such as lactose, sucrose, cellobiose, trehalose, and maltose; trisaccharides such as raffinose and melizitose; polysaccharides such as cyclodextrine; and sugar alcohols such as erythritol, xylitol, sorbitol, mannitol, and maltitol. More preferable are blends of glucose, lactose, sucrose, trehalose, and sorbitol. Even more preferable are blends of lactose, sucrose, and trehalose. By this means, solid formulations can be stably stored over long periods. When frozen, it is preferable that solid formulations contain polyvalent alcohols (aqueous solutions) such as glycerin, diglycerin, polyglycerin, propylene glycol, polypropylene glycol, ethylene glycol, diethylene glycol, triethylene glycol, polyethylene glycol, ethylene glycol monoalkylether, diethylene glycol monoalkylether and 1,3-butylene glycol. With respect to polyvalent alcohols (aqueous solutions), glycerin, propylene glycol, and polyethylene glycol are preferable, and glycerin and propylene glycol are more preferable. By this means, it is possible to stably store the solid formulation over long periods. Sugars and polyvalent alcohols may be used in combination.

(Method of Manufacture of Liposome Composition)

According to the present invention, a manufacturing method is provided for the manufacture of a liposome composition containing eribulin or its pharmacologically permissible salt. The method for manufacturing the liposome composition includes: a step in which a liposome dispersion liquid containing liposome is provided; a step in which the aforementioned liposome dispersion liquid is mixed with the aforementioned active compound (eribulin or its pharmacologically permissible salt); and a step in which the aforementioned active compound is introduced into the liposome internal phase of the aforementioned liposome dispersion liquid.

It is preferable that the step in which a liposome dispersion liquid containing liposome is provided include a step in which a liposome preparatory solution is provided, and a step in which the liposome external phase of the aforementioned liposome preparatory solution is substituted or diluted.

The liposome preparatory solution can be provided, for example, by preparing liposome in a solution containing ammonium salt. By preparing the liposome preparatory solution in a solution containing ammonium salt, it is possible to make a liposome dispersion liquid that also contains ammonium salt in the liposome internal phase.

There are no particular limitations on the solution containing ammonium salt that is used when preparing the liposome preparatory solution, and any solution containing ammonium salt may be used.

As ammonium salt, one may cite, for example, ammonium chloride, ammonium borate, ammonium sulfate, ammonium formate, ammonium acetate, ammonium citrate, ammonium tartrate, ammonium succinate, and ammonium phosphate. Ammonium sulfate, ammonium acetate, ammonium citrate, ammonium tartrate, and ammonium phosphate are preferable among these; ammonium sulfate, ammonium citrate, and ammonium tartrate are more preferable; and ammonium sulfate is most preferable.

One may use these ammonium salts in combinations of two or more.

The concentration of ammonium salt in the solution containing ammonium salt can be appropriately set according to the quantity of eribulin, etc. to be entrapped, and higher is better; 10 mM or more is preferable; 20 mM or more is more preferable; and 50 mM or more is even more preferable. With respect to the pH of the solution containing ammonium salt, 3 to 9 is preferable, 4 to 9 is more preferable from the standpoint of balancing entrapment ratio and stability, and 5 to 8 is even more preferable.

A pH adjuster may be used in order to adjust the pH of the solution containing ammonium salt. There are no particular limitations on the concentration of the individual pH adjusters in the solution containing ammonium salt, but 1 to 300 mM is preferable, and 5 to 100 mM is more preferable.

As the pH adjuster, one may cite, for example, amino acids such as arginine, histidine, and glycine; acids such as ascorbic acid, benzoic acid, citric acid, glutaminic acid, phosphoric acid, acetic acid, propionic acid, tartaric acid, carbonic acid, lactic acid, boric acid, maleic acid, fumaric acid, malic acid, adipic acid, hydrochloric acid, and sulfuric acid; salts of the aforementioned acids such as sodium salt, potassium salt, and ammonium salt; and alkaline compounds (base) such as tris-hydroxymethylamino methane, ammonia water (ammonia), sodium hydride, and potassium hydride. As pH adjusters, sodium hydride, hydrochloric acid, ammonia water, acetic acid, lactic acid, tartaric acid, succinic acid, citric acid, and phosphoric acid are preferable; sodium hydride, ammonia water, hydrochloric acid, acetic acid, citric acid, and phosphoric acid are more preferable; and sodium hydride, ammonia water, hydrochloric acid, citric acid, and phosphoric acid are even more preferable. The pH adjusters may be used in combinations of two or more of the ammonium salts. In addition, buffer solutions may also be used as pH adjusters, such as phosphate buffer solution, citrate buffer solution, and phosphate-buffered physiological saline solution.

As the liposome preparatory solution, it is best to use a solution that is obtained by preparing liposome without substantial inclusion of cyclodextrin. As the liposome preparatory solution, the liposome internal phase may also contain salt, acid, base, and/or amino acid. In this case, it is preferable that the liposome internal phase contain the active compound, ammonium salt, and acid. As the ammonium salt, ammonium sulfate may be cited as the preferred example; as the acid, citric acid may be cited as the preferred example.

With respect to liposome preparation, one may cite the lipid film method (Vortex method), reverse phase evaporation method, ultrasonic method, pre-vesicle method, ethanol injection method, French press method, cholic acid removal method, Triton X-100 batch method, $Ca^{2+}$ fusion method, ether injection method, annealing method, freeze-thaw method, etc.

The various conditions (quantities of membrane constituents, temperature, etc.) in liposome preparation may be suitably selected according to the liposome preparation method, target liposome composition, particle size, etc. (see Op. cit, Kikuchi (1983), etc.).

The liposome particle size may be optionally adjusted as necessary. Particle size may be adjusted, for example, by conducting extrusion (extrusion filtration) under high pressure using a membrane filter of regular pore diameter. Particle size adjustment may be conducted at any timing during manufacture of the liposome composition of the present invention. For example, it may be conducted before adjustment of the liposome external phase in the liposome preparatory solution, after adjustment of the liposome external phase in the liposome preparatory solution, or after introduction of the active compound into the liposome internal phase. It is preferable to conduct the particle size adjustment before introducing the active compound into the liposome internal phase, and it is more preferable to conduct it before adjusting the liposome external phase in the liposome preparatory solution.

The liposome dispersion liquid can be obtained by substituting or diluting the external phase of the obtained liposome preparatory solution. The substitution or dilution of the liposome external phase may be conducted once, or a combination of various types of substitution or dilution methods may be conducted multiple times.

As a method for substituting the liposome external phase of the liposome preparatory solution, one may cite dialysis, centrifugal separation, and gel filtration. By substituting the liposome external phase, the present invention can be implemented so that the liposome external phase does not substantially contain cyclodextrin or ammonium salt. Moreover, by substituting or diluting the liposome external phase, it is possible to efficiently entrap eribulin or its pharmacologically permissible salt in the liposome internal phase.

Dialysis may be conducted, for example, using a dialysis membrane. As a dialysis membrane, one may cite a membrane with molecular weight cut-off such as a cellulose tube or Spectra/Por.

With respect to centrifugal separation, centrifugal acceleration may be conducted preferably to 100,000 g or higher, and more preferably to 300,000 g or higher. By substituting the liposome external phase by centrifugation, one may also conduct liposome concentration in conjunction with substitution of the liposome external phase.

Gel filtration may be carried out, for example, by conducting fractionation based on molecular weight using a column such as Sephadex or Sepharose.

As the solvent (dispersion medium) used when substituting and/or diluting the liposome external phase, one may cite, for example, sucrose solution, saline solution, and culture medium for cell culturing. By using these solvents, it is possible to prepare a stable liposome composition.

There are no particular limitations on the pH of said solvent, but a range of 2 to 11 may be set; 3 to 10 is preferable, 6 to 10 is more preferable, and 7 to 10 is even more preferable. As described below, a pH gradient may be used to introduce the eribulin, etc. into the liposome internal phase. In this case, the pH of the solvent may be set so that the liposome external phase attains the target pH.

A pH adjuster may be used in order to adjust the pH of said solvent. There are no particular limitations on the concentration of use, but 1 to 300 mM is preferable, and 5 to 100 mM is more preferable.

As the pH adjuster, one may cite, for example, amino acids such as arginine, histidine, and glycine; acids such as ascorbic acid, benzoic acid, citric acid, glutaminic acid, phosphoric acid, acetic acid, propionic acid, tartaric acid, carbonic acid, lactic acid, boric acid, maleic acid, fumaric acid, malic acid, adipic acid, hydrochloric acid, and sulfuric acid; salts of the aforementioned acids such as sodium salt, potassium salt, and ammonium salt; and alkaline compounds such as tris-hydroxymethylamino methane, ammonia water, sodium hydride, and potassium hydride. Sodium hydride, hydrochloric acid, histidine, tartaric acid, succinic acid, citric acid, and phosphoric acid are preferable; sodium hydride, hydrochloric acid, histidine, tartaric acid, citric acid, and phosphoric acid are more preferable; and sodium hydride, hydrochloric acid, histidine, and phosphoric acid are even more preferable.

In order to improve the entrapment ratio of eribulin or its pharmacologically permissible salt in liposome, the entrapment ratio can be increased by adding a solution (salt solution) containing electrolyte to the liposome external phase to increase ion intensity. There are no particular limitations on the electrolyte (salt) contained in the liposome external phase, but sodium chloride and potassium chloride are preferable, and sodium chloride is more preferable. Physiological saline solution can also be used. Moreover, as the liposome external phase of the liposome dispersion liquid or the like, sugar, electrolyte, and/or amino acid may be included, and sugar or electrolyte, and amino acid may also be included. As sugar, sucrose may be cited as the preferred example; as electrolyte, physiological saline solution and sodium chloride may be cited as preferred examples; and as amino acid, histidine may be cited as the preferred example.

It is preferable that the obtained liposome dispersion liquid not substantially contain cyclodextrin or ammonium salt in the liposome external phase and liposome internal phase, but in the present invention, eribulin or its pharmacologically permissible salt may be introduced into the liposome internal phase even in the case where cyclodextrin or ammonium salt has for some reason been added to the liposome external phase of the liposome dispersion liquid, and even when the liposome external phase of the liposome dispersion liquid contains cyclodextrin or ammonium salt.

With respect to the lipid concentration of liposome in the liposome dispersion liquid, 1 to 100 mM is preferable, and 1-50 mM is more preferable. Within these ranges, it is possible to suitably form a greater number of liposome particles without impairing the physical properties of the liposome dispersion liquid.

The liposome composition can be obtained by mixing the obtained liposome dispersion liquid and the active compound of eribulin, etc., and by introducing the active compound into the liposome internal phase of the liposome dispersion liquid. It is preferable that the step of introduction include a step in which the membrane permeability of the liposome is enhanced in the mixed solution of liposome dispersion liquid and the active compound. By this means, entrapment of the eribulin, etc. in the liposome can be accomplished in a shorter period of time. However, even if no particular operations are conducted for the purpose of enhancing the membrane permeability of the liposome after mixing of the liposome dispersion liquid and the eribulin, etc., it is possible to entrap the eribulin, etc. in the liposome if the required time is taken.

In the step in which eribulin or its pharmacologically permissible salt is mixed, it is possible to use a substance dissolved in a solvent or a solid substance as the eribulin, etc. There are no particular limitations on the solvent, and one may use, for example, a substance identical to the liposome external phase of the liposome dispersion liquid.

At one's option as necessary, it is possible to use a pH gradient in introducing the eribulin, etc. into the liposome internal phase. In this case, with respect to the pH of the liposome internal phase of the liposome dispersion liquid, 3 to 9 is preferable, 4 to 9 is more preferable, and 5 to 8 is even more preferable.

Moreover, it is possible to set the pH of the liposome external phase higher than the pH of the liposome internal phase to create a pH gradient. A pH gradient of 1 to 5 is preferable, and 2 to 3 is more preferable.

Furthermore, it is possible to increase the entrapment ratio in the liposome by bringing the pH of the liposome external phase closer to the vicinity of the pKa of the eribulin, etc. 7.5 to 12.5 is preferable, 8.5 to 11.5 is more preferable, and 9 to 10.5 is even more preferable (the pKa of eribulin mesylate is 9.6).

As the liposome preparatory solution, it is optimal to use a solution that is obtained by preparing liposome without substantial inclusion of cyclodextrin.

As a method of enhancing the membrane permeability of liposome in the obtained mixed solution, one may cite the method of heating the mixed solution, the method of adding a membrane fluidizer to the mixed solution, etc.

In the case where the mixed solution is heated, the active compound can generally be more efficiently introduced into the liposome internal phase by heating to higher temperatures. Specifically, it is preferable to set the temperature of heating taking into consideration the thermal stability of the active compound and the employed liposome membrane constituents. In particular, it is preferable that the temperature of heating be set to the phase transition temperature of the lipid bilayer membrane of the liposome or higher.

The "phase transition temperature" of the lipid bilayer membrane of liposome means the temperature at which heat absorption starts (the temperature when endothermic reaction begins) in differential thermal analysis of elevated temperatures conditions. Differential thermal analysis is a technique enabling analysis of the thermal properties of specimens by measuring the temperature differences of a specimen or reference substance as a function of time or temperature while changing the temperature of the specimen or reference substance. In the case where differential thermal analysis is conducted with respect to liposome membrane constituents, the liposome membrane components fluidize as temperature increases, and endothermic reaction is observed. As is widely known in this technical field, the temperature range in which endothermic reaction is observed greatly varies according to the liposome membrane components. For example, in the case where liposome membrane components consist of a pure lipid, the temperature range in which endothermic reaction is observed is extremely narrow, and endothermic reaction is often observed within a range of ±1° C. relative to the endothermic peak temperature. On the other hand, in the case where liposome membrane components consist of multiple lipids, and particularly in the case where liposome membrane components consist of lipids derived from natural materials, the temperature range in which endothermic reaction is observed tends to widen, and endothermic reaction is observed, for example, within a range of ±5° C. relative to the endothermic peak temperature (that is, a broad peak, etc. is observed). According to the present invention, it is thought that liposome membrane fluidization is increased, and membrane permeability of the active compound is increased by raising the temperature higher than the phase transition temperature of the liposome lipid bilayer membrane.

For example, although dependent on the thermal stability and so on of the active compound and the employed liposome membrane constituents, it is preferable to have a temperature range from the phase transition temperature of the liposome lipid bilayer membrane to +20° C. of the phase transition temperature; a temperature range from the phase transition temperature to +10° C. of the phase transition temperature is more preferable; and a temperature range from +5° C. of the phase transition temperature to +10° C. of the phase transition temperature is even more preferable.

The heating temperature is ordinarily 20 to 100° C.; 40 to 80° C. is preferable; and 45 to 65° C. is more preferable.

Specifically, in the case of a liposome membrane whose principal ingredients are dipalmitoyl phosphatidylcholine (phase transition temperature as simple substance: 41° C.) and cholesterol, although it also depends on the composition thereof, a heating temperature of 40 to 60° C. is ordinarily preferable, and 45 to 50° C. is more preferable. Moreover, in the case of a liposome membrane whose principal ingredients are hydrogenated soy phosphatidylcholine (HSPC; phase transition temperature as simple substance: 50 to 60° C.) and cholesterol, although it also depends on the composition thereof, a heating temperature of 50 to 70° C. is ordinarily preferable, and 55 to 65° C. is more preferable. However, these heating temperatures in no way limit the present invention.

In the heating step, there are no particular limitations on the time at which the temperature is maintained at or above the phase transition temperature, and this may be properly set within a range, for example, of several seconds to 30 minutes. Taking into consideration the thermal stability of the active compound and lipids as well as efficient mass production, it is desirable to conduct the treatment within a short time. That is, it is preferable that the elevated temperature maintenance period be 1 to 30 minutes, and 2 minutes to 5 minutes is more preferable. However, these temperature maintenance times in no way limit the present invention.

Moreover, as stated above, it is also possible to enhance liposome membrane permeability by adding a membrane fluidizer to the obtained mixed solution (that is, adding it to the external phase side of the liposome). As a membrane fluidizer, one may cite organic solvents, surfactants, enzymes, etc. that are soluble in aqueous solvents. More specifically, as organic solvents, one may cite, for example, monovalent alcohols such as ethyl alcohol and benzyl alcohol; polyvalent alcohols such as glycerin and propylene glycol; aprotic polar solvents such as dimethyl sulfoxide (DMSO). As surfactants, one may cite, for example, anionic surfactants such as fatty acid sodium, monoalkyl sulfate, and monoalkyl phosphate; cationic surfactants such as alkyl trimethyl ammonium salt; ampholytic surfactants such as alkyl dimethylamine oxide; and non-ionic surfactants such as polyoxyethylene alkylether, alkyl monoglyceryl ether, and fatty acid sorbitan ester. As enzymes, one may cite, for example, cholinesterase and cholesterol oxidase. Those skilled in the art may set the quantity of membrane fluidizer according to the composition of liposome membrane constituents, the membrane fluidizer, etc., and taking into consideration the degree of efficiency of entrapment of the active compound due to addition of the membrane fluidizer, the stability of the liposome, etc.

The manufacturing method of the liposome composition of the present invention may include a step of adjusting the liposome external phase pH of the obtained liposome composition after the above-mentioned introduction step.

The external phase pH to be adjusted is not particularly limited, but may be preferably 4 to 10, more preferably 5 to 9, and even more preferably neutral 6 to 8 from the standpoint of chemical stability of the phospholipid composing the liposome.

In addition, a step of drying the obtained liposome composition may be further included. That is, when using a liposome composition as a liquid formulation, the liposome composition in a liquid form obtained in the above-mentioned introduction step may be used without modification as the final liposome composition, or the liposome external phase in the liquid liposome composition obtained in the above-mentioned introduction step may be adjusted (replaced, etc.) to make a final liposome composition. When doing so, the adjustment of the liposome external phase may be carried out similarly to the adjustment of the liposome external phase in a liposome preparatory liquid. In the case where the liposome composition is a liquid formulation, it may be used without further modification.

Furthermore, in the case where the liposome composition is to be made into a solid preparation, the liquid liposome composition obtained in the above-mentioned introduction step may be dried to make the final solid liposome composition. Freeze drying and spray drying may be cited as examples of methods for drying the liposome composition. In cases where the liposome composition is a solid preparation, it may be dissolved or suspended in a suitable solvent and used as a liquid formulation. The solvent to use may be appropriately set according to the purpose of use, etc. for the liposome composition, and in the case of using the liposome composition as an injection product, for example, the solvent is preferably sterile distilled water. In the case of using the liposome composition as a medicine, the physician or patient may inject the solvent into a vial into which the solid preparation is entrapped, for example, to make the preparation at the time of use. In the case where the liquid liposome composition is a frozen solid preparation, it may be used as a liquid formulation by storing in a frozen state, and returned to a liquid state by leaving to melt at room temperature or by rapidly melting with heat at the time of use.

(Pharmaceutical Compositions, etc.)

The liposome composition of the present invention may be used as a curative medicine in the medical field. Specifically, the liposome composition of the present invention may be used as an antitumor pharmaceutical composition.

In the case where the liposome composition of the present invention is used as a pharmaceutical composition, the liposome composition may be administered by injection (intravenous, intra-arterial, or local injection), orally, nasally, subcutaneously, pulmonarily, or through eye drops, and in particular local injection to a targeted group of cells or organ or other such injection is preferable in addition to intravenous injection, subcutaneous injection, intracutaneous injection, and intra-arterial injection. Tablet, powder, granulation, syrup, capsule, liquid, and the like may be given as examples of the formulation of the liposome composition in the case of oral administration. Injection product, drip injection, eye drop, ointment, suppository, suspension, cataplasm, lotion, aerosol, plaster, and the like may be given as examples of formulations of the liposome composition in the case of non-oral administration, and an injection product and drip infusion agent are particularly preferable.

The dosage of the pharmaceutical composition differs markedly depending on the type of target disease, the type of the active compound, as well as the age, sex, and weight of the patient, the severity of the symptoms, along with other factors, but ordinarily, the daily dosage of eribulin or its pharmacologically permissible salt for adults is not particularly restricted, although eribulin mesylate, which is a suitable salt, is ordinarily 0.1 to 10 mg. Also, the administration may be divided into more than one dose per day. A liposome composition containing, for example, 0.01-300 mg/mL eribulin or its [typographical error] [sic: pharmacologically] permissible salt to the liposome internal phase may be administered as the liposome composition of the present invention.

(Kit)

According to the present invention, a kit is provided for preparing the liposome composition. The kit may be used to prepare the liposome composition as a medicine, which may be used by a physician in clinical setting or a patient.

The kit includes a liposome reagent. The liposome reagent may be either a solid or a liquid form. If the liposome reagent is in a liquid form, the above-mentioned liposome dispersion liquid may be used as the liposome reagent. Also, if the liposome reagent is in a solid form, the liposome reagent can be dissolved or suspended in an appropriate solvent to obtain the liposome dispersion liquid, and the above-mentioned liposome dispersion liquid can be dried to obtain the liposome reagent. Drying may be carried out similarly to the above-mentioned drying of the liposome composition. When using the kit, if the liposome reagent is in a solid form, the liposome regent can be dissolved or suspended in an appropriate solvent to make the liposome dispersion liquid. When doing so, the solvent is similar to the liposome external phase in the above-mentioned liposome dispersion liquid.

The kit of the present invention further contains eribulin or its pharmacologically permissible salt (eribulin mesylate is a suitable salt). The eribulin or its pharmacologically permissible salt may be either in a solid or liquid form (a state of dissolved or suspended in a solvent). When using the kit, if the eribulin or the like is in a solid form, it is preferable that it be dissolved or suspended in an appropriate solvent to make a liquid form. The solvent can be appropriately set according to the physical properties and the like of the eribulin or the like, and may be made similar to the liposome external phase in the above-mentioned dispersion liquid, for example. The kit of the present invention may include an active compound other than eribulin or its pharmacologically permissible salt.

In the kit, the liposome reagent and the active compound may be packaged separately, or they may be in solid forms and mixed together.

In the case where the liposome reagent is in a solid form, excluding cases of dissolving or suspending to form a liposome dispersion liquid as above, the kit may be used by carrying out a step similar to that of mixing the liposome dispersion liquid and the active compound and of introducing the active compound in the liposome internal phase of the liposome dispersion liquid in the manufacturing method of the above-mentioned liposome composition. It is thereby possible to manufacture a liposome composition in which an active compound is introduced into the internal phase of the liposome reagent.

In the case where the liposome reagent and the active compound are both in solid forms and are packaged together, the mixture of the liposome reagent and the active compound is appropriately dissolved or suspended in a solvent. When doing so, the solvent is similar to the liposome external phase in the above-mentioned liposome dispersion liquid. It is thereby possible to form a state in which the liposome dispersion liquid and the active compound are mixed, after which use is made possible by carrying out other steps in the introduction of the active compound in the liposome internal phase of the liposome dispersion liquid in the manufacturing method of the above-mentioned liposome composition.

EMBODIMENTS

The present invention is specifically described by giving embodiments and comparative examples, but is not limited to the embodiments below.

Embodiment 1

Preparation of an Aqueous Solution for the Liposome Internal Phase 396.4 mg of ammonium sulfate and 189.1 mg of citric acid monohydrate were dissolved in pure water, and this was diluted to 15 mL to prepare 200 mM ammonium sulfate/60 mM aqueous citric acid. After adjusting 2.5 mL of the 200 mM ammonium sulfate/60 mM aqueous citric acid with aqueous ammonia to a pH of 5.5, the aqueous solution for the liposome internal phase was diluted to 5 mL with pure water.

<Preparation of the Liposome Preparatory Liquid>

After dissolving 317.9 mg of hydrogenated soybean phosphatidylcholine (manufactured by Lipoid), 116.0 mg of cholesterol (manufactured by Sigma), and 130.4 mg of polyethylene glycol 2000-phosphatidylethanolamine (manufactured by Genzyme, MPEG 2000-distearoyl phosphatidylethanolamine) in 10 mL of chloroform, this was accurately dispensed into three vials, after which the chloroform of one vial was removed under reduced pressure in a rotary evaporator to create a lipid film. 5 mL of the aqueous solution for the liposome internal phase was heated to approximately 60° C. and added to the obtained lipid film, and this was agitated to prepare a liposome preparatory liquid. After treating the liposome preparatory liquid with ultrasonic waves for 20 minutes, it was granulated with an extruder (manufactured by Lipex Biomembranes) heated to approximately 65° C. to obtain the liposome preparatory liquid. The particle size of the liposomes in the obtained liposome preparatory liquid was measured using a dynamic light scattering method, and all were 90 to 100 nm.

<Preparation of the Liposome Dispersion Liquid>

Using Sephadex G-50 columns, the obtained liposome preparatory liquid was eluted with 0.9% sodium chloride/10 mM histidine aqueous solution (pH=7.6), substituting the liposome external phase with the 0.9% sodium chloride/10 mM histidine aqueous solution. After substituting the liposome external phase, this was centrifuged for 30 minutes at 400,000×g. After the centrifuging, this was redispersed, and 0.9% sodium chloride/10 mM histidine aqueous solution was used to prepare a volume of 5 mL, obtaining the liposome dispersion liquid.

<Preparation of the Active Compound Solution>

The eribulin mesylate was dissolved in 0.9% sodium chloride/10 mM histidine aqueous solution to obtain 1 mg/mL eribulin mesylate.

<Preparation of the Liposome Composition>

0.5 mL of the liposome dispersion liquid and 0.5 mL of the eribulin mesylate solution were mixed in a 10-mL glass vessel, and this was incubated for 3 minutes in 55° C. water to obtain a liposome composition with eribulin mesylate introduced in the liposomes.

<Measurement of the Entrapment Ratio>

The entrapment ratio was determined as described below. The liposome composition entrapping an active compound was ultracentrifuged for 30 minutes at 400,000×g. The active compound concentration in the filtrate was measured with HPLC, quantitating the amount of active compound not entrapped in the liposomes. The entrapment ratio was calculated using the formula below.

$$\text{Entrapment ratio (\%)} = \frac{\text{Qty. of active compound in total qty. (mg)} - \text{Qty. of active compound in filtrate after ultracentrifugation (mg)}}{\text{Qty. of active compound in total qty. (mg)}} \times 100 \quad \text{(Formula 1)}$$

The entrapment ratio of eribulin mesylate was 90.9%.

Embodiment 2

Preparation of the Aqueous Solution for the Liposome Internal Phase

Similarly to Embodiment 1, 264.3 mg of ammonium sulfate and 126.1 mg of citric acid monohydrate were dissolved in pure water, and a graduated flask was used to dilute this to 10 mL to prepare 200 mM ammonium sulfate/60 mM aqueous citric acid. Of this, 1 mL was taken and adjusted to a pH of 5.5 with ammonia water, after which this was diluted with pure water to 2 mL to prepare the aqueous solution for the liposome internal phase.

<Preparation of the Liposome Preparatory Liquid>

80 mg each of a lipid mixture (hydrogenated soybean phosphatidylcholine:cholesterol:polyethylene glycol 2000-phosphatidylethanolamine=58.6:19.2:22.2 (by weight)) was weighed, 2 mL of the aqueous solution for the liposome internal phase was heated to approximately 80° C. and added thereto, and this was agitated to prepare the liposome preparatory liquid. This liposome preparatory liquid was granulated using an extruder (manufactured by Lipex Biomembranes) heated to approximately 80° C. to obtain the liposome preparatory liquid.

<Preparation of the Liposome Dispersion Liquid>

The obtained liposome preparatory liquid was diluted to 10 mL with the 0.9% sodium chloride/10 mM histidine aqueous solution (pH=7.6), and this was centrifuged for 30 minutes at 400,000×g. After centrifuging, all of the filtrate was disposed. The precipitate was redispersed with the 0.9% sodium chloride/10 mM histidine aqueous solution, and a graduated flask was used to prepare 1 mL of liquid, obtaining the liposome dispersion liquid.

<Preparation of the Drug Solution>

Eribulin mesylate (eribulin mesylate) was dissolved in the 0.9% sodium chloride/10 mM histidine aqueous solution and 5 mg/mL eribulin mesylate solution was obtained.

<Preparation of the Liposome Composition>

0.96 mL of the liposome dispersion liquid and 0.24 mL of the eribulin mesylate solution were mixed in a 10-mL glass vessel, and this was incubated for 3 minutes in 60° C. water to obtain a liposome composition with eribulin mesylate introduced in the liposomes.

<Stability in Rat Blood Plasma>

0.2 mL of the prepared eribulin mesylate entrapped liposome and 1.8 mL of rat blood plasma were mixed, and this was shaken at 37° C. using a liquid phase incubator. Immediately after the preparation, sampling was performed at 6 hours, 12 hours, 24 hours, 48 hours and 72 hours after the shaking was begun, and the residual quantity of eribulin mesylate in the liposomes was measured with HPLC.

The measurement results are shown in FIG. 1. As can be seen in FIG. 1, it was indicated that the eribulin mesylate was stably retained in the blood plasma even over the long time span of 120 hours, and gradual release was possible.

Embodiment 3

Preparation of the Aqueous Solution for the Liposome Internal Phase 264.3 mg of ammonium sulfate and 126.1 mg of citric acid monohydrate were dissolved in pure water to obtain approximately 15 mL. After adjusting the pH to 7.0 with aqueous sodium hydroxide, this was diluted with pure water to 20 mL to prepare the aqueous solution for the liposome internal phase (100 mM ammonium sulfate/30 mM citric acid).

<Preparation of the Liposome Preparatory Liquid>

378 mg of a lipid mixture (hydrogenated soybean phosphatidylcholine:cholesterol:polyethylene glycol 2000-phosphatidylethanolamine=58.6:19.2:22.2 (by weight)) was weighed, 10 mL of the above-mentioned aqueous solution for the liposome internal phase was heated to approximately 80° C. and added thereto, and this was agitated to prepare the liposome preparatory liquid. This liposome preparatory liquid was granulated using an extruder (manufactured by Lipex Biomembranes) provided with a 50-nm polycarbonate membrane filter and heated to approximately 80° C. to obtain the liposome preparatory liquid with a particle size of approximately 80 nm.

<Preparation of the Liposome Dispersion Liquid>

Using Sephadex G-50 columns, the obtained liposome preparatory liquid was eluted with 0.9% sodium chloride/10 mM histidine aqueous solution (pH=7.6), substituting the liposome external phase with the 0.9% sodium chloride/10 mM histidine aqueous solution. After substituting the liposome external phase, this was centrifuged for 30 minutes at 400,000×g. After centrifuging, this was redispersed with 96 mg/mL sucrose/10 mM histidine aqueous solution (pH=7.6), and 10 mL of the solution was diluted to 10 mL to obtain the liposome dispersion liquid.

<Preparation of the Drug Solution>

Eribulin mesylate was dissolved with the 96 mg/mL sucrose/10 mM histidine aqueous solution (pH=7.6) and 5 mg/mL eribulin mesylate solution was obtained.

<Preparation of the Liposome Composition>

9.6 mL of the liposome dispersion liquid and 1.2 mL of the eribulin mesylate solution were mixed in a 10-mL glass vessel, and sodium hydroxide was used to adjust the pH to 9.5. This was incubated for 3 minutes in 60° C. water to obtain a liposome composition with eribulin mesylate introduced in the liposomes. After cooling, chloride was used to adjust the pH to 7.5. Similarly to Embodiment 1, the entrapment ratio was measured and found to be 99%.

Embodiment 4

Preparation of the Aqueous Solution for the Liposome Internal Phase

Similarly to Embodiment 1, 100 mM ammonium sulfate/30 mM citric acid (pH=5.5) was prepared.

<Preparation of the Liposome Preparatory Liquid>

Hydrogenated soybean phosphatidylcholine, cholesterol, and polyethylene glycol 2000-phosphatidylethanolamine were weighed according to the quantities shown in Table 1 below. After dissolving each in 3 mL of chloroform, the chloroform was removed under reduced pressure in a rotary evaporator to create a lipid film. 10 mL of the prepared aqueous solution for the liposome internal phase was heated to approximately 80° C. and added to the obtained lipid film, and this was agitated to prepare a liposome preparatory liquid. This was granulated using an extruder (manufactured by Lipex Biomembranes) heated to approximately 80° C. to obtain the granulated liposome preparatory liquid. The particle size of the liposomes in the obtained liposome preparatory liquid was measured using a dynamic light scattering method, and Rp. 1 was 77 nm, Rp. 2 95 nm, Rp. 3 79 nm, and Rp. 4 128 nm.

TABLE 1

| Rp. | Hydrogenated soybean phosphatidylcholine | Cholesterol | Polyethylene glycol 2000-phosphatidylethanolamine |
|---|---|---|---|
| 1 | 234 mg | 76 mg | 15 mg |
| 2 | 234 mg | 76 mg | 15 mg |
| 3 | 222 mg | 73 mg | 87 mg |
| 4 | 222 mg | 73 mg | 87 mg |

<Preparation of the Liposome Composition>

Similarly to Embodiment 1, the liposome dispersion liquid was obtained. Also, eribulin mesylate was dissolved in 0.9% sodium chloride/10 mM histidine aqueous solution, and 5 mg/mL eribulin mesylate was obtained.

4.8 mL of each of the liposome dispersion liquids and 0.6 mL of eribulin mesylate solution were mixed in 10-mL glass vessels, which were incubated for 3 minutes in 60° C. water to obtain liposome compositions with eribulin mesylate introduced in the liposomes. 24.6 mL of the 0.9% sodium chloride/10 mM histidine aqueous solution was added to each of the liposome compositions, and a 0.22-µm polyvinylidene fluoride (PVDF) filter was used for filtering and sterilization, obtaining an administration sample (eribulin mesylate concentration: 0.1 mg/mL). Similarly to Embodiment 1, the entrapment ratio was measured and confirmed to be at least 90% in each of the prescriptions.

Female nude mice (NU/NU, Charles River Laboratories Japan, Inc.) were subcutaneously inoculated with human melanoma LOX cells, and 11 or 12 days later, the samples were administered into the caudal veins so as to be 10 mL/kg (1.0 mg/kg for the eribulin mesylate). A blood sample was taken and tumor tissue extraction was carried out with a cardiac puncture at fixed periods after administration (15 minutes, 30 minutes, 1, 2, 4, 8, 12, 24, 36, and 48 hours) (n=3). The blood was sampled in a test tube containing heparin, and within 30 minutes of the sampling, the blood was separated by centrifuging at 1,500×g for 10 minutes at 4° C. to obtain the blood plasma. All of the tumor tissue was extracted, washed with PBS, and wiped with water-absorbent paper, and then the tissue weight was immediately weighed and recorded. The tissue was placed in a test tube and cooled in ice water, and then stored at −80° C. until analysis was carried out.

The eribulin mesylate in the blood plasma and in the tumor tissue was measured using LC/MS/MS.

The PK parameters were calculated using non-compartment model analysis software (WinNonlin version 5.0.1). The results of the blood plasma PK parameters and tumor tissue PK parameters of the eribulin mesylate are shown respectively in Table 2 and Table 3.

TABLE 2

Rp. 1-4 and eribulin mesylate blood plasma
PK parameters in LOX cancer-bearing mice

| Prescription | $AUC_{0-1}$ (ng·hr/mL) | $AUC_{0-\infty}$ (ng·hr/mL) | CL (mL/hr/kg) | $V_{ss}$ (mL/kg) | $t_{1/2}$ (hr) | MRT (hr) | Ratio 1 |
|---|---|---|---|---|---|---|---|
| Rp. 1 | 253049 | 258274 | 3.87 | 43.99 | 8.7 | 11.4 | 707.1 |
| Rp. 2 | 176148 | 177893 | 5.62 | 56.40 | 6.8 | 10.0 | 487.0 |
| Rp. 3 | 228151 | 233067 | 4.29 | 48.93 | 8.4 | 11.4 | 638.1 |
| Rp. 4 | 221494 | 230541 | 4.34 | 55.88 | 9.4 | 12.9 | 631.2 |
| Eribulin mesylate | 363.02 | 365.247 | 2420 | 8032 | 3.7 | 3.3 | 1.0 |

Ratio 1 = $AUC_{plasma\ liposome}/AUC_{plasma\ eribulin\ mesylate}$

TABLE 3

Rp. 1-4 and eribulin mesylate blood plasma
PK parameters in LOX cancer-bearing mice

| Prescription | $C_{[max]}$ (ng/g) | $T_{[max]}$ (hr) | $AUC_{0-1}$ (ng·hr/mL) | $AUC_{0-\infty}$ (ng·hr/mL) | $t_{1/2}$ (hr) | MRT (hr) | TPI (mL/g) | Ratio 2 |
|---|---|---|---|---|---|---|---|---|
| Rp. 1 | 692.1 | 4.0 | 24960.7 | 34581.8 | 22.8 | 38.8 | 0.13 | 5.5 |
| Rp. 2 | 1002.9 | 8.0 | 16759.6 | 22301.1 | 22.2 | 34.5 | 0.13 | 3.5 |
| Rp. 3 | 3965.7 | 12.0 | 41643.7 | 46297.3 | 16.1 | 23.3 | 6.20 | 7.4 |
| Rp. 4 | 1132.8 | 12.0 | 28377.4 | 45005.6 | 23.7 | 44.3 | 0.20 | 7.2 |
| Eribulin mesylate | 323.425 | 0.25 | 4649.521 | 6294.283 | 17.8 | 27.7 | 17.23 | 1.0 |

Ratio 2 = $AUC_{tumor\ liposome}/AUC_{tumor\ eribulin\ mesylate}$

From Table 2 and Table 3, it can be seen that the AUC of the blood plasma and tumor tissue is increased in comparison to the free eribulin mesylate in all four liposome compositions 1 to 4 and therefore, the tumor migration quantity and retention of the eribulin mesylate are improved.

Embodiment 5

Preparation of the Aqueous Solution for the Liposome Internal Phase

Similarly to Embodiment 1, 100 mM ammonium sulfate/30 mM aqueous citric acid (pH=5.5) was prepared.

<Preparation of the Liposome Preparatory Liquid>

221.8 mg of hydrogenated soybean phosphatidylcholine, 72.5 mg of cholesterol, and 86.9 mg of polyethylene glycol 2000-phosphatidylethanolamine were weighted. After dissolving them in 3 mL of chloroform, the chloroform was removed under reduced pressure in a rotary evaporator, and a lipid film was created. 10 ML of the created aqueous solution for the liposome internal phase were heated to approximately 80° C. and added to the obtained lipid film, and this was agitated to prepare a liposome preparatory liquid. This was granulated using an extruder (manufactured by Lipex Biomembranes) heated to approximately 80° C., and a granulated liposome preparatory liquid was obtained. When the particle sizes of the liposomes in the obtained liposome preparatory liquid were measured using a dynamic light scattering method, they were approximately 90 nm.

<Preparation of the Liposome Dispersion Liquid>

Using Sephadex G-50 columns, the obtained liposome preparatory liquid was eluted with 0.9% sodium chloride/10 mM histidine aqueous solution (pH=7.6), substituting the liposome external phase with the 0.9% sodium chloride/10 mM histidine aqueous solution. After substituting the liposome external phase, this was centrifuged for 30 minutes at 400,000×g. After the centrifuging, this was redispersed, and the 0.9% sodium chloride/10 mM histidine aqueous solution was used to prepare 10 mL of liquid, creating a liposome dispersion liquid.

<Preparation of the Drug Solution>

Eribulin mesylate was dissolved in the 0.9% sodium chloride/10 mM histidine aqueous solution and 1 mg/mL eribulin mesylate solution was obtained. Also, as administration samples of free bodies, the eribulin mesylate solution was diluted with the 0.9% sodium chloride/10 mM histidine aqueous solution, and a 0.22-µm PVDF filter was used for filtering and sterilizing to obtain administration samples (eribulin mesylate concentrations: 0.3 mg/mL and 0.4 mg/mL).

<Preparation of the Liposome Composition>

1.8 mL of the liposome dispersion liquid and 1.2 mL of the eribulin mesylate solution were each mixed in a 10 mL glass vessel, which was incubated for 3 minutes in 60° C. water to obtain a liposome composition with eribulin mesylate introduced in the liposomes. The obtained liposome composition was diluted with the in 0.9% sodium chloride/10 mM histidine aqueous solution, and a 0.22-µm PVDF filter was used for filtering and sterilizing to obtain an administration sample (eribulin mesylate concentration: 0.2 mg/mL). Similarly to Embodiment 1, the entrapment ratio was measured and confirmed to be at least 90%.

FaDu (obtained from the American Type Culture Collection), which is a human pharyngeal squamous cell carcinoma line, was cultured and grown in a 10% bovine fetal serum-containing MEM culture. The cells were separated from the flask using 0.05% Trypsin-EDTA solution and collected. After washing with PBS, the cells were suspended in PBS so as to be 5×10$^7$ cells/mL and kept on ice. 0.1 mL of cell suspension liquid were subcutaneously injected in the right ventral portion of 6-week old nude mice (Charles River Laboratories Japan, Inc.). Each mouse was observed daily, and notes were made appropriately in cases where abnormal conditions were found. Calipers were used to measure the tumor size over time, and the tumor size was calculated based on the calculation formula: major axis×(minor axis squared)÷2. At the point when the tumor size was 100 to 200 mm³, the mice were separated into groups such that the average values of the tumor sizes and the mouse body weights were uniform among the test groups (five mice per test group), and the drug was administered into the caudal vein (0.2 mL/20 g; 3 times in 7-day intervals).

The resulting changes in average tumor volume after sample administration are shown in FIG. 2.

As shown in FIG. 2, a tumor-reducing effect was not obtained even at 4 mg/kg, which is the maximum tolerated dose for free bodies, because FaDu is a cell line with a low sensitivity to eribulin mesylate. Meanwhile, in the case of the liposome composite, a clear tumor-reducing effect was found even with the administration of 2 mg/kg, which is below the maximum tolerance dose, indicating that an extremely high pharmacological effect can be obtained even for types of cancers against which there has been no success with eribulin mesylate.

Embodiment 6

Preparation of the Aqueous Solution for the Liposome Internal Phase

Similarly to Embodiment 1, 100 mM ammonium sulfate/30 mM aqueous citric acid (pH=5.5) was prepared.
<Preparation of the Drug Solution>
Similarly to Embodiment 5, administration samples (eribulin mesylate concentrations: 0.2 mg/mL, 0.3 mg/mL, and 0.4 mg/mL) of free bodies were obtained.
<Preparation of the Liposome Composition>
Except for the use of the liposome internal phase solution aqueous solution [sic: aqueous solution for the liposome internal phase] prepared as described above, the liposome composition (eribulin mesylate concentration: 0.3 mg/mL) was obtained similarly to Embodiment 5. Similarly to Embodiment 1, the entrapment ratio was measured and found to be at least 90%.

ACHN (obtained from the American Type Culture Collection), which is a human renal cancer cell line, was cultured and grown in a 10% bovine fetal serum-containing MEM culture. The cells were separated from the flask using 0.05% Trypsin-EDTA solution and collected. After washing with PBS, the cells were suspended in PBS so as to be 5×10⁷ cells/mL and then kept on ice. 0.1 mL of cell suspension liquid were subcutaneously injected in the right ventral portion of 6-week old nude mice (Charles River Laboratories Japan, Inc.). Each mouse was observed daily, and notes made appropriately in cases where abnormal conditions were found. Calipers were used to measure the tumor size over time, and the tumor size was calculated based on the calculation formula: major axis×(minor axis squared)÷2. At the point when the tumor size was 150 to 200 mm³, the mice were separated into groups such that the average values of the tumor sizes and the body weights of mice were uniform among the test groups (five mice per test group), and the drug was administered into the caudal vein (0.2 mL/20 g; 3 times in 7-day intervals).

The results of the change in average tumor volume after sample administration are shown in FIG. 3.

As shown in FIG. 3, because ACHN is a cell line that is resistant to eribulin mesylate, no significant difference was found between any of the 2 mg/kg administration, 3 mg/kg administration, and 4 mg/kg (maximum tolerance dose) free body administration groups and the non-treated group 45 days after the start of sample administration. Meanwhile, in the liposome composition 3 mg/kg administration group, a tumor-growth suppression effect was found, and a significant minor tumor volume value was indicated for the untreated group and the free body administration groups 45 days after start of sample administration. As thus indicated, it is possible to delay the growth of a tumor by preparing a liposomal formulation for a tumor for which a therapeutic effect has never been obtained before with eribulin mesylate.

Embodiment 7

Preparation of the Aqueous Solution for the Liposome Internal Phase

The 12 types of aqueous solutions for the internal phase shown below in Table 4 were created.
<Preparation of the Liposome Preparatory Liquid>
120 mg of a lipid mixture (hydrogenated soybean phosphatidylcholine:cholesterol:polyethylene glycol 2000-phosphatidylethanolamine=58.6:19.2:22.2 (by weight)) was weighed into test tubes, and 3 mL of each sample of the aqueous solution for the internal phase was heated to 80° C.

This liposome preparatory liquid was granulated using an extruder heated to approximately 80° C., and the liposome preparatory liquid was obtained.
<Preparation of the Liposome Dispersion Solution>
Using Sephadex G-50 columns, the obtained liposome preparatory liquid was eluted with 0.9% sodium chloride/10 mM histidine aqueous solution, substituting the liposome external phase with the 0.9% sodium chloride/10 mM histidine aqueous solution.

After substituting the liposome external phase, this was centrifuged for 1 hour at 400,000×g and the filtrate was completely removed. The precipitate was resuspended with 96 mg/mL sucrose/10 mM histidine aqueous solution (pH=7.5) so as to be approximately 2 mL.

The particle size of the obtained liposome dispersion liquid was measured using a dynamic light scattering method, and all were approximately 80 nm
<Preparation of the Drug Solution>
Eribulin mesylate was dissolved in the 96 mg/mL sucrose/10 mM histidine aqueous solution, and 5 mg/mL eribulin mesylate solution was obtained.
<Preparation of the Liposome Composition>
The liposome dispersion liquid and the eribulin mesylate solution were mixed in a 10-mL glass vessel such that the eribulin mesylate was 0.2 mg/mL and the total lipid concentration was 16 μmol/mL. This was heated for 5 minutes at 60° C. to obtain a liposome composition with eribulin mesylate introduced into the liposomes.
<Measurement of the Entrapment Ratio>
The entrapment ratio was measured similarly to Embodiment 1, and the results are shown in Table 4. As can be seen from Table 4, regardless of which ammonium salt was used in the internal phase, the entrapment ratio of eribulin mesylate clearly improved. In particular, the improvement in the entrapment ratio was marked when using ammonium sulfate, ammonium citrate, ammonium phosphate, and ammonium tartrate.

TABLE 4

| No. | Composition | pH | Osmotic pressure | Entrapment ratio (%) |
|---|---|---|---|---|
| 1 | 50 mM of ammonium sulfate | 7.5 (adjusted with hydrochloric acid or sodium hydroxide) | 300 mOsm (adjusted with sucrose) | 69.4 |
| 2 | 50 mM of sodium sulfate | | | 7.2 |
| 3 | 50 mM of ammonium acetate | | | 36.8 |
| 4 | 50 mM of sodium acetate | | | 10.2 |
| 5 | 50 mM of ammonium phosphate | | | 45.8 |
| 6 | 50 mM of sodium phosphate | | | 14.6 |
| 7 | 50 mM of ammonium citrate | | | 65.8 |
| 8 | 50 mM of sodium citrate | | | 8.7 |
| 9 | 50 mM of ammonium succinate | | | 14.7 |
| 10 | 50 mM of sodium succinate | | | 10.0 |
| 11 | 50 mM of ammonium tartrate | | | 74.7 |
| 12 | 50 mM of sodium tartrate | | | 11.6 |

Embodiment 8

Preparation of the Aqueous Solution for the Liposome Internal Phase

Similarly to Embodiment 7, the aqueous solution for the liposome internal phase was prepared from 100 mM ammonium sulfate/30 mM aqueous citric acid (pH=7.5).

<Preparation of the Liposome Preparatory Liquid>

Similarly to Embodiment 7, the above-mentioned aqueous solution for the liposome internal phase was used to prepare a liposome preparatory liquid.

<Preparation of the Liposome Dispersion Liquid>

Using Sephadex G-50 columns, the obtained liposome preparatory liquid was eluted with 0.9% sodium chloride/10 mM histidine aqueous solution, substituting the liposome external phase with the 0.9% sodium chloride/10 mM histidine aqueous solution.

After substituting the liposome external phase, this was centrifuged for 1 hour at 400,000×g, completely removing the filtrate. The precipitate was resuspended with 96 mg/mL/ 10 mM histidine aqueous solution (pH=7.5), the liposome external phase was substituted with 96 mg/mL sucrose/10 mM histidine aqueous solution (pH=7.5), and a liposome dispersion liquid was obtained. The particle size of the obtained liposome dispersion liquid was measured using a dynamic light scattering method, and it was approximately 80 nm.

The liposome dispersion liquid was dispensed into seven vials, and ammonium sulfate (adjusted to a pH of 7.5 using aqueous sodium hydroxide) of a known quantity was added to the liposome external phase such that the vials had the concentrations of Table 5, and a liposome dispersion liquid was obtained in which the ammonium sulfate in the liposome external phase was of a known concentration.

<Preparation of the Drug Solution>

Eribulin mesylate was dissolved in the 96 mg/mL sucrose/ 10 mM histidine aqueous solution and 5 mg/mL eribulin mesylate solution was obtained.

<Preparation of the Liposome Composition>

The liposome dispersion liquid and the eribulin mesylate solution were mixed in a 10-mL glass vessel such that the eribulin mesylate was 0.2 mg/mL and the total lipid concentration was 16 mM. This was heated for 5 minutes at 60° C. to obtain a liposome composition with eribulin mesylate introduced into the liposomes.

<Measurement of the Entrapment Ratio>

The entrapment ratio was measured similarly to Embodiment 1, and the results are shown in Table 5. This shows that if even 0.4 mM of ammonium sulfate is present in the liposome external phase, the entrapment ratio drops markedly, and there is almost no entrapment if 10 mM of ammonium sulfate is present.

TABLE 5

| No. | Internal water phase | External phase ammonium sulfate concentration (mM) | Entrapment ratio (%) |
|---|---|---|---|
| 1 | 100 mM ammonium sulfate | 0 | 90.4 |
| 2 | 30 mM citric acid | 0.016 | 90.8 |
| 3 | pH = 7.5 | 0.08 | 91.3 |
| 4 | | 0.4 | 75.9 |
| 5 | | 2 | 36.8 |
| 6 | | 10 | 16.1 |
| 7 | | 50 | 8.6 |

Embodiment 9

Preparation of the Aqueous Solution for the Liposome Internal Phase

Similarly to Example 7, the aqueous solution for the liposome internal phase was prepared from 100 mM ammonium sulfate/30 mM aqueous citric acid (pH=7.5).

<Preparation of the Liposome Preparatory Liquid>

Similarly to Example 7, the above-mentioned aqueous solution for the liposome internal phase was used to prepare the liposome preparatory liquid.

<Preparation of the Liposome Dispersion Solution>

Using Sephadex G-50 columns, the obtained liposome preparatory liquid was eluted with 0.9% sodium chloride/10 mM histidine aqueous solution, substituting the liposome external phase with the 0.9% sodium chloride/10 mM histidine aqueous solution.

After substituting the liposome external phase, this was centrifuged for 1 hour at 400,000×g and the filtrate completely removed. The precipitate was resuspended with 96 mg/mL sucrose/10 mM histidine aqueous solution (pH=7.5), the liposome external phase was substituted with the 96 mg/mL sucrose/10 mM histidine aqueous solution (pH=7.5), and the liposome dispersion liquid was obtained. The particle size of the obtained liposome dispersion liquid was measured using a dynamic light scattering method, and it was approximately 80 nm.

<Preparation of the Drug Solution>

Eribulin mesylate was dissolved in the 96 mg/mL sucrose/ 10 mM histidine aqueous solution and 5 mg/mL eribulin mesylate solution was obtained.

<Preparation of the Liposome Composition>

The liposome dispersion liquid and the eribulin mesylate solution were mixed in a 10-mL glass vessel such that the eribulin mesylate was 0.2 mg/mL and the total lipid concentration was 16 mM. As shown in Table 6, each pH of the liposome external phase was adjusted using 1M sodium hydroxide aqueous solution. This was heated thr 5 minutes at 60° C. to obtain a liposome composition with eribulin mesylate introduced in the liposomes. Next, hydrochloric acid was used to adjust the pH of the external phase to 7.5.

<Measurement of the Entrapment Ratio>

The entrapment ratio was measured similarly to Embodiment 1, and the results are shown in Table 6. Along with the rise in the pH of the liposome external phase, the entrapment ratio of the eribulin rose substantially, reaching an entrapment ratio of nearly 100%.

TABLE 6

| No. | Internal water phase | External phase pH | Entrapment ratio (%) |
|---|---|---|---|
| 1 | 100 mM ammonium sulfate | 7.5 | 72.9 |
| 2 | 30 mM citric acid | 8.0 | 79.8 |
| 3 | pH = 7.5 | 8.5 | 86.4 |
| 4 | | 9.0 | 92.8 |
| 5 | | 9.5 | 98.5 |
| 6 | | 10.0 | 100.0 |
| 7 | | 10.5 | 99.3 |

Embodiment 10

Preparation of the Aqueous Solution for the Liposome Internal Phase

Similarly to Example 7, the aqueous solution for the liposome internal phase was prepared from 100 mM ammonium sulfate/30 mM aqueous citric acid (pH=7.5).

<Preparation of the Liposome Preparatory Liquid>

Similarly to Example 7, the above-mentioned aqueous solution for the liposome internal phase was used to prepare the liposome preparatory liquid.

<Preparation of the Liposome Dispersion Solution>

Using Sephadex G-50 columns, the obtained liposome preparatory liquid was eluted with 0.9% sodium chloride/10 mM histidine aqueous solution, substituting the liposome external phase with the 0.9% sodium chloride/10 mM histidine aqueous solution.

The liposome dispersion liquid was dispensed into four vials, which were centrifuged for 1 hour at 400,000×g, and the filtrate was completely removed. The precipitate of two of the vials was resuspended with 96 mg/mL sucrose/10 mM histidine aqueous solution (pH=7.5), and the liposome external phase was substituted with the 96 mg/mL sucrose/10 mM histidine aqueous solution (pH 7.5). The precipitate of the remaining two vials was resuspended with the 0.9% sodium chloride/10 mM histidine aqueous solution (pH=7.5), and the liposome external phase was substituted with the 0.9% sodium chloride/10 mM histidine aqueous solution (pH=7.5). The particle size of the obtained liposome dispersion liquids was measured using a dynamic light scattering method, and all were approximately 80 nm.

<Preparation of the Drug Solution>

Eribulin mesylate was dissolved in the 96 mg/mL sucrose/10 mM histidine aqueous solution and 5 mg/mL eribulin mesylate solution was obtained. Similarly, eribulin mesylate was dissolved in the 0.9% sodium chloride/10 mM histidine aqueous solution and 5 mg/mL eribulin mesylate solution was obtained.

<Preparation of the Liposome Composition>

The liposome dispersion liquid and the eribulin mesylate solution were mixed in a 10-mL glass vessel such that the eribulin mesylate was 0.2 mg/mL, and the total lipid concentration was 16 mM. The pH of the liposome external phase of one the two vials of the 96 mg/mL sucrose/10 mM histidine aqueous solution (pH=7.5) was adjusted to 9.5 by adding sodium hydroxide. Similarly, the pH of the liposome external phase of one the two vials of the 0.9% sodium chloride/10 mM histidine aqueous solution (pH=7.5) was adjusted to 9.5 by adding sodium hydroxide. These were heated for 5 minutes at 60° C. to obtain a liposome composition with eribulin mesylate introduced into the liposomes.

<Measurement of the Entrapment Ratio>

The entrapment ratio was measured similarly to Embodiment 1, and the results are shown in Table 7. Compared to the case where the liposome external phase is a sucrose, which is nonelectrolyte, the case of sodium chloride, which is an electrolyte, clearly obtains an extremely high entrapment ratio. In addition to the electrolyte effect, application of the pH gradient to make the liposome external phase an alkali achieved a 100% entrapment ratio.

TABLE 7

| No. | Internal water phase | External phase composition | Entrapment ratio (%) |
|---|---|---|---|
| 1 | 100 mM ammonium sulfate 30 mM citric acid pH = 7.5 | 96 mg/mL sucrose 10 mM histidine pH = 7.5 | 72.9 |
| 2 | | 0.9% sodium chloride 10 mM histidine pH = 7.5 | 95.9 |
| 3 | | 96 mg/mL sucrose 10 mM histidine pH = 9.5 | 98.5 |
| 4 | | 0.9% sodium chloride 10 mM histidine pH = 9.5 | 100.0 |

The present application is based on a Japanese patent application (Japanese Patent Application 2009-082521) filed on Mar. 30, 2009, and a U.S. provisional patent application (61/164,653), and the contents thereof are incorporated herein as reference.

INDUSTRIAL APPLICABILITY

The present invention is capable of providing a method for manufacturing a liposome with a high retention stability of the active compound with a high entrapment ratio.

The liposome composition of the present invention is favorably used in therapeutic applications through the pharmacological effect of eribulin or its pharmacologically permissible salt.

The invention claimed is:

1. A pharmaceutical composition comprising a liposome: wherein the internal phase of the liposome comprises (i) eribulin and/or a pharmaceutically acceptable salt thereof, (ii) citric acid and/or a citrate salt and (iii) at least one $NH_4^+$ salt chosen from ammonium sulfate, ammonium citrate, and ammonium tartrate, and wherein the external phase of the liposome comprises no more than 0.4 mM $NH_4^+$ salt.

2. A pharmaceutical composition according to claim 1, wherein the external phase of the liposome comprises no more than 0.08 mM $NH_4^+$ salt.

3. A method for preparing a pharmaceutical composition comprising eribulin and/or a pharmaceutically acceptable salt thereof comprising:
   (a) preparing a liposome, wherein the internal phase of the liposome comprises (i) citric acid and/or a citrate salt and (ii) at least one $NH_4^+$ salt chosen from ammonium sulfate, ammonium citrate, and ammonium tartrate;
   (b) preparing a liposome dispersion liquid comprising the liposome prepared in (a) and wherein the liposome dispersion liquid does not substantially contain an ammonium salt in the liquid external to the liposome;
   (c) preparing a solution comprising eribulin and/or a pharmaceutically acceptable salt thereof;
   (d) combining the liposome dispersion lipid prepared in (b) with the eribulin solution prepared in (c);
   (e) adjusting the pH of the liposome external phase to a pH in the range of pH 9.0 to pH 10.5 either before or after the combining of part (d); and
   (f) enhancing the membrane permeability of the liposome to obtain a liposome composition comprising eribulin and/or a pharmaceutically acceptable salt thereof entrapped in the internal phase of the liposome;
   wherein the external phase of the liposome comprises no more than 0.4 mM $NH_4^+$ salt.

4. The method for preparing a pharmaceutical composition according to claim 3, further comprising:
   (g) adjusting the pH of the liposome external phase of the liposome composition obtained in (f) to a pH in the range pH 6 to 8.

5. A pharmaceutical liposome composition comprising eribulin and/or a pharmaceutically acceptable salt thereof obtained by the method for preparing according to claim 3 or 4.

* * * * *